US006659949B1

(12) United States Patent
Lang et al.

(10) Patent No.: US 6,659,949 B1
(45) Date of Patent: Dec. 9, 2003

(54) TECHNIQUE TO MEASURE CAPILLARY RELATED INTERSTITIAL FLUID USING ULTRA-SONIC METHODS AND DEVICES

(76) Inventors: Philipp Lang, 3677 Highland Ave., Redwood City, CA (US) 94062; John D. Mendlein, 680 Neptune Ave., Encinitas, CA (US) 92024

( * ) Notice: Subject to any disclaimer, the term of this patent is extended or adjusted under 35 U.S.C. 154(b) by 0 days.

(21) Appl. No.: 09/650,431

(22) Filed: Aug. 28, 2000

Related U.S. Application Data

(63) Continuation of application No. PCT/US98/17238, filed on Aug. 19, 1998, which is a continuation of application No. 08/914,527, filed on Aug. 19, 1997, now abandoned.

(51) Int. Cl.$^7$ .................................................. A61B 8/00
(52) U.S. Cl. ....................................................... 600/438
(58) Field of Search ................................ 600/437, 438, 600/448, 449, 459

(56) References Cited

U.S. PATENT DOCUMENTS

| | | |
|---|---|---|
| 4,043,181 A | 8/1977 | Nigam |
| 4,224,829 A | 9/1980 | Kawabuchi et al. |
| 4,242,911 A | 1/1981 | Martin |
| 4,274,083 A | 6/1981 | Tomoeda |
| 4,383,533 A | 5/1983 | Bhagat et al. |
| 4,413,629 A | 11/1983 | Durley, III |
| 4,446,737 A | 5/1984 | Hottier |
| 4,654,658 A | 3/1987 | Walton |
| 4,658,827 A | 4/1987 | He et al. |
| 4,669,482 A | 6/1987 | Ophir |
| 4,688,428 A | 8/1987 | Nicolas |
| 4,702,258 A | 10/1987 | Nicolas |
| 4,807,635 A | 2/1989 | Ophir |
| 4,830,015 A | 5/1989 | Okazaki |
| 4,833,323 A | 5/1989 | Scholze |
| 4,855,911 A * | 8/1989 | Lele et al. .................. 73/602 |
| 4,917,096 A | 4/1990 | Englehart et al. |
| 4,920,966 A | 5/1990 | Hon et al. |
| 4,926,870 A * | 5/1990 | Brandenburger ............ 600/437 |
| 5,038,787 A | 8/1991 | Antich et al. |
| 5,115,813 A | 5/1992 | Ylander et al. |
| 5,188,106 A | 2/1993 | Nappholz et al. |
| 5,197,475 A | 3/1993 | Antich et al. |
| 5,473,330 A | 11/1993 | Lauro et al. |
| 5,271,403 A | 12/1993 | Paulos |
| 5,303,708 A | 4/1994 | Stouffer |
| 5,305,008 A | 4/1994 | Turner et al. |
| 5,316,003 A | 5/1994 | Stouffer |
| 5,341,375 A | 8/1994 | Buchholz et al. |

(List continued on next page.)

FOREIGN PATENT DOCUMENTS

| WO | WO 93/12419 | 6/1993 |
|---|---|---|

OTHER PUBLICATIONS

*Physician's 1991 Drug Handbook*; pp. 1099–1103; 1991.
Agner, et al.; Contact Dermatitis; 20:352–359; 1989.
Agner, et al.; Clin. Exp. Dermatol.; 15:29–33; 1990.
Agner, et al.; J. Invest. Dermatol.; 95(5):543–547; 1990.
Alexander, et al.; J. Invest. Dermatol.; 72(1):17–19; 1979.
Alasaarela, et al.; Ultrasound Med. and Biol.; 20(9):975–979; 1994.
Baisch, et al.; Annual Internat. Conf. IEEE Engineering in Medicine and Biology; 12(1):285–286; 1990.
Baisch, et al.; Physiologist; 34(1)Suppl.:S181–182; 1991.
Baisch; Clin. Investig.; 71:690–399; 1993.
Barnes, et al.; Phlebology; 7:31–35; 1992.

(List continued on next page.)

*Primary Examiner*—Francis J. Jaworski
(74) *Attorney, Agent, or Firm*—Hale and Dorr LLP

(57) ABSTRACT

The present invention provides for methods and devices for monitoring capillary related interstitial thickness. The invention also includes methods of measuring capillary related interstitial fluid, as well as cardiac, vascular, renal and hepatic function. Specific devices, particularly probes, are provided for such methods.

11 Claims, 10 Drawing Sheets

U.S. PATENT DOCUMENTS

| | | | |
|---|---|---|---|
| 5,550,547 | A | 9/1994 | Chan et al. |
| 5,415,167 | A | 5/1995 | Wilk |
| 5,528,222 | A | 6/1996 | Moskowitz et al. |
| 5,547,459 | A | 8/1996 | Kaufman et al. |
| 5,564,423 | A | 10/1996 | Mele et al. |
| 5,572,226 | A | 11/1996 | Tuttle |
| 5,617,864 | A | 4/1997 | Stouffer et al. |
| 5,651,363 | A | 7/1997 | Kaufman et al. |
| 5,685,307 | A | 11/1997 | Holland et al. |
| 5,697,061 | A | 12/1997 | Krueger et al. |
| 5,743,267 | A | 4/1998 | Nikolic et al. |
| 5,785,656 | A | 7/1998 | Chiabrera et al. |
| 5,806,520 | A | 9/1998 | Berger et al. |
| 5,807,258 | A | 9/1998 | Cimochowski et al. |
| 5,810,732 | A | 9/1998 | Hamatsu et al. |
| 6,358,208 | B1 * | 3/2002 | Lang et al. .................. 600/438 |

OTHER PUBLICATIONS

Bates, et al.; *A Guide to Physical Examination and History Taking, 6th Edition* (Bates, et al., Eds.); pp. 427–447; 1995.
Berardesca, et al.; Acta. Dermatol. Venerol.; 72:261–263; 1992.
Bhagat, et al.; Ultrasound Med. Biol.; 6:369–375; 1980.
Braunwald, *Harrison's Principles of Internal Medicine* (Isselbacher, et al, Eds.); pp. 183–187; 1994.
Brazier, et al.; Contact Dermatitis; 15:199–201; 1986.
Brink, et al.; Invest. Radiol.; 21:645–651; 1986.
Buckey, et al.; Physiologist; 33(1)Suppl.:S167–168; 1990.
Buckey, et al.; Acta. Physiol. Scand.; 144(S604):53–60; 1992.
Bushberg, et al.; *The Essential Physics of Medical Imaging*; 1994.
Campbell, et al.; Am. J. Clin. Nutr.; 62:533–539; 1995.
Carpenter, et al.; Radiology; 195(2): 563–567; 1995.
Cesarone, et al.; Minerva Cardioangiolica; 43(5):211–218; 1995 (ENGLISH TRANSLATION AND ABSTRACT).
Cohen, et al.; Arthritis & Rheumatism; 27:C65; 1984.
Ciocon, et al.; Angiology; 46:19–25; 1995.
Cole, et al.; JCU; 9:501–503; 1981.
Convertino, et al.; J. Appl. Physiol.; 66(3):1509–1512;1989.
Daiqui, et al.; Physiologist; 35(1):200–201;1992.
de Rigal, et al.; Bioeng. Skin; 4:160;1988.
de Rigal, et al.; J. Invest. Dermatol.; 93(5):621–625; 1989.
Diehm, et al.; Lancet; 347:292–294; 1996.
Dines, et al.; Ultrason. Imaging; 6:408–434; 1984.
Doldi, et al., Lymphology; 25:129–133; 1992.
Dykes, et al.; J. Invest. Dermatol.; 69:275; 1977.
Escoffier, et al.; Bioeng. Skin; 2:87–94; 1986.
Fornage, et al.; J. Clin. Ultrasound; 14:619–622;1986.
Fornage, et al., Radiology; 189:69–76; 1993.
Fornage; Clinics in Diagnostic Ultrasound; 30:85–98; 1995.
Gniadecka, et al.; Br. J. Dermatol; 131:849–855; 1994.
Gniadecka, et al.; J. Invest. Dermatol; 102(3):362–364; 1994.
Gniadecka; Acta. Derm. Venereol; 75:120–154; 1995.
Gniadecka; Skin Res. Technology; 1:55–60; 1995.
Gniadecka; J. Am. Acad. Dermatol.; 35:37–41; 1996.
Goans, et al.; Med. Phys; 4:259–263; 1977.
Gottleib; *Principles of Ambulatory Medicine* (Barker, et al. Eds.); pp. 736–754; 1991.
Goss, et al.; J. Acoust. Soc. Am.; 64(2): 423–457; 1978.
Hermann, et al.; Skin Pharmacol.; 1:128–136; 1988.
Ihme, et al.; Eur. J. Clin. Pharmacol.; 50:443–447; 1996.

Johansen, et al., Osteoporosis International; 7:44–47; 1997.
Kann, et al.; Exp. Clin. Endocrinol Diabetes; 103:113–118; 1995.
Killewich, et al.; Archives of Surgery; 120(4): 424–426; 1985.
Krijnen, et al.; Dermatology ; 194:121–126; 1997.
Koskelo, et al.; Acta. Pediatric Scand.; 80:682–687; 1991.
Levy, et al.; Hautarzt; 44(7):446–451; 1993.
Ludwig, et al.; Schweizerische Rundschau fuer Medizin Praxis; 78(37):987–992; 1989.
Mani, et al.; Dermatologic Surgery; 23(1):43–45; 1997.
Mani, et al., Southampton Med. J.; 10:3–6; 1994.
Milner, et al.; Dermatologic Surgery; 23(1):43–46; 1997.
Munson; *Principles of Pharmacology, Basic Concepts and Clinical Applications*; 1995.
Myers, et al.; J. Rheumatol.; 13:577–580; 1986.
Nickell, et al.; Aviation, Space, and Env. Medicine; pp. 458–463; May, 1983.
Olsen, et al.; Acta. Dermatol. Venereol.; 73:185; 1993.
Querleux, et al.; Dermatologica; 177:332–337; 1988.
Reali, et al.; Plast. Reconstr. Surgery; 93:1050–1055; 1994.
Rehn, et al.; Arzneim.–Forsch./Drug Res.; 46(1):483–487; 1996.
Rehn, et al., Arzneim.–Forsch./Drug Res.; 46(1):488–492; 1996.
Richard, et al.; J. Invest. Dermatol.; 100(5):705–709; 1993.
Rukavina, et al.; Dermatologica; 158:81–92; 1979.
Salmi, et al.; Plastic and Reconstr. Surg.; 97:1443–1450; 1995.
Salvi, et al.; Europ. J. Endocrinol.; 131:113–119; 1994.
Sauer, et al.; Unfallchirurg; 90(8):391–393; 1987.
Schmeller, et al.; Vasa; 22(3):219–226; 1993.
Schmelzeisen, et al.; Deutsche Zeitschrift fur Mund–, Kiefer–, und Gesichts–Chirurgie; 12(3):233–239; 1988.
Seidenari et al.; Contact Dermatitis; 24:216–222; 1991.
Seidenari, et al.; Contact Dermatitis; 25:329; 1991.
Seidenari, et al.; Contact Dermatitis; 26:171–176; 1992.
Seidenari, et al.; Acta. Derm. Venereol.; Suppl. 175:3–7; 1992.
Seidenari, et al.; Acta. Derm. Venereol.; Suppl. 175:9–13; 1992.
Seidenari, et al.; Contact Dermatitis; 27:331–332; 1992.
Serup, et al.; Contact Dermatitis; 10:88–93; 1984.
Serup; Acta. Derm. Venereol.; 64:214–219; 1984.
Serup, et al.; Contact Dermatitis; 17:80–84; 1987.
Siegert; J. Oral Maxillofacial Surg.; 45(10):842–846; 1987.
Smith, et al.; Academic Press; 0161–7346/92, 213–233; 1992.
Sondergaard, et al.; Acta. Dermat. Venerol.; 65:(120)Suppl.:76–82; 1985.
Stiller, et al.; *Diagnostic Ultrasound in Dermatology*.
Tan, et al.; Br. J. Dermatol.; 106:657–667; 1982.
Tan, et al.; J. Invest. Dermatol.; 76:126–128; 1981.
Tan, et al.; *Bioengineering and the Skin* (Marks, et al. Eds.); pp. 215–225; 1981.
Tiedjen; Therapiewoche; 38:3310–3320; 1988.
Tsyb, et al.; Vestnik Rentgenologii i Radiologii; 1:52–57; 1989 (English Translation and Abstract).

* cited by examiner

TECHNIQUE TO MEASURE CAPILLARY RELATED INTERSTITIAL FLUID USING ULTRA-SONIC METHODS AND DEVICES

CROSS REFERENCE TO RELATED APPLICATIONS

This application is a continuation application claiming the benefit of an earlier filing date under 35 U.S.C. Section 120 of PCT application PCT/US98/17238 filed Aug. 19, 1998 and a continuation application claiming the benefit of an earlier filing date under 35 U.S.C. Section 120 of application Ser. No. 08/914,527 filed Aug. 19, 1997 and now abandoned, which are hereby incorporated by reference.

TECHNICAL FIELD

The invention relates to the measurement of capillary related interstitial fluid using ultrasound methods, compositions and devices, particularly methods, compositions and devices that provide for the measurement and monitoring of edema in tissues, especially a capillary related edema layer in a human.

BACKGROUND

Edema underlies a myriad of human medical conditions. Yet, despite the relatively common occurrence of edema, and its potentially life threatening nature, accurate and reliable assessments of edema are not available to the clinician or patient alike. Traditionally, methods have consisted of visual inspection of the extremities, tissue palpation by a clinician, and measurement of the circumference of the extremity. Although these methods are familiar assessments to clinicians, none of these methods is quantitative and all suffer from tremendous variability due to inter- and intra-clinician variability of the measurements.

Visual inspection of the affected body region yields information on changes in the color and texture of the skin. Skin changes in patients with edema include discoloration and ulceration. Unfortunately, such skin changes occur typically only in patients with long-standing, chronic edema and are not useful for diagnosing early or discrete edema. Furthermore, skin changes are difficult to assess on a quantitative scale and are not useful for monitoring a response to treatment of edema or the underlying cause of the edema.

Visual inspection can also yield information on arteries and veins, e.g. varicose veins may be visible and may be identified as a potential cause for capillary related edema. Such identification of vascular pathology, unfortunately, is only qualitative, is limited to assessment of the vascular system, and cannot provide information on the patient's fluid status or on cardiac, renal or hepatic performance.

Manual palpation can be used to evaluate edema. For manual palpation, a finger is pressed gently but firmly into the patient's skin and subjacent tissue. The depth of the resultant indentation and persistence of the indentation after the finger has been released yield information on the severity of the edema. A semiquantitative scale can be used to assess the severity of the edema, typically consisting of five different grades: I.) absent, II.) slight, III.) mild, IV.) moderate, and V.) severe (see Bates et al., J. B. Lippincott, 1995). Results obtained with manual palpation are, however, subjective and difficult to reproduce.

Circumference measurements of appendage regions and limbs have also been employed for assessing edema. These measurements of changes in circumference of a limb or an appendage region are limited to detecting large increases in interstitial fluid. Subtle increases or also decreases in interstitial fluid in early or mild forms of capillary related edema will be masked since the change in circumference induced by the interstitial fluid shift (usually on the order of few millimeters or less) will be small compared to the overall circumference of the appendage region or limb (usually on the order of several centimeters or decimeters).

Consequently, the present inventors have recognized the need, among other things, to provide reliable, quantitative and accurate ultrasound devices and methods for such applications, particularly hand held devices capable of being operated by untrained operators. The methods and devices provided herein permit continuous, cost effective monitoring and accurate measurement of capillary related interstitial fluid of patients in a variety of diverse clinical settings.

TABLE OF CONTENTS

CROSS REFERENCE TO RELATED APPLICATIONS
TECHNICAL FIELD
BACKGROUND
SUMMARY
BRIEF DESCRIPTION OF FIGURES
DETAILED DESCRIPTION OF THE INVENTION
  1.0 ABBREVIATIONS AND DEFINITIONS
  2.0 INTRODUCTION
  3.0 METHODS AND DEVICES FOR MEASURING CAPILLARY RELATED INTERSTITIAL FLUID
    Application Sites
    Application to Medical Treatments
    Different Types of Monitoring
    Calculations and Standards
    Empirical Methods for Determining Standards
  4.0 METHODS AND DEVICES FOR MEASURING CAPILLARY RELATED EDEMA
    Anatomical Regions
    Use in Medical Conditions and Treatments
    Devices for Testing for Capillary Related Edema
    Calculations and Standards
  5.0 METHODS AND DEVICES FOR MEASURING VASCULAR PERFORMANCE
  6.0 METHODS AND DEVICES FOR EVALUATING CARDIAC PERFORMANCE
  7.0 METHODS AND DEVICES FOR MEASURING RENAL DISORDERS AND FUNCTION
  8.0 METHODS AND DEVICES FOR MEASURING HEPATIC DISORDERS AND FUNCTION
  9.0 METHODS AND DEVICES FOR MULTISITE MONITORING
  10.0 ULTRASOUND PROBES FOR IN SITU MEASUREMENTS
EXAMPLES
  GENERAL MATERIALS AND METHODS
  EXAMPLE 1: ULTRASONOGRAPHIC MEASUREMENT OF TISSUE THICKNESS IN AN IN VITRO MODEL OF CAPILLARY RELATED EDEMA
  EXAMPLE 2: ULTRASONOGRAPHIC MEASUREMENT OF THICKNESS OF CAPILLARY RELATED EDEMA IN A MODEL OF VENOUS INSUFFICIENCY AND RIGHT VENTRICULAR CARDIAC FAILURE
  EXAMPLE 3: ULTRASONOGRAPHIC MEASUREMENT OF THICKNESS OF PRETIBIAL EDEMA IN A MODEL OF CAPILLARY RELATED EDEMA SECONDARY TO ABNORMAL COLLOID OSMOTIC PRESSURE AND/OR RENAL FAILURE PUBLICATIONS
  U.S. PATENT DOCUMENTS
  FOREIGN PATENT DOCUMENTS
  OTHER PUBLICATIONS
CLAIMS
ABSTRACT

SUMMARY

The present invention recognizes for the first time that ultrasound can be applied to the measurement of capillary related interstitial fluid. The invention finds particular application for convenient and cost effective measurements in a variety of clinical settings. Previously, it was not recognized that diagnostic ultrasound measurements of capillary related interstitial fluid were possible, or precise. Nor was it recognized that clinically rapid shifts in capillary related interstitial fluid distribution in tissues could be monitored using ultrasound methods or devices. The invention includes monitoring of capillary related interstitial fluid in a subject using ultrasound wave devices and methods as described herein. Aspects of the invention are directed to continuous or intermittent monitoring, such as capillary related edema monitoring in a human.

In one embodiment, the invention includes a method of measuring capillary related interstitial fluid comprising: transmitting at least one ultrasound signal to a tissue in a subject in need of capillary related interstitial fluid assessment, recording at least one ultrasound signal from the tissue, and determining a capillary related interstitial layer thickness from a first reflective surface to a second, usually an internal, reflective surface, wherein the capillary related interstitial layer thickness is an assessment of capillary related interstitial fluid. Typically, such a subject will be a human desiring a capillary related interstitial fluid assessment because a clinician wishes to use the invention as a part of a diagnosis or the subject wishes to perform a self assessment of the subject's capillary related interstitial fluid.

The inventors were also the first to recognize that ultrasound methods and devices could be applied to the assessment of different aspects of integrated cardiac, vascular, renal or hepatic function. Numerous aspects of the present invention circumvent many of the disadvantages of the current techniques for evaluating dynamic performance of the heart or vascular system.

For example, the present invention provides for a noninvasive assessment of vascular performance that is relatively inexpensive, easily performed by a clinician (not necessarily a physician trained in ultrasound techniques) and can integrate tissue effects into the assessment, especially capillary related tissue effects. Typically, a test of vascular performance, includes two basic steps: reducing or increasing blood flow (or pressure) to a tissue in a subject in need of vascular performance assessment (step (a)), and monitoring an interstitial layer thickness (ILT) of the tissue (step (b)). Monitoring ILT with an ultrasound probe can be before, after or concurrent with reducing or increasing blood flow in step (a).

Other techniques and devices are described herein for assessments of cardiac, renal, capillary and hepatic function. Such aspects of the invention can also be used to assess the effect of medical treatments on such physiological functions.

The invention also provides for the first time methods and devices for multisite monitoring of different anatomical regions either concurrently or at predetermined time intervals. Monitoring anatomical changes during clinically relevant time periods or continuous monitoring provide an important diagnostic tool for detecting short or rapid changes in tissue structure, particularly interstitial layer thickness. In contrast to previous work, the invention is able to measure rapid changes in ILT and monitor ILT from different anatomical regions simultaneously or within short time frames to compare ILTs from different regions.

In one aspect, the invention provides for a method of multisite monitoring of ILT. The method comprises transmitting an ultrasound pulse from a first ultrasound probe to a first anatomical region and transmitting an ultrasound pulse from a second ultrasound probe to a second anatomical region. The method includes recording ultrasound signals from a first ultrasound probe to a first anatomical region and recording ultrasound signals from a second ultrasound probe to a second anatomical region. The method also includes monitoring interstitial layer thickness from the first and second, or more, anatomical regions. Typically, the method is practiced by monitoring from the first anatomical region concurrently with monitoring from the second anatomical region.

Another related aspect of the invention includes a multi-probe set that may be used for multi-site monitoring. The multi-probe set comprises a first ultrasound probe comprising a first output port, the first ultrasound probe adapted for continuous or in situ monitoring at a first anatomical region and a second ultrasound probe comprising a second output port, the second ultrasound probe adapted for continuous or in situ monitoring at a second anatomical region. The set can include an ultrasound system to concurrently process first signals from the first ultrasound probe and second signals from the second ultrasound probe. Systems or sets with more than two probes can also be used. Each probe in the set can be adapted for a particular anatomical region or indication. For example, the anatomical region can be selected from the group consisting of the forehead region, anterior tibia region, foot region, distal radius region, elbow region, presternal region and temporal bone region. Preferably, the ultrasound probe is a micro-transducer adapted for monitoring interstitial layer thickness.

The invention provides for the first time micro-transducers applied to the skin of a subject for ultrasound measurements of tissue structure. Typically, the micro-transducers are adapted for either monitoring ILT or capillary related edema, usually on the skin in a predetermined anatomical region. As described herein, the micro-transducers are typically small about 10 to 20 $mm^2$ or less in surface area, not hand-held but rather attachable to the skin surface, and light weight. Preferably, micro-transducers are isolated and not connected to an ultrasound system or display by a conductive wire, as described herein. In use, the micro-transducers are usually secured to the skin of a subject for continuous monitoring of the interrogated region.

BRIEF DESCRIPTION OF THE FIGURES

FIG. 1A shows normal leg tissue prior to an increase in capillary related interstitial layer thickness. Skin is "S". Tibia is "T". Fibula is "F". Muscle is "M" and interstitial layer is "IL". The probe interrogation site 100 is a preferred site for monitoring capillary related changes in ILT. The tissue plane 110 is approximately illustrated by the arrows. FIGS. 1B and C illustrate a small but progressive increase in ILT around 100 over time.

(dotted layer) and muscle or bone 210 (cross-hatched layer). FIGS. 2B and C illustrate that IL (wave-line layer) increases dramatically due to an increase in capillary related interstitial fluid.

DETAILED DESCRIPTION OF THE INVENTION

1.0 ABBREVIATIONS AND DEFINITIONS

Figure 1A:
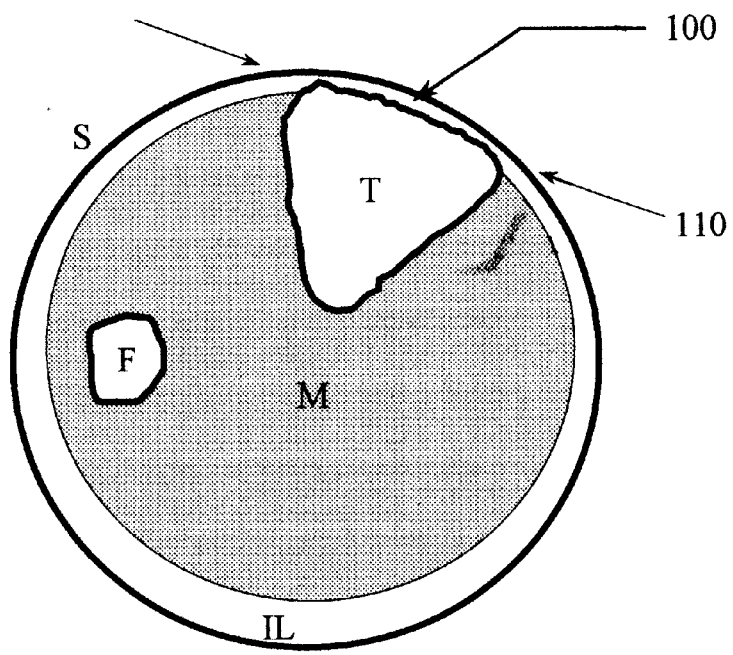
FIGS. 1A–C show an example of capillary related interstitial fluid accumulation.

ABBREVIATIONS include first reflective distance (FRD), interstitial fluid (IF), interstitial fluid content (IFC) interstitial fluid layer (IFL), interstitial fluid monitoring (IFM), interstitial layer thickness (ILT), interstitial fluid volume (IFV) and second reflective distance (SRD).

Acoustic communication refers to the passage of ultrasound waves between two points in a predetermined manner. Usually, this is accomplished by selecting a desired pathway between the two points that permits the passage of ultrasound waves either directly or indirectly. Direct passage of ultrasound waves would occur, for instance, when an ultrasound crystal is directly disposed to (usually touching) an acoustic coupling material, such as a composite. Indirect passage of ultrasound waves would occur, for instance, when an ultrasound crystal is located at a predetermined distance from an acoustic coupling material or when a number of acoustic coupling materials, often heterogenous materials, form two or more layers.

Acoustic coupler refers to a connection or plurality of connections between an ultrasound crystal and a substance that reflects or passes ultrasound pulses and is not part of the device. The acoustic coupler will permit passage of ultrasound waves. It is desirable for such couplers to minimize attenuation of ultrasound pulses or signals and to minimize changes in the physical properties of an ultrasound wave, such as wave amplitude, frequency, shape and wavelength. Typically, an ultrasound coupler will either comprise a gel or other substantially soft material, such as a pliable polymer matrix, that can transmit ultrasound pulses. Alternatively, an ultrasound sound coupler can be a substantially solid material, such as a polymer matrix, that can transmit ultrasound pulses. An ultrasound coupler is usually selected based on its acoustic impedance match between the object being interrogated and the ultrasound crystal(s). If a reflective surface is desired, for instance, as a spatial marker, a larger impedance difference is selected compared to situations where it is advantageous to minimize a reflective surface to avoid a sharp reflective surface.

Acoustic coupling material is a material that passes ultrasound waves, usually from a probe to a subject or tissue to be interrogated. It is usually not a living material and is most often a polymer or gel.

Anatomical region refers to a site on the surface of the skin, tumor, organ or other definable biomass that can be identified by an anatomical features or location. Usually, such a region will be definable according to standard medical reference methodology, such as that found in Williams et al., Gray's Anatomy, 1980.

Appendage region refers to a site on the surface of a limb of a subject. Examples of appendage regions include a variety of sites on a leg or an arm, such as a humeral or tibia region.

A-scan refers to an ultrasound technique where an ultrasound source transmits an ultrasound wave into an object, such as patient's body, and the amplitude of the returning echoes (signals) are recorded as a function of time. Only structures that lie along the direction of propagation are interrogated. As echoes return from interfaces within the object or tissue, the transducer crystal produces a voltage that is proportional to the echo intensity. The sequence of signal acquisition and processing of the A-scan data in a modem ultrasound instrument usually occurs in six major steps:

Detection of the echo (signal) occurs via mechanical deformation of the piezoelectric crystal and is converted to an electric signal having a small voltage.

Preamplification of the electronic signal from the crystal, into a more useful range of voltages is usually necessary to ensure appropriate signal processing.

Time Gain Compensation compensates for the attenuation of the ultrasound signal with time, which arises from travel distance. Time gain compensation may be user-adjustable and may be changed to meet the needs of the specific application. Usually, the ideal time gain compensation curve corrects the signal for the depth of the reflective boundary. Time gain compensation works by increasing the amplification factor of the signal as a function of time after the ultrasound pulse has been emitted. Thus, reflective boundaries having equal abilities to reflect ultrasound waves will have equal ultrasound signals, regardless of the depth of the boundary.

Compression of the time compensated signal can be accomplished using logarithmic amplification to reduce the large dynamic range (range of smallest to largest signals) of the echo amplitudes. Small signals are made larger and large signals are made smaller. This step provides a convenient scale for display of the amplitude variations on the limited gray scale range of a monitor.

Rectification, demodulation and envelope detection of the high frequency electronic signal permits the sampling and digitization of the echo amplitude free of variations induced by the sinusoidal nature of the waveform.

Rejection level adjustment sets the threshold of signal amplitudes that are permitted to enter a data storage, processing or display system. Rejection of lower signal amplitudes reduces noise levels from scattered ultrasound signals.

Blood refers to whole blood. Blood does not refer to red blood cell concentrates.

Blood flow refers to blood movement in a blood vessel (e.g., coronary, vein, artery, venole, arteriole, shunt, or capillary). Blood flow is usually associated with blood entering or leaving a tissue or definable anatomical region, such as an appendage or a specific vessel (e.g., artery, vein, naturally occurring and non-naturally occurring shunt, or coronary).

B-scan refers to an ultrasound technique where the amplitude of the detected returning echo is recorded as a function of the transmission time, the relative location of the detector in the probe and the signal amplitude. This is often represented by the brightness of a visual element, such as a pixel, in a two-dimensional image. The position of the pixel along the y-axis represents the depth, i.e. half the time for the echo to return to the transducer (for one half of the distance traveled). The position along the x-axis represents the location of the returning echoes relative to the long axis of the transducer, i.e. the location of the pixel either in a supero-inferior or mediolateral direction or a combination of both. The display of multiple adjacent scan lines creates a composite two-dimensional image that portrays the general contour of internal organs.

Cardiac performance refers to at least one physical functioning property of the heart at rest, such as an EKG, ST segment, QRS wave, estimated cardiac output, estimated contractility, afterload or preload. Dynamic cardiac performance refers to at least one physical functioning property of the heart during a physiological challenge, such as physical exercise (e.g. predetermined physical exercise or uncontrolled exercise), mental stress, medical treatment or diagnostic maneuvers (e.g. breath holding).

Chip refers to any current and future electronic hardware device within a computational unit that can be used as an aid in controlling the components of an ultrasound unit including: 1) timing and synchronizing trigger pulses and subsequent transmission of ultrasound waves, 2) measuring and analyzing incoming ultrasound signals, 3) determining the shortest reflective distance generated from ultrasound signals reflected from multiple different ultrasound waves emitted at different transmission angles, 4) estimating body fat and edema using various equations, 5) measuring various anatomic landmarks, 6) comparing data to predetermined standards and data cut-offs (e.g. electronic filtering), and 7) performing multiple other simple and complex calculations.

Clinically relevant time period refers to a period of time when changes in physiology are expected or detected. Such periods can be on the order of seconds (e.g., 5 to 300 seconds or less) for rapid physiological changes, such as changing position from sitting to standing; minutes (e.g. about 2 to 40 minutes or less) for relatively rapid physiological changes, such as shock or inflammation; and hours to days (e.g. about 0.5 to 4 hours or about 0.5 days to 1 week or more) for slow physiological changes, such as altitude acclimation, long term medical treatment that might require weeks or months to detect a change, and diet acclimation.

Computational unit refers to any current or future software, chip or other device used for calculations, such as reflective distance calculations, now developed or developed in the future. The computational unit is capable of determining the shortest reflective distance when two or more ultrasound sources are employed at different transmission angles. The computational unit may also be used for controlling the ultrasound generator or source, for defining or varying the firing rate and pulse repetition rate (as well as other parameters related to the ultrasound generator or source), for measuring the reflected signal, for image reconstruction in B-scan mode and for filtering and thresholding of the ultrasound signal. Other applications of the computational unit to the methods and devices described herein will be recognized by those skilled in the art. The computational unit may be used for any other application related to this technology that may be facilitated with use of computer software or hardware.

Crystal refers to the material used in the ultrasound transducer to transmit ultrasound waves and includes any current and future material used for this purpose. Crystals typically consist of lead zirconate titanate, barium lead titanate, lead metaniobate, lithium sulfate and polyvinylidene fluoride or a combination thereof. A crystal is typically a piezoelectric material, but any material that will contract and expand when an external voltage is applied can be used, if such a material can generate ultrasound waves described herein and known in the art. Crystals emit ultrasound waves because the rapid mechanical contraction and expansion of the material moves the medium to generate ultrasound waves. Conversely, when incoming ultrasound waves deform the crystal, a current is induced in the material. The materials them emits an electrical discharge that can be measured and, ultimately, with B-scan technology be used to reconstruct an image. Crystals or combinations of crystals with dipoles that approximate the acoustic impedance of human tissue are preferred, so as to reduce the impedance mismatch at the tissue/probe interface.

C-scan refers to an ultrasound technique where additional gating electronics are incorporated into a B-scan to eliminate interference from underlying or overlying structures by scanning at a constant-depth. An interface reflects part of the ultrasound beam energy. All interfaces along the scan line may contribute to the measurement. The gating electronics of the C-mode rejects all returning echoes except those received during a specified time interval. Thus, only scan data obtained from a specific depth range are recorded. Induced signals outside the allowed period are not amplified and, thus, are not processed and displayed. C-mode-like methods are also described herein for A-scan techniques and devices in order to reduce the probe/skin interface reflection.

Detector refers to any structure capable of measuring an ultrasound wave or pulse, currently known or developed in the future. Crystals containing dipoles are typically used to measure ultrasound waves. Crystals, such as piezoelectric crystals, shift in dipole orientation in response to an applied electric current. If the applied electric current fluctuates, the crystals vibrate to cause an ultrasound wave in a medium. Conversely, crystals vibrate in response to an ultrasound wave that mechanically deforms the crystals, which changes dipole alignment within the crystal. This, in turn, changes the charge distribution to generate an electric current across a crystals surface. Electrodes connected to electronic circuitry sense a potential difference across the crystal in relation to the incident mechanical pressure.

Echogenicity refers to the brightness of a tissue in an ultrasound image relative to the adjacent tissues, typically on a B-scan image. Echogenicity is dependent on the amount of ultrasound waves reflected by the tissue. Certain tissues are more echogenic than other tissues. Fatty tissue, for example, is more echogenic than muscle tissue. For identical imaging parameters, fatty tissue will thus appear brighter than muscle tissue. Consequently, image brightness can be used to identify different tissues.

Grip refers to a portion of a probe that is grasped by an operator. As described herein, most grip designs permit a human to self measure anatomical regions that are normally difficult to accurately interrogate using a handheld probe designed to be operated by a person that is not the subject.

Heart failure refers to the pathophysiologic state in which an abnormality of cardiac function is responsible for the failure of the heart to pump blood at a rate commensurate with the requirements of the metabolizing tissues and/or in which the heart can do so only from an abnormally high filling pressure. Compensated heart failure refers to a condition in which the heart functions at an altered, but stable physiologic state, e.g. at a different but stable point on the Frank-Starling-curve through an increase in preload or after development of myocardial hypertrophy. Decompensated heart failure refers to a condition in which the heart functions at an altered and unstable physiologic state in which cardiac function and related or dependent physiologic functions deteriorate progressively, slowly or rapidly. Compensated or decompensated heart failure can result in multiple complications, such as progressive increase in capillary related edema, progressive renal failure, or progressive ischemic tissue damage.

Linear array refers to a transducer design where the crystals are arranged in a linear fashion along one or more axes. Crystals can be fired in sequential, as well as non-sequential and simultaneous firing patterns or a combination thereof With sequential firing, each crystal can produce an ultrasound beam and receive a returning echo for data collection. The number of crystals in one array usually determines the number of lines of sight for each recording. With segmental firing, a group or segment of crystals can be activated simultaneously resulting in a deeper near field and a less divergent far field compared with sequential activation. A segmental linear array produces, however, a smaller number of lines of sight when compared to a sequential linear array with the same number of crystals.

Lymphedema refers to a condition that can be congenital or acquired and is characterized by abnormal lymphatic drainage from damage to, or obstruction of, the lymph vessels. Causes of secondary lymphedema, include bacterial lymphangitis, surgery, radiation, and trauma. Unlike capillary related edema, which can develop within minutes or few hours, lymphedema develops slowly over days and months. In chronic stages of lymphedema, the affected body part has a woody texture and the tissues become fibrotic and indurated.

Mechanically connected refers to a connection between two or more mechanical components, such as an ultrasound source having at least two transmission positions. A mechanical connection between two transmission positions may be accomplished using a mechanical motor to rotate or move an ultrasound source. Optionally, the ultrasound source can be rotated or moved on a track.

Mechanical motor refers to any device that can move the ultrasound source from a first to a second position and, if desired, to additional positions. A mechanical motor may employ a spring-like mechanism to move the ultrasound source from said first to said second position. A mechanical motor may also employ a hydraulic, a magnetic, an electromagnetic mechanism or any other current and future mechanism that is capable of moving the ultrasound source from a first to a second position.

Medical condition refers to a physiological state of a subject, usually a human, that is not normal and would usually benefit from, or require, medical treatment. Such states may arise from a variety of conditions, including diseases, physiological challenges, trauma, infection, stress, drug abuse, and accelerated aging.

Medical treatment refers to an action intended to confer a medical or physiological benefit on a subject, including surgery, catheterization, drug administration (e.g. either by the subject or by a health care worker), exercise, diet and non-invasive medical techniques (e.g. ultrasound and intravenous administration of electrolytes or osmotically active substances).

Myxedema refers to an infiltrative lesion of the skin of the pretibial area. Myxedema can occur in patients with autoimmune thyroid disease, such as Graves' disease. Unlike capillary related edema, pretibial myxedema results from deposition of mucin in the dermis. Myxedema develops slowly over months and years. The affected area is demarcated from normal skin by the fact that it is raised, thickened, and may be pruritic and hyperpigmented. The lesions are usually discrete assuming a plaque-like or nodular configuration.

Non-orthogonal probe alignment refers to alignment of the probe at an angle other than 90 degrees relative to the object or tissue plane to be measured, such as the probe/skin interface or the subcutaneous fat/muscle interface.

Parallax adjustment refers to a correction of distance measurements for probe mis-alignment. Parallax will result when the ultrasound transducer is placed on the skin in a non-orthogonal orientation thereby creating a transmission angle smaller or greater than 90 degrees. As the difference between the ideal transmission angle of 90 degrees, i.e. perpendicular probe alignment, and the actual transmission angle increases, the ultrasound beam has to travel along an increasingly longer path through the object thereby artifactually overestimating the actual object or tissue layer thickness. A parallax adjustment, i.e. a correction of artifactually elongated distance measurements can, however, be obtained by transmitting multiple ultrasound waves at different transmission angles. The ultrasound wave that has the transmission angle that is closest to 90 degrees will yield the smallest parallax error and therefore provide the best parallax adjustment.

Plane refers to the surface of a cross-sectional area of tissue interrogated by an ultrasound probe. In ultrasound, the portion of the tissue included in the measurement or image is more accurately referred to as a volume. The x-dimension of this volume reflects the length of the tissue plane, i.e. the length of imaged tissue. The x-dimension typically varies between 1 and 10 cm or more. The y-dimension reflects tissue depth from the plane, e.g. the distance from the skin surface to a reflection point in the tissue. The y-dimension (or depth of the interrogation) depends, among other things, on the type of transducer, the type of tissue, and the frequency with which the ultrasound beam is transmitted. With higher frequencies, tissue penetration decreases and the maximum depth from the tissue plane will decrease. The y-dimension typically varies between 1 and 30 cm. The z-dimension corresponds to the width of the plane that is interrogated. It typically varies between 1 and 15–20 mm.

Potential fluid space refers to a compartment of the body that may fill with fluid, including blood, under certain conditions. Such conditions include medical conditions, such as trauma, blood vessel breakdown (e.g., partial or complete), breakdown (e.g., partial or complete) of epithelium and infection. Potential fluid spaces include the subarachnoid, subdural, epidural, mediastinal, perinephric, peritoneal or pleural spaces.

Self measurement refers to the ability of a subject to monitor or measure a portion of a subject's body, preferably in real time.

Shortest reflective distance refers to the shortest distance between the surface of an ultrasound transducer and a particular layer interface in a object, such as a transducer and a subjacent tissue interface that can be measured with ultrasound. The shortest reflective distance represents the best approximation of the distance measured by ultrasound of the true anatomic distance between the surface of a transducer and a subjacent tissue interface, such as the fat/muscle interface. Skin thickness can also be measured or estimated and subtracted from the shortest reflective distance to calculate the fat layer thickness, as described herein. The shortest reflective distance can be measured when an ultrasound transducer is oriented to the tissue interface in an orthogonal fashion. The reflective distance can be calculated as:

$$RD = SOS \times t/2, \qquad [\text{Eq. 1}]$$

where RD is the reflective distance, SOS is the speed of sound in a given medium and t is the time interval between transmission of the ultrasound wave and return of the signal to the transducer. The shortest reflective distance can be determined by selecting the appropriate RD as described herein.

The shortest reflective distance can be determined by using at least two or preferably multiple ultrasound pulses, where an ultrasound source provides a pulse at a predefined transmission angle. Transmission angles from an ultrasound source typically differ by at least 1 degree. Reflective distances between an ultrasound source and the tissue interface in question will be measured using the formulae described herein or developed in the art. The ultrasound source that has the transmission angle that is closest to 90 degrees will usually yield the smallest value for reflective distance. This value is least affected by parallax between the probe and the tissue interface and is referred to as shortest reflective distance. Calculation of shortest reflective distance refers to electronic or mathematical determination of the shortest reflective distance using the methods described herein. Reflective distance will be calculated for ultrasound waves obtained at various transmission angles. A computational unit can then determine which wave yielded the smallest RD value in order to select the shortest reflective distance.

Skin refers to the external tissue layer in humans and animals consisting of epidermis and dermis.

Skin Related Definitions:

Epidermis refers to the outer, protective, nonvascular layer of the skin of vertebrates, covering the dermis. The epidermis consists histologically of five layers, i.e. the stratum corneum, the stratum lucidum, the stratum granulosum, the stratum spinosum, and the stratum basale.

Dermis refers to the sensitive connective tissue layer of the skin located below the epidermis, containing nerve endings, sweat and sebaceous glands, and blood and lymph vessels. Histologically, the dermis consists of a papillary layer and a reticular layer. The papillary layer contains the vessels and nerve endings supplying the epidermis. The reticular consists predominantly of elastic fibers and collagen.

Subcutaneous tissue layer refers to a tissue layer located below the skin. This tissue layer is typically characterized by a loose meshwork of connective tissue such as collagen and elastic fibers. It is rich in small vessels, e.g., arterioles and venoles, and capillaries. In edematous states, the subcutaneous tissue layer can expand extensively. Edema will expand the space between the cells and may also result in diffuse swelling of the cells. Owing to its loose cellular network and abundant amount of capillaries, the subcutaneous tissue layer is often the first or one of the first locations affected by early, developing edema. The relative amount of the different tissues will vary depending on the anatomic location. In the anterior tibial region, for example, connective tissue predominates, while in the abdominal or buttocks region adipose tissue will predominate. If it is desired to quantitatively measure interstitial layer thickness, it is preferable to select sites that contain predominantly connective tissue and vessels, since these sites can potentially change more rapidly or and expand to a greater extent than sites predominantly containing adipose tissue.

Tibia Related Definitions:

Anterior aspect of the tibia refers to the surface of the tibia facing in anterior direction. The cross-section of the tibia is triangular with an anteriorly, a laterally, and a posteriorly facing surface. The laterally and posteriorly facing surfaces are covered by several centimeters of muscle tissue. The anterior surface of the tibia, however, is only covered by skin and, in healthy, non-edematous subjects, a thin subcutaneous tissue layer. This subcutaneous tissue layer can enlarge extensively in subjects with capillary related edema. Since there is no interposed muscle layer, the thickness of the subcutaneous tissue/edema layer can be assessed clinically in this location by compressing the tissue against the underlying bone. Cortical bone at the anterior aspect of the tibia is also a strong ultrasound reflector demonstrating a sharply defined reflective interface in the ultrasound image thereby facilitating measurements of the thickness of the subcutaneous tissue/edema layer.

Proximal third of the tibia refers to a measurement site at the anterior aspect of the upper tibia. The medial knee joint space and the medial malleolus are localized by manual palpation. The distance between the medial knee joint space and the medial malleolus is measured with a tape measure and subdivided into three equidistant portions, upper, middle, and lower. Alternatively, the distance between the lateral knee joint space and the lateral malleolus can be measured and subdivided into three equidistant portions. The border between the midportion and the upper portion defines the proximal third of the tibia site.

Mid-tibia refers to a measurement site at the anterior aspect of the tibia halfway between the medial knee joint space and the medial malleolus or, alternatively, the lateral knee joint space and the lateral malleolus.

Distal third of the tibia refers to a measurement site at the anterior aspect of the lower tibia. The border between the midportion, as measured above (see "proximal third of the tibia"), and the lower portion defines the distal third of the tibia site.

Lateral malleolus refers to a bony protuberance at the lateral aspect of the ankle joint. The lateral malleolus is formed by the fibula and represents the lateral portion of the ankle mortise.

Medial malleolus refers to a bony protuberance at the medial aspect of the ankle joint. The medial malleolus is formed by the tibia and represents the medial portion of the ankle mortise.

Therapeutic agent refers to an active substance or collection of active substances that produce a beneficial effect in a subject when administered in a therapeutically effective amount using a therapeutically effective modality. Such agents include active substances directed to specific physiological processes or systems, such as, but not limited to, diuretic, hepatic, pulmonary, vascular, muscular, cardiac or diabetic agents. Usually, such agents will modify the physiological performance of a target tissue or cell in order to shift the physiological performance of the target tissue or cell towards a more homeostatic physiological state.

Therapeutic kit refers to a collection of components that can be used in a medical treatment.

Therapeutic dosage refers to a dosage considered to be sufficient to produce an intended effect.

Therapeutically effective modality refers to a manner in which a medical treatment is performed and is considered to be sufficient to produce an intended effect.

Tissue Related Definitions:

Fat/fascia interface refers to the border between the proximal surface of the subcutaneous fat tissue layer and a potential distal surface of the fascial tissue layer.

Fat/muscle interface refers to the border between the proximal surface of the subcutaneous fat tissue layer and the distal surface of the muscle tissue layer.

Inner border of subcutaneous fat tissue refers to the interface between the subcutaneous fat and the subjacent muscle, if present, or the interface between the subcutaneous fat and the subjacent fascia, if present.

Muscle/bone interface refers to the border between the proximal surface of the muscle tissue layer and the distal surface of the subjacent layer of bone, e.g. the femur in the thigh, the tibia or fibula in the calf, the humerus in the upper arm, or the radius or ulna in the forearm.

Muscle/internal organ interface refers to the border between the proximal surface of the muscle tissue layer and the adjacent distal surface of the internal organs.

Outer border of subcutaneous fat tissue refers to the interface between the patient's skin and the subcutaneous fat.

Skin/fat interface refers to the border between the proximal surface of the skin layer and the distal surface of the subcutaneous fat tissue layer.

Tissue refers to an organized biomaterial usually composed of cells. For dietary purposes, a distinction is made between fatty tissue and lean tissue. Fatty tissue is composed of adipose cells, while lean tissue includes all other tissues except for bone.

Tissue volume may contain several different layers of tissue, such as skin, subcutaneous fat, fascia, muscle, bone, internal organs and other tissues. Ideally, an ultrasound generator is oriented in an orthogonal fashion relative to the interrogated tissue. However, when an ultrasound generator is oriented to the skin in a non-orthogonal fashion, i.e. when the transmission angle is less than 90 degrees, a parallax can result that will artifactually increase the apparent thickness of the interrogated tissue layers.

Tissue Swelling Related Definitions:

Edema refers to a pathologic accumulation of fluid within or between body tissues. Edema fluid can accumulate in potential fluid spaces, e.g. the pleural space, the pericardial space, and the intraperitoneal space. Edema fluid can accumulate in the interstitial space (e.g., in extracellular location) between tissue cells thereby expanding the interstitial space. Edema fluid can also accumulate within the cells, i.e. in an intracellular location (e.g., in toxic, metabolic, infectious, inflammatory, and autoimmune disorders). Causes of edema include but are not limited to impairment of vascular, cardiac, renal, and hepatic function, neurologic disorders, metabolic disorders, trauma, burns, tissue damage, changes in intravascular and intracellular colloid osmotic pressure, overhydration, e.g. in transfusion therapy or parenteral nutrition, exposure to toxic substance, e.g. inhalational or by ingestion, and drugs (see also Tables 3 and 4).

Capillary related edema refers to an abnormal fluid imbalance arising from capillaries and leading to abnormal local fluid retention. Capillary related edema results from an abnormal physiological function or physiological challenge to the venous system, arterial system, cardiovascular system, renal system, hepatic system, pulmonary system or other non-circulatory, internal organ systems normally involved in homeostasis of normal fluid retention. The present invention is particularly applicable to the systemic aspects of capillary related edema. For clarity, capillary related edema does not refer to pretibial myxedema, which is a lesion in the dermis that leads to tissue swelling. Pretibial myxedema is associated with abnormal mucin production in the dermis that disrupts the surrounding tissue. Any water associated with mucin that might be considered related to pretibial myxedema is not considered capillary related edema, as mucin is an extracellular protein, which in pretibial myxedema, is not considered to be associated with an internal organ system normally involved in homostasis of normal fluid retention. For further clarity, capillary related edema does not refer to tissue swelling associated with the lymph system. Venous or arterial systems do not refer to the lymphatic system. Potential capillary related edema layer refers to an anatomical region where capillary related edema might occur.

Edema detection refers to the determination of abnormal fluid retention in a subject or a subject's tissue. In many instances edema detection can occur without detecting or knowing the underlying cases of the edema. Often edema detection will lead to additional tests to determine the cause or cause of the edema. For clarity, edema detection does not refer to detection of tissue swelling primarily associated with pretibial myxedema or a malfunctioning of the lymphatic system.

Capillary related interstitial fluid refers to fluid between internal tissues of the body that is on the outside of cells and arising from capillaries. Usually, this fluid is subcutaneous, which makes it easier to examine. Capillary related interstitial fluid, however, may also be found in any tissue or layer, unless otherwise indicated herein. Capillary related interstitial fluid is usually comprised of water, body salts and extracellular biomolecules, such as proteins or sugars. Intracellular biomolecules may be found in capillary related interstitial fluid, especially adjacent to traumatized or compromised tissue. For clarity, capillary related interstitial fluid does not refer to 1) blood in either blood vessels or blood released in a potential fluid space of the body (e.g., the subarachnoid, subdural, epidural, or pleural space) by a traumatic, abrupt or accidental lesion (including an aneurysm) of a blood vessel, 2) ascites in the intraperitoneal cavity, 3) fluid in the pleural space (e.g., pleural effusion), 4) fluid in the fetus, 5) fluid in the dermis, 6) fluid in the mouth and 7) fluid, usually blood or pericardial effusion, in the pericardium.

Interstitial fluid content (IFC) refers to an amount of interstitial fluid in a given anatomical region. IFC can be expressed as $mm^2$ when derived as the measured thickness of the interstitial fluid layer and multiplied by length of the area interrogated. IFC can be used to estimate total size of an interstitial fluid layer or interstitial fluid volume.

Interstitial fluid layer (IFL) refers to layer of interstitial fluid that forms a stratum either within or around an internal tissue. Often such layers substantially circumscribe a tissue, especially a tissue of an appendage or an organ. Such layers can also be localized and appear as pockets or lakes of fluid apposite or interpersed in a tissue. For clarity, IFL does not refer to a stratum formed by pretibial myxedema, which is a lesion in the dermis that leads to tissue swelling. Pretibial myxedema is associated with abnormal mucin production in the dermis that disrupts the surrounding tissue.

Interstitial fluid volume (IFV) refers to a volume of interstitial fluid in a subject or a tissue. Usually this term is used in reference to the IFV of an entire human, which may change in response to various physiological challenges, such as medical conditions or treatments. The methods and devices described herein can assess IFV qualitatively both on the level of the entire subject or a portion thereof, such as a tissue. The methods and devices described herein can also measure IFV quantitatively both on the level of the entire subject (indirect measurement by estimate as described herein) or a portion thereof, such as a tissue (indirect or direct measurement depending on the tissue).

Transmission angle refers to the angle of an ultrasound beam that intersects the object or tissue plane. The transmission angle is normally measured with respect to the object or tissue plane. The object or tissue plane has a reference angle of zero degrees.

For example, as the transmission angle increases toward 90 degrees relative to the tissue plane, the ultrasound beam approaches an orthogonal position relative to the tissue plane. Preferably, ultrasound measurements of the fat/muscle or fat/bone interface are performed when the ultrasound beam is orthogonal to the plane of the tissue. Operator error, however, often leads to a parallax between the object or tissue plane and the probe. Tissue/probe parallax most often occurs when an operator fails to place the outer probe surface parallel to the tissue plane. Thus, the operator inadvertently creates a transmission angle less than ninety degrees with respect to the tissue plane, i.e. not orthogonal to the tissue plane, that skews the ultrasound beam and the return signal. The resultant skewing creates a parallax when using an ultrasound beam to measure tissue thickness, such as subcutaneous fat thickness or any other thickness measurement of a layer in an object.

Non-orthogonal ultrasound beam transmission creates an apparent displacement of the ultrasound beam compared to an ultrasound beam transmitted at 90 degrees with respect to the tissue plane. The return signal, which is a fraction of an ultrasound beam that is reflected at a tissue interface, travels through the tissue along a longer distance when returning back to the ultrasound detector compared to a return signal that originated from a beam transmitted orthogonal to the tissue plane. To increase the accuracy of the measurement of tissue thickness, preferably the transmission angle is between 90 to 60 degrees, more preferably 90 to 80 degrees. Lower transmission angles can be used, as low as 1 degree, but are not preferred due to the large error associated with the distance measurements of the fat/muscle or fat/bone interface. Such errors can be compensated for by techniques previously described, U.S. patent application Ser. No. 08/731,821, filed Oct. 21, 1996 (Lang et al).

Transmission frequency refers to the frequency of the ultrasound wave that is being transmitted from the ultrasound source. Transmission frequency typically ranges between 0.2 MHz and 25 MHz. Higher frequencies usually provide higher spatial resolution. Tissue penetration decreases with higher frequencies, especially in dense fat tissue. Lower transmission frequencies are generally characterized by lower spatial resolution with improved tissue penetration. Methods and devices for optimizing and matching transmission frequencies to the measured object's acoustic properties are described herein.

Vascular performance refers to the ability of a blood vessel to conduct blood away from or towards the heart.

Venous performance refers to the ability of a venous vessel (e.g., a vein) to return blood towards the heart.

Ultrasound pulse refers to any ultrasound wave transmitted by an ultrasound source. Typically, the pulse will have a predetermined amplitude, frequency, and wave shape. Ultrasound pulses may range in frequency between 20 kHz and 20 Mhz or higher. Preferably, for ILT measurements pulses range from 2.5 Mhz to 25 Mhz and more preferably from 3.5 to 10 Mhz. Ultrasound pulses may consist of sine waves with single frequency or varying frequencies, as well as single amplitudes and varying amplitudes. In addition to sine waves, square waves or any other wave pattern may be employed. Square waves may be obtained by adding single-frequency sine waves to other sine waves. The summation of waves can then result in a square wave pattern.

Ultrasound signal refers to any ultrasound wave measured by an ultrasound detector after it has been reflected from the interface of an object or tissue. Ultrasound signals may range in frequency between 20 kHz and 20 Mhz or higher. Preferably, for ILT measurements signals range from 2.5 Mhz to 25 Mhz.

Ultrasound source refers to any structure capable of generating an ultrasound wave or pulse, currently known or developed in the future. Crystals containing dipoles are typically used to generate an ultrasound wave above 20 khz. Crystals, such as piezoelectric crystals, that vibrate in response to an electric current applied to the crystal can be used as an ultrasound source. As referred to herein, an ultrasound source usually has a particular transmission angle associated with it. Consequently, a single ultrasound generator, as defined herein, can be used at different transmission angles to form more than one ultrasound pulse at different transmission angles. An ultrasound generator can include single or multiple ultrasound sources that can be arranged at different angles to produce ultrasound beams (or pulses) with variable transmission angles. In some ultrasound generators, multiple ultrasound sources may be arranged in a linear fashion. This arrangement of ultrasound sources is also referred to as a linear array. With linear arrays, ultrasound sources are typically fired sequentially, although simultaneous firing of groups of adjacent ultrasound sources or other firing patterns of individual or groups of ultrasound sources with various time delays can be achieved as described herein or developed in the art. The time delay between individual or group firings can be used to vary the depth of the beam in an object.

Ultrasound transmission parallax refers to an error in the measurement of distances between two distinct layers in an object, such as tissue, resulting from non-orthogonal probe placement. Ideally, the probe is oriented orthogonal to the object or tissue to be measured. In this fashion, the distance between two tissue layers measured on the ultrasound will more accurately reflect the true anatomic distance. However, if the probe is applied to the skin at an angle smaller or greater than 90 degrees, artifactual elongation of all measured distances will result. The difference between the distance measured with ultrasound and the true anatomic distance at the point where the probe is placed will increase the more the probe-to-skin angle differs from 90 degrees.

Generally, tissue thickness, especially capillary related interstitial fluid layer, can be measured using more than one ultrasound source (e.g. at least a first and second ultrasound source) to permit multiple transmission angles or one ultrasound source positioned at different transmission angles. The use of multiple transmission angles facilitates the determination of the shortest reflective distance. If only one transmission angle is used to calculate the shortest reflective distance, the shortest reflective distance could have a considerable ultrasound transmission parallax error associated with it.

Ultrasound wave refers to either an ultrasound signal or pulse.

2.0 INTRODUCTION

The present invention recognizes for the first time that ultrasound can be applied to the convenient and cost effective measurement of capillary related interstitial fluid. The invention includes continuous or intermittent monitoring of capillary related interstitial fluid in a subject, such as capillary related edema assessment in a human, using ultrasound wave devices and methods as described herein for the embodiments of the invention. Previously, it was not recognized that diagnostic ultrasound measurements of capillary related interstitial fluid were possible or precise. Nor was it recognized that clinically rapid shifts in capillary related interstitial fluid distribution in tissues could be monitored using ultrasound methods or devices. Previous work also failed to recognize that capillary related interstitial fluid layers in a tissue could be monitored over time and, if desired, accurately quantitated, as described herein. The inventors were also the first to recognize that ultrasound methods and devices could be applied to the assessment of different aspects of integrated cardiovascular function, including venous performance and dynamic cardiac performance. Nor was it previously recognized that ultrasound devices dedicated to measurement of capillary related interstitial fluid, particularly autonomous hand-held devices for self-measurement of capillary related edema, could accurately determine capillary related interstitial fluid status, as described herein. It was also not previously recognized that ultrasound devices dedicated to continuous monitoring of interstitial fluid, particularly autonomous hand-held devices for self-measurement of capillary related edema or small remote probes located on the subject, could accurately determine interstitial fluid status, as described herein.

By way of introduction, and not limitation of the various embodiments of the invention, the invention includes at least eight general aspects:

1) an ultrasonic method of measuring capillary related interstitial fluid, including capillary related interstitial fluid layer thickness in a subject, particularly a capillary related edema layer, by determining the distance between reflective surfaces (e.g., bone or fat) and skin with ultrasound, 2) an ultrasonic method of detecting capillary related edema by determining the distance between the reflective surfaces of bone and skin at predetermined anatomical sites with ultrasound, 3) an ultrasonic method of assessing vascular performance by clinically challenging or enhancing vascular performance and measuring capillary related interstitial fluid in a tissue that is clinically relevant to either the challenge or enhancement of vascular performance with ultrasound, 4) an ultrasonic method of assessing cardiac performance by clinically challenging or enhancing cardiac performance and measuring capillary related interstitial fluid in a tissue that is clinically relevant to either the challenge or enhancement of cardiac performance with ultrasound, 5) an ultrasonic method of detecting capillary related interstitial fluid volumes in humans by measuring capillary related interstitial fluid in a tissue with ultrasound prior to, before or concurrent with a medical condition or treatment, 6) a hand-held ultrasound device for measuring capillary related edema that is optionally capable of self-measurement, 7) a dedicated ultrasound system for measuring interstitial fluid, and 8) an ultrasound probe for in situ ultrasound monitoring, particularly of interstitial fluid layers.

These aspects of the invention, as well as others described herein, can be achieved using the methods and devices described herein. To gain a full appreciation of the scope of the invention, it will be further recognized that various aspects of the invention can be combined to make desirable embodiments of the invention. For example, the invention includes an interstitial fluid monitor (IFM) that can desirably include characteristics of aspects (1), (2), (3) and (8) to create a system for periodic or continuous monitoring of patient interstitial fluid. Such combinations result in particularly useful and robust embodiments of the invention.

3.0 METHODS AND DEVICES FOR MEASURING CAPILLARY RELATED INTERSTITIAL FLUID

Multicellular, living organisms with more than one body compartment tightly regulate the interstitial fluid that baths their cells. Such organisms manage their interstitial fluid using a variety of physiological mechanisms that can include adjusting excretory, secretory, and circulatory processes. These physiological processes, as well as others, have evolved to compensate for small and rapid changes in capillary related interstitial fluid that can dramatically alter homeostasis due to physiological challenges and responses.

The invention recognizes for the first time that capillary related interstitial fluid can be assessed with ultrasound techniques by interrogating a tissue of interest and measuring distances between reflective interfaces within the tissue of interest that anatomically correspond to capillary related interstitial fluid or capillary related interstitial fluid layers. Because interfaces between different biological layers arise due to differences in the relative amounts of water and biomaterials in such layers, the ultrasound methods and devices described herein can advantageously utilize such differences to qualitatively or quantitatively measure capillary related interstitial fluid in the tissue of interest.

The invention's methods and devices are broadly applicable to any tissue, including internal organs, having one or more reflective interface(s) that can be interrogated using ultrasound. Usually, such interfaces will arise from differences in water or biomaterial content, such as interfaces between bone and muscle layer, skin layer and fat layer, cell mass and interstitium, tumor and interstitium, or bone and interstitial layer. Consequently, the present invention finds broad application in a variety of settings in health care and health management.

Figure 1B:
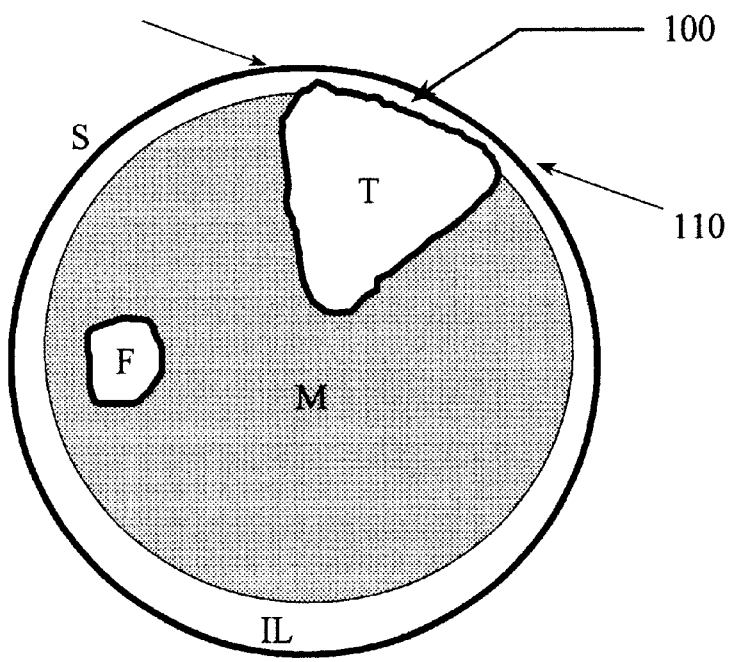
Figure 1C:
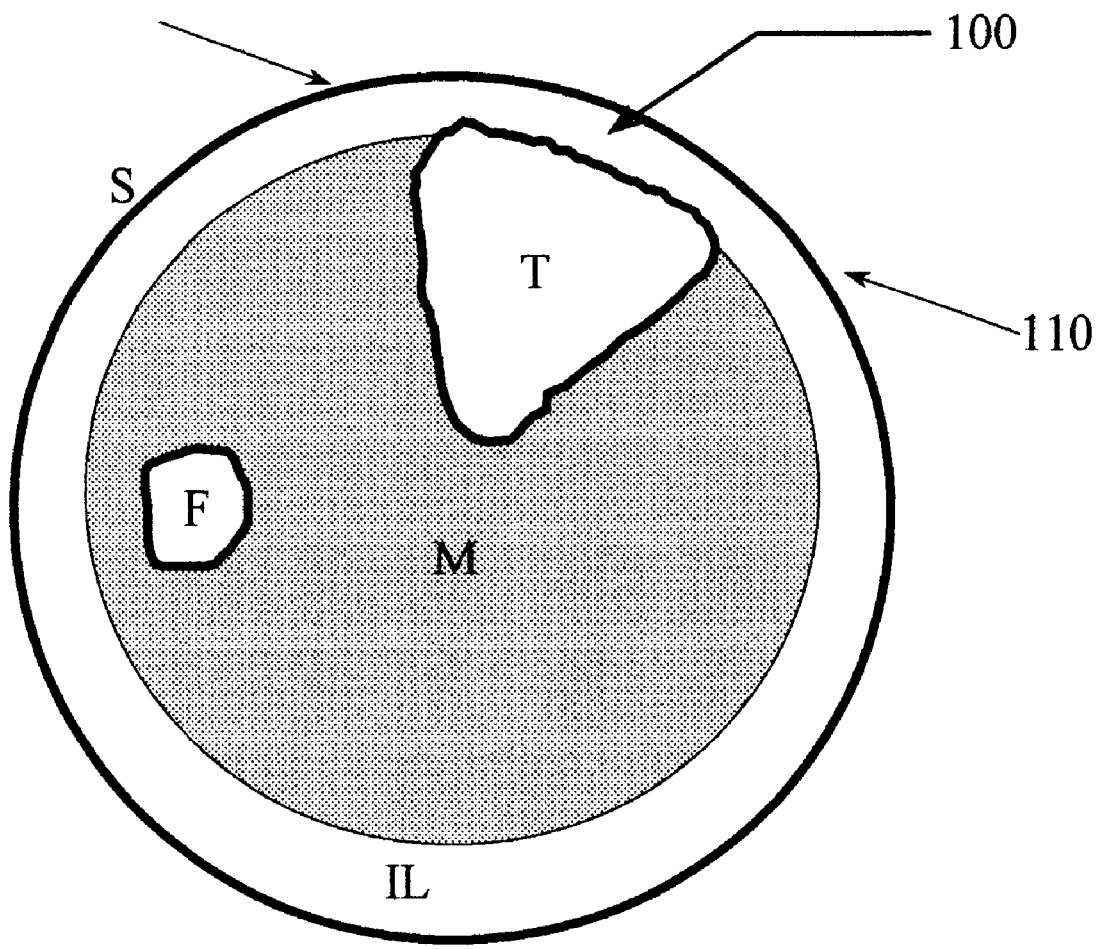

By way of example, and not limitation, FIGS. 1A–C illustrates capillary related interstitial fluid accumulation. FIG. 1A shows normal leg tissue prior to an increase capillary related interstitial layer thickness. Skin is "S." Tibia is "T." Fibula is "F." Muscle is "M" and interstitial layer is "L." The probe interrogation site 100 is a preferred site for monitoring capillary related changes in ILT. The tissue plane 110 is approximately illustrated by arrows. FIGS. 1B and C illustrate a small but progressive increase in ILT around 100 over time. Such changes in ILT can be measured using the devices and methods of the present invention.

Figure 2A:
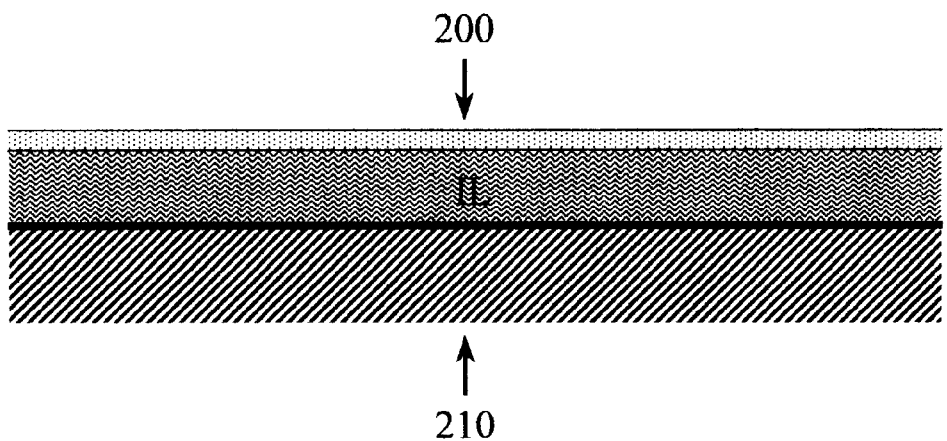
FIGS. 2A–C shows a magnified view of probe interrogation site 100 from FIG. 1. IL is located between skin 200
Figure 2B:
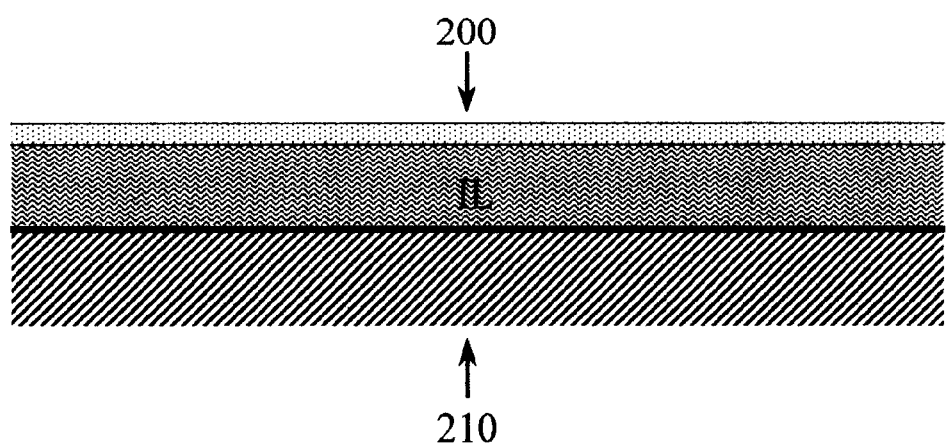
Figure 2C:
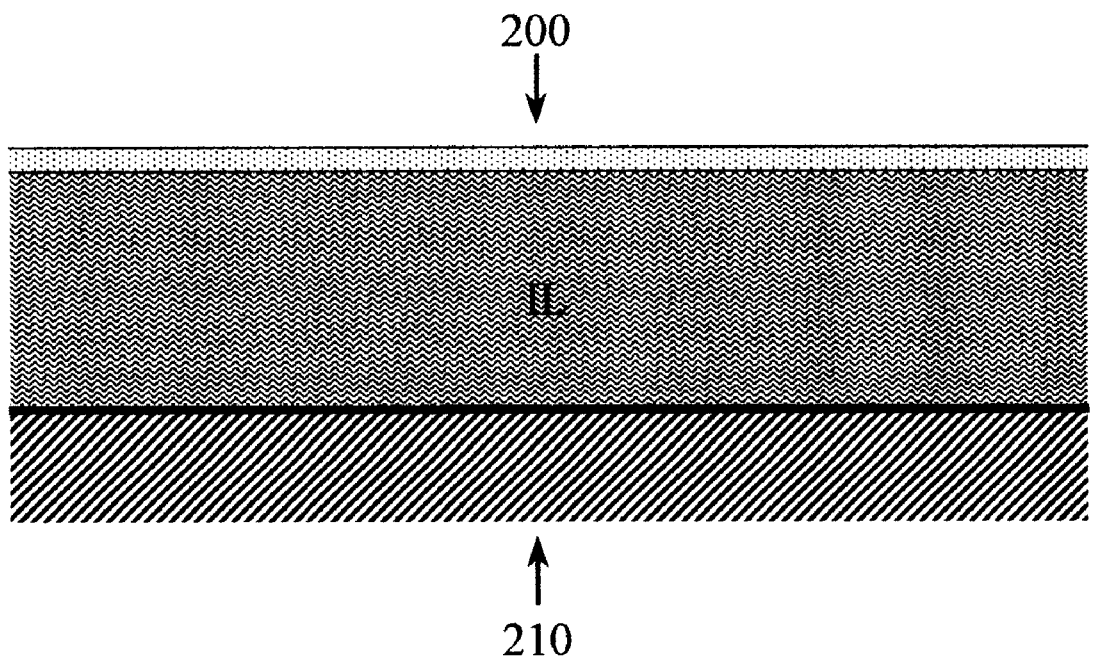

Increases in ILT are further illustrated in FIGS. 2A and B, which is a closer view of interrogation site 100. Skin 200 shows little change in thickness over time due to an increase in capillary related interstitial fluid. In contrast, the IL thickness changes dramatically due to an increase in capillary related interstitial fluid. Bone 210 and skin 200 (skin/bone interface) typically provide reflective surfaces for detecting ILT.

In one embodiment, the invention includes a method of measuring capillary related interstitial fluid comprising: transmitting at least one ultrasound signal to a tissue in a subject in need of capillary related interstitial fluid assessment, recording at least one ultrasound signal from the tissue, and determining a capillary related interstitial layer thickness from a first reflective surface to a second, usually an internal, reflective surface, wherein the capillary related interstitial layer thickness is an assessment of capillary related interstitial fluid. Typically, such a subject will be a human desiring a capillary related interstitial fluid assessment because a clinician wishes to use the invention as a part of a diagnosis or the subject wishes to perform a self assessment of the subject's capillary related interstitial fluid. Often such diagnosis will relate to a clinician's desire to assess capillary related interstitial fluid to determine the status of a subject's homeostasis to ensure that the subject's physiological mechanisms are functioning appropriately. In the case of self-measurement, such measurements will often relate to the subject's desire to monitor changes in homeostatic physiological mechanisms in their own body for health, medical, athletic, or intellectual reasons.

The transmitting step requires transmitting at least one ultrasound signal with sufficient power to permit the signal to travel in the tissue of interest. Typically, the transmitted signal will be reflected off an interface that separates two layers that contain differing amounts of water and biomaterials. Any suitable frequency, as described herein or in the future or known in the art can be used. The frequencies used can be selected for maximum transmission and reflective performance, and lowest noise by recording signals from a tissue at different frequencies. Thus, for a particular tissue, the frequency with the best properties can be selected and a dedicated probe can be constructed using such a frequency. Typically, the frequencies used will range from 0.2 to 20 MHz, preferably from 0.5 to 8 MHz and more preferably from 0.5 to 4 MHz.

The transmitting step is desirably practiced using multiple signals. A plurality of signals can be transmitted and their return signals ("echoes") from reflective interfaces recorded. Signal averaging will improve the accuracy of the measurements and can be conducted over a relatively short period of time. Generally, multiple signals for signal averaging will be transmitted in less than 1 to 2 seconds and more often in less than 100 to 300 milliseconds and preferably in less than 50 milliseconds.

The transmitting step can be optionally practiced using multiple signals over longer lengths of time that would not typically be used for signal averaging. Such lengths of time permit monitoring of shifts or changes in capillary related interstitial fluid. For example, water can shift from blood into capillary related interstitial fluid (or vice versa) and change the amount of capillary related interstitial fluid in a tissue. Such shifts can result from changes in physiological processes or regulated parameters, such as ion transport, oncotic pressure of the capillary related interstitial fluid, oncotic pressure of blood, the amount of osmotically active substances in the capillary related interstitial fluid or blood, extracellular pH or intracellular pH. By transmitting ultrasound signals over lengths of time that correspond to such physiological events, changes in capillary related interstitial fluid can be assessed and compared to normal or standard values and over time. Most physiological events will occur over a much longer time frame than required for signal averaging. Typically, such monitoring will occur over minutes, hours, days and even in some instances, as described herein, it will be desirable to monitor subjects over months or years.

The recording step requires recording at least one ultrasound signal from the tissue. Usually, the signal will be a reflected signal from a reflective interface. Desirably, a plurality of reflected signals are averaged, as described for transmitted signals or known in the art. The returning signals can be optionally filtered or sampled to remove noise and scatter. For example, if a layer(s) at a predictable (or estimated) distance from the probe is present that produces scatter and is not relevant for determining capillary related interstitial fluid volume, return signals can be appropriately sampled to remove such scattering by preferentially recording the signal at times not corresponding to the return signal times from the interfering layer(s). Such methods are also described in patent application Ser. No. 08/731,821 filed Oct. 21, 1996 (Lang et al), which is herein incorporated by reference.

A, B or C scan modes of ultrasound interrogation and recording can be used with the methods and devices of the invention. Preferably, A scan systems will be used to provide relatively inexpensive diagnostic tools: Because most applications only require detecting the distance between layers that contain capillary related interstitial fluid or the thickness of a capillary related interstitial fluid layer, information relating to a third dimension is not necessary.

The determining step requires determining a capillary related interstitial layer thickness from a first reflective layer and a second reflective layer in the tissue or anatomical region. Typically, signals from the first and second reflective layer will be detected by an ultrasound detector at different times. The difference in time of reception between the signal from the first reflective layer and the signal from the second reflective layer can be used to determine the time required for sound to travel from the medium between first and second reflective layers. For example, capillary related interstitial layer thickness can be a reflection of transmission times as described by the following calculation:

$$ILT \propto (\tau 2 - \tau 1) \div 2 \qquad [\text{Eq. 2}]$$

wherein ILT is the interstitial layer thickness, $\propto$ refers to a relationship of proportion (and can include the relationship of equality if calculated using the appropriate factor(s)), $\tau 2$ is the time of transmission of the ultrasound signal from an ultrasound probe (the transmitting signal) to the second reflective layer and back to an ultrasound probe (detecting the return signal), and $\tau 1$ is the time of transmission of the ultrasound signal from an ultrasound probe (transmitting the signal) to the first reflective layer and back to a ultrasound probe (detecting the return signal). ILT for this type of calculation can be expressed in relation to transmission time.

ILT can also be calculated in terms of actual distance, such as centimeters (cm). For example, the transmission time related to the ILT in [Eq. 2], which is units of time, can be multiplied by the speed of sound in the medium being measured. If more than one medium is being interrogated and more than two reflective layers are being interrogated, then the speed of sound for each medium can be incorporated into the calculation. The speed of sound for various tissues and substances typically varies from 331 to 5000 (meters/second), such as air (331), water (1430), saltwater (1510), fat (1450), soft tissue (1540), blood (1585), muscle (1585), PZT-4 transducer (4000), skull bone (4080) and metal (5000) (all in meters per second). Speed of sound in a medium can also be measured empirically, by separating two ultrasound probes by a predetermined distance with the medium of interest between the two probes and transmitting and detecting ultrasound signals between the two probes. Such measurements can be relatively easily accomplished, especially with appendages, and can increase the information content of the data.

It is not, however, necessary to record signals reflected from the first reflective layer. In some is instances, the first reflective layer will be a predictable transmission time and distance form the ultrasound probe and such a predictable transmission time or distance can be used in [Eq. 2] to estimate the ILT. As described further in further detail herein standard transmission times and ILTs can be estimated by sampling subjects or by providing predetermined standards. Thus, capillary related interstitial layer thickness can be qualitatively or quantitatively determined. Nor is it necessary, even for quantitative calculations, to calculate an exact value for the interstitial layer because a delta (i.e. change) in ITL may be all that is clinically relevant.

This embodiment of the invention can be applied to a variety of application sites and medical treatments as described herein, developed in the future or known in the art. This embodiment of the invention also can be used with many different types of suitable probes, systems, and methods relating to ultrasound measurements, and calculations and biological standards, as described herein, developed in the future or known in the art.

Application Sites

Capillary related interstitial fluid can be measured in any tissue or continues anatomical region that contains within it at least one reflective surface and a sufficient amount of water or other acoustic medium to permit ultrasound signals to penetrate and return through the tissue for detection. Often the first reflective surface is the probe-skin interface and the internal reflective surface is a bone-ILT interface. An internal reflective surface refers to a reflective surface on the inside of the body that is not accessible from the outside and is in contact with interstitial fluid. Table 1 shows a number of potential reflective surface combinations for potential application sites for ultrasound probes and some potential diagnostic applications for assessing certain physiological functions. Table 1 is by no means exhaustive, it is only illustrative of the many potential sites and reflective surfaces to monitor capillary related interstitial fluid. Table 1 also includes some embodiments of the invention not associated with capillary related interstitial fluid monitoring, such as ascites and cranial edema. Typically, the subjects will be humans, however, the present invention may be used with other animals, especially large mammals in veterinary settings.

TABLE 1

| First Reflective Surface | Second Reflective Surface | Probe Site | Diagnostic Application |
|---|---|---|---|
| Skin | Bone | Leg (preferably mid, anterior tibia) | Heart, renal, and circulatory function |
| Skin | Bone | Arm (preferably distal radius or alna) | Heart, renal, or circulatory function |

TABLE 1-continued

| First Reflective Surface | Second Reflective Surface | Probe Site | Diagnostic Application |
|---|---|---|---|
| Skin or bone or chest wall muscles | Lung tissue or pleural surface | Chest (preferably mid axillary line, e.g. between $10^{th}/11^{th}$ rib) | Pulmonary edema, pleural effusion, heart and circulatory function |
| Skin or muscle | Bone | Presternal | Heart, renal, and circulatory function |
| Skin | Traumatized tissue | Skin above internal trauma site | Trauma, progression of trauma or healing |
| Skin or muscle or liver tissue or splenic tissue | Liver tissue or splenic tissue or abdominal fat | Skin above left or right paracolic gutter | Ascites, heart failure, renal failure, cirrhosis |
| Skin | Bone | Cranium (preferably temporal bone, forehead or nuchal region) | Head trauma, cerebral edema, heart function |

The sites listed in Table 1 can also be used in combination. By using combinations of probe sites (i.e. multisite monitoring), fluid movement throughout the body can be monitored. This permits monitoring fluid shifts from fluid compartments of the body. Multisite monitoring also permits exquisitely sensitive monitoring of physiological processes related to edema, capillary related interstitial fluid shifts and other fluid related changes in the body, such as processes that either induce, prevent or reduce fluid shifts, as well as therapeutic treatments thereof. Multisite monitoring is further described in detail herein, particularly in the section relating to monitoring physiological functions and in situ probes.

Figure 3:
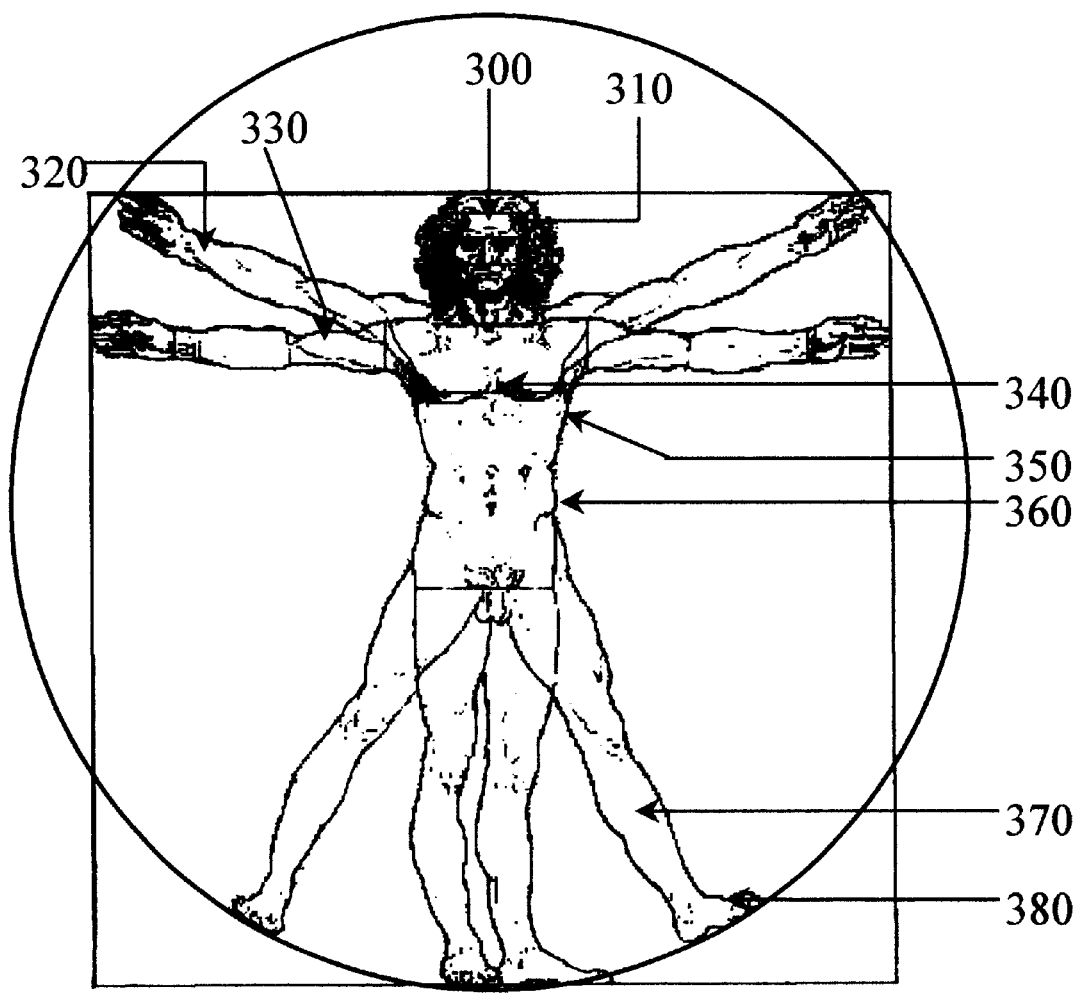
FIG. 3 shows selected, exemplary anatomical regions that can be used for ultrasound monitoring of capillary related interstitial fluid and capillary related edema in a human in need of such monitoring. Exemplary ultrasound interrogation sites include but are not limited to the forehead region 300, the temporal region 310, the forearm region 320, the humeral region 330, the presternal region 340, the lateral chest wall region 350, the lateral abdominal region 360, the tibial region 370, and the foot region 380. The exemplary regions illustrated in FIG. 3 can be used alone or in combination, as described herein.
Figure 4:
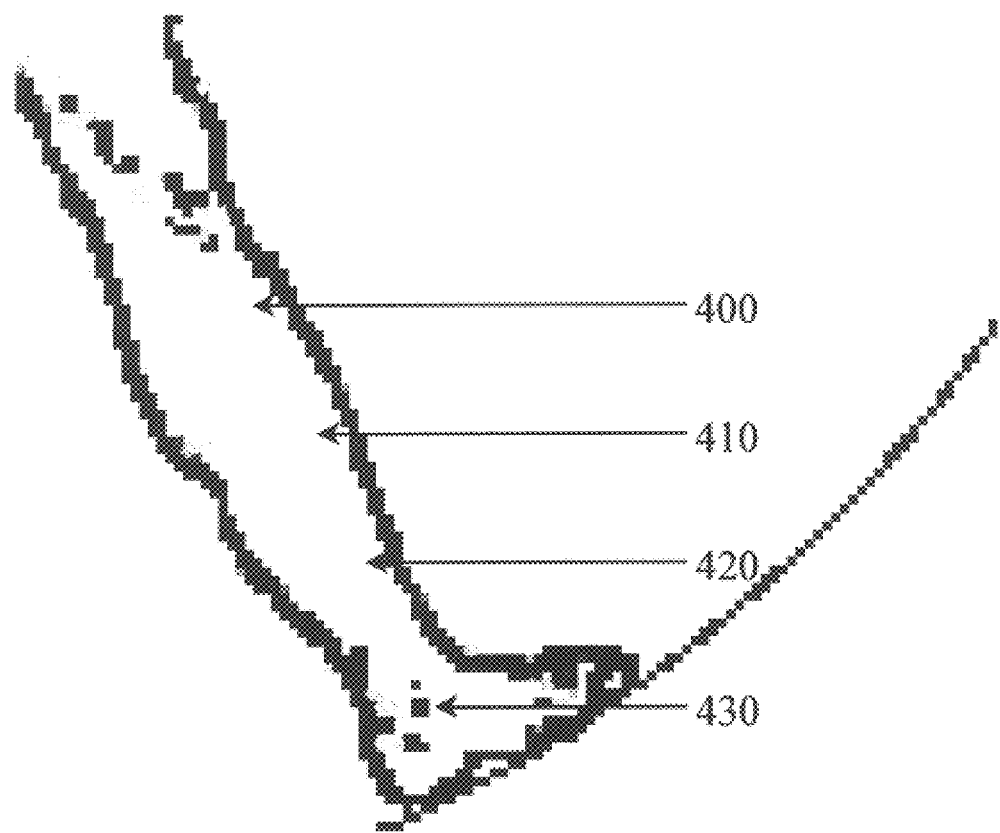
FIG. 4 is a magnified view of the tibial region 370 demonstrating the proximal third of the tibia region 400, the mid-tibia region 410, the distal third of the tibia region 420, and the medial malleolus region 430.

By way of example, and not of limitation, FIGS. 3 and 4 illustrates selected sites that can be used for ultrasound monitoring of capillary related interstitial fluid and capillary related edema as well as other methods described herein. FIG. 3 shows a human subject in need of monitoring of capillary related interstitial fluid. Exemplary ultrasound interrogation sites include, but are not limited to, the forehead region 300, the temporal region 310, the forearm region 320, the humeral region 330, the presternal region 340, the lateral chest wall region 350, the lateral abdominal region 360, the tibial region 370, and the foot region 380.

FIG. 4 is a magnified view of the tibial region demonstrating the proximal third of the tibia site 400, the mid-tibia site 410, the distal third of the tibia site 420, and the medial malleolus site 430. FIGS. 3 and 4 is by no means exhaustive, it is only illustrative of the many potential regions and sites that are available to monitor capillary related interstitial fluid. The exemplary regions and sites illustrated in FIGS. 3 and 4 can be used alone or in combination.

Application to Medical Treatments

Medical treatments often affect interstitial fluid levels. Many medical treatments are designed to modulate the function of an organ or physiological process in order to improve fluid homeostasis. There are numerous examples of drugs designed to modulate heart, renal or pulmonary function and, as a consequence, improve fluid homeostasis. Often when such medical treatments are initiated, it is difficult to establish a baseline for fluid homeostasis other than a general diagnosis of abnormal or pathological fluid imbalance or fluid retention that may or may not be associated with another diagnosed medical condition.

For example, a patient may have pronounced fluid retention in the extremities resulting from right ventricular failure. A clinician when posed with this medical situation might prescribe a drug to improve cardiac performance. The effectiveness of the medical treatment could be measured by examining the patient, similar to the original examination. Often the original examination will only involve a physical examination that may be difficult to directly compare to the second examination, especially the amount of fluid retention in the extremities. Although examination of heart function may be easier to compare between first and second examinations because heart function is often more quantifiable, patients may show changes in systemic function that suggest improvement without measurable improvement in cardiac performance.

In this case, comparing the first and second examination results has a number of drawbacks. The medical treatment for right ventricular failure might not actually improve right ventricular performance even though heart rate may be lowered or contractility improved. Apparent cardiac improvements may also not actually improve water retention in the extremities. Comparing systemic effects in the first and second examination may also be complicated by the fact that the clinician conducting the first examination may not be the same clinician as the one conducting the second examination. It is therefore desirable to compare measurements of fluid retention in a manner that is more easily repeated upon a second examination, less influenced by variability between clinicians, more reproducible, and more quantifiable than physical examination. The methods and device of the present invention permit measurement of fluid retention in a manner that is more easily repeated upon a second examination, less influenced by variability between clinicians, more reproducible, and more quantifiable than physical examination.

The steps of (a) transmitting, (b) recording, and (c) determining related to the method monitoring capillary related interstitial fluid can be performed as multiple patient examinations over different time spans. This is an advantage over the prior art, since this technique can generate values for the interstitial layer that can be compared over time and is less susceptible to inter-clinician and intra-clinician variation. For example, steps of transmitting, recording and determining can be conducted as a baseline for patient monitoring. Such an examination could occur prior to a medical treatment. In the first examination, a first capillary related interstitial layer thickness is determined. In a subsequent examination, steps (a), (b), and (c) are repeated. Examinations subsequent to the first examination could occur after, or simultaneous to, the medical treatment. The timing of subsequent examinations can be any desired by the subject, operator, or clinician. Usually, examination will be periodic or during a predetermined clinically relevant time period.

Routine periodic examinations, such as part of an annual examination, can monitor long term changes in the physiology due a number of medical conditions, such as those described herein. Such periodic examinations can be applied to other methods described herein, such as methods related to monitoring vascular or cardiac performance during a clinically induced stress.

Examinations during a clinically relevant time period can be used to monitor the progress of expected changes in a subject's physiology. Clinically relevant time periods usually relate to a medical treatment regime or medical conditions. The method includes comparing a second capillary related interstitial layer thickness (measured in the subsequent examination) to the first capillary related interstitial layer thickness (measured in a prior examination). The change in capillary related interstitial layer thickness can be indicative in a change in the physiological condition of the subject. For instance, if the second capillary related interstitial layer thickness is larger than the first capillary related interstitial layer thickness, then the medical treatment, or medical condition, has usually induced an increase capillary related interstitial fluid. As a second alternative, if the first capillary related interstitial layer thickness is larger than the second capillary related interstitial layer thickness, then the medical treatment, or medical condition, has usually induced a decrease in capillary related interstitial fluid. As a third alternative, if the first capillary related interstitial layer thickness is equal to the second capillary related interstitial layer thickness, then the medical treatment, or medical condition, has usually induced no change in capillary related interstitial fluid. This type of comparative monitoring, subsequent to a first examination, can be applied to a monitor a number of medical conditions or assess a number of medical treatments.

A desirable aspect of periodic or clinically relevant monitoring is to determine if a change in capillary related interstitial layer thickness relates to more than one physiological change. For example, a change in capillary related interstitial layer thickness may be induced by both short term and long term physiological changes. In such a subject the short term effect can be assessed by inducing physiological changes in the subject that would alter capillary related interstitial layer thickness at the relevant anatomical region in a relatively short examination period (e.g., within about 40 to 120 minutes). Depending on the outcome of such assessment, the clinician can weigh the relative contribution of long term and short term effects on interstitial layer thickness. Preferably, the same type of monitoring was previously performed on the subject so a comparison can be made. Generally, the more rapid or greater the change in interstitial layer thickness, compared to an expected or previous reading, the greater the short term effect. The subsequent diagnosis can then be guided by the relative contributions of short and long term effects.

For example, a typical short term effect on capillary related interstitial layer thickness in the tibial region is prolonged standing (e.g., 4 to 6 hours of continuous standing). A subject monitored using the tibial monitor methods described herein, for instance, may be responding to antidiuretic treatments to reduce capillary related interstitial fluid volume while contemporaneously responding to shorter term effects of standing upright. In such a subject the effect of standing upright for a prolonged period of time can be assessed by inducing physiological changes in the subject that would alter tibial capillary related interstitial layer thickness in a relatively short examination period. For example, by monitoring tibial capillary related interstitial layer thickness in the upright position and in the prone, or leg raised positions, the short term effect of standing upright can be assessed. Rapid changes in tibial capillary related interstitial layer thickness can be generally influenced by short term effects. Note, however, methods described herein, where rapid changes in tibial interstitial thickness can be indicative of increased capillary permeability, compromised venous valves, or insufficient cardiac output. Preferably, a baseline is established for capillary related interstitial layer thickness so comparisons can be made in subsequent measurements.

One of the most common clinical settings for a method of measuring capillary related interstitial layer thickness is the assessment of the efficacy or side-effects of medical treatments. Monitoring regimes can be conveniently and appropriately tailored using the methods described herein to evaluate the progress of treatment. Typically, a drug will be administered to a subject and the steps (a) transmitting, (b) recording, and (c) determining related to the method of monitoring capillary related interstitial fluid are repeated at predetermined intervals as an assessment of capillary related interstitial fluid balance of the subject over a clinically relevant time period. Preferably, baseline monitoring prior to drug administration is also conducted. Typical drugs amenable to such treatment monitoring include cardiovascular agents and renal agents. Other drugs include antihypertensives, diuretics, anticoagulants, and vasoactive substances (see also Table 3). Clinicians, however, can use the method with any drug, particularly those drugs thought to change capillary related interstitial fluid levels either as a treatment for altering capillary related interstitial fluid levels or for monitoring side-effects of drugs that may alter capillary related interstitial fluid levels in undesired or unintended ways.

Another common clinical setting for a method of measuring capillary related interstitial layer thickness is to assess the efficacy or side-effects a medical treatment comprising surgical procedures and treatments. Typically, a surgical treatment will be provided to the subject and the steps of (a) transmitting, (b) recording, and (c) determining related to the method of monitoring capillary related interstitial fluid are repeated at predetermined intervals as an assessment of capillary related interstitial fluid balance of the subject over a clinically relevant time period. Preferably, baseline monitoring prior to surgical treatment is also conducted. The surgical treatment may be directed, in whole or in part, to modulating capillary related interstitial fluid levels. Examples of such surgical treatments include cardiac surgery (e.g., cardiac valve replacement and coronary bypass graft surgery), renal surgery (e.g., surgical or interventional radiologic repair of renal artery stenosis or urinary outflow stenosis), renal and hepatic transplantation, pulmonary arterial embolectomy, peripheral venous or arterial embolectomy, and peripheral vascular surgical and interventional radiologic procedures (e.g., stripping of varicose veins, sclerotherapy, bypass grafting, and thrombolytic therapy), as well as others known in the art or developed in the future. Usually, the clinical relevant time period for monitoring of the efficacy of surgical treatments will be periodically over about days to months.

In other indications related to surgical treatments, monitoring of the side-effects of surgical treatments will be desired. Side effects of surgical treatments include blood loss, cardiac arrest, fat and air embolism, heart failure, hepatic failure, hepatic or renal ischemia and infarction, hypoxic tissue damage, intestinal ischemia and infarction, mechanical tissue damage, myocardial ischemia or infarction, myolysis, pulmonary edema, pulmonary embolism, renal failure, urinary obstruction, respiratory arrest, sepsis, shock, spinal cord injury, overhydration or dehydration, fluid retention in dependent anatomical regions, lower or upper extremity venous thrombosis, and arterial dissection and/or occlusion.

Usually, the clinically relevant time period for monitoring of the side-effects of surgical treatments will be during the surgical procedure or treatment and periodically over about 24 to 96 hours post procedure or treatment. The use of multi-site monitoring and continuous monitoring, as described in further detail herein, will be particularly applicable in this clinical setting. Multi-site monitoring and continuous monitoring can be used to prevent the progression of capillary related interstitial fluid retention, especially in specific anatomical regions during and post surgical treatment, such as the forehead, the temporal region, the occiput, the nuchal region, the cervical region, the thoracic region, the low back region, sacral region, and buttocks region, the sternal region, the anterior or the lateral chest wall, the anterior or the lateral abdominal wall, the humerus region, the forearm region, the hand, the thigh, the tibial region, the calf, the medial and lateral malleolus, the foot, and preferably any such dependent anatomical region (see also FIGS. 3 and 4).

Another common clinical setting for a method of measuring capillary related interstitial layer thickness is to assess the efficacy or side-effects a medical treatment comprising general anesthetic procedures and treatments. Typically, a general anesthetic procedure or treatment will be provided to the subject and the steps (a) transmitting, (b) recording, and (c) determining related to the method of monitoring capillary related interstitial fluid are repeated at predetermined intervals as an assessment of capillary related interstitial fluid balance of the subject over a clinically relevant time period. Usually, the clinically relevant time period will be during a general anesthetic procedure or treatment and periodically over about 24 to 72 hours post procedure or treatment. Preferably, baseline monitoring prior to general anesthetic procedure or treatment is also conducted. Side-effects of general anesthetic procedures or treatments include hypoxic or embolic brain damage, cardiac arrest, drug-induced complications, heart failure, hypoxic tissue damage, intestinal ischemia and infarction, myocardial ischemia or infarction, myolysis, pulmonary edema, pulmonary embolism, renal failure, respiratory arrest, line sepsis, shock, overhydration or dehydration, and lower or upper extremity arterial or venous thrombosis. The use of multi-site monitoring and continuous monitoring, as described in further detail herein, will be particularly applicable in this clinical setting. Multi-site monitoring and continuous monitoring can be used to prevent the progression of capillary related interstitial fluid retention, especially in specific anatomical regions during and post general anesthetic procedure or treatment, such as the forehead, the temporal region, the occiput, the nuchal region, the cervical region, the thoracic region, the sternal region, the anterior or the lateral chest wall, the anterior or the lateral abdominal wall, the humerus region, the elbow region, the forearm region, the hand, the thigh, the tibial region, the calf, the medial and lateral malleolus, the foot, and dependent anatomical regions (see also FIGS. 3 and 4).

Intubation of a subject is another common clinical setting to apply a method of measuring capillary related interstitial layer thickness to assess the efficacy or side-effects associated with this medical treatment. Typically, an intubation procedure will be provided to the subject and the steps of (a) transmitting, (b) recording, and (c) determining related to the method of monitoring capillary related interstitial fluid are repeated at predetermined intervals as an assessment of capillary related interstitial fluid balance of the subject over a clinically relevant time period. Usually, the clinically relevant time period will be during an intubation procedure and periodically over about 24 to 72 hours post procedure to treatment. Preferably, baseline monitoring prior to an intubation procedure is also conducted. Side effects of intubation procedures include airway obstruction, airway damage, barotrauma, gastric intubation, tracheal or bronchial perforation, tracheopleural and bronchopleural fistula, tracheoesophageal fistula, hepatic or renal ischemia and infarction, hypoxic brain damage, hypoxic tissue damage, intestinal ischemia and infarction, myocardial ischemia or infarction, pulmonary edema, respiratory arrest, spinal cord and cervical spine injury, and tetraparesis or paraparesis. The use of multi-site monitoring and continuous monitoring, as described in further detail herein, will be particularly applicable in this clinical setting. Multi-site monitoring and continuous monitoring can be used to prevent the progression of capillary related interstitial fluid retention, especially in specific anatomical regions post intubation procedure, such as the forehead, the temporal region, the cervical region, the thoracic region, the low back region, the sternal region, the anterior or the lateral chest wall, the anterior or the lateral abdominal wall, the humerus region, the elbow region, the forearm region, the hand, the thigh, the tibial region, the calf, the medial and lateral malleolus, the foot, and dependent anatomical regions (see also FIGS. 3 and 4).

Another important application of the present invention is in trauma, intensive or critical care units, or emergency room settings. Such settings normally require critical care procedures of a subject to assess medical conditions that have serious or life threatening consequences. In critical care situations, the steps of (a) transmitting, (b) recording, and (c) determining related to the method of monitoring capillary related interstitial fluid are typically initiated as quickly as possible. In many critical care situations rapid fluid shifts occur and the present invention, in part, because of its sensitivity to small fluid shifts, can warn a clinician of a potentially harmful or life threatening fluid shift.

The method can also be used to monitor the progression of capillary related interstitial fluid that is common in critical care settings. Fluid is often retained in the extremities, the head and neck region, dependent body regions (i.e., regions subjected to fluid accumulation due to gravity) and areas with subcutaneous tissue rich in vascularized tissue and collagen and elastic fibers, such as the scrotum. It will be desirable to repeat the steps of (a) transmitting, (b) recording, and (c) determining related to the method of monitoring capillary related interstitial fluid, particularly at predetermined intervals, as an assessment of capillary related interstitial fluid balance of the subject over a clinically relevant time period. Steps (a), (b), and (c) are typically initiated within 36 hours of a trauma or other critical care setting, preferably within about 24 hours, more preferably within about 6 hours and most preferably within about 15 minutes. Typically, a progressive increase in capillary related interstitial layer thickness indicates an increase in capillary related interstitial fluid and a progressive decrease in capillary related interstitial layer thickness indicates a decrease in capillary related interstitial fluid. Monitoring of capillary related interstitial fluid can occur in many critical care situations, including patients with acquired immunodeficiency syndrome (AIDS), autoimmune disorders, burns, bacteremia, cancer leading to local or distant organ failure, cardiac arrest, coma, drowning or near-drowning, drug-induced complications, drug overdose, heart failure, hepatic failure, infections, inhalation of toxic substances, intestinal ischemia and infarction, myocardial ischemia or infarction, poisoning, pulmonary embolism, renal failure, respiratory arrest, trauma, transplant complications, sepsis, shock, and arterial or venous thrombosis. The use of multi-site monitoring and continuous monitoring, as described in further detail herein, will be particularly applicable in this clinical setting. Multi-site monitoring and continuous monitoring can be used to prevent the progression of capillary related interstitial fluid retention, especially in specific anatomical regions post trauma or other critical care event, such as the forehead, the temporal region, the occiput, the nuchal region, the cervical region, the thoracic region, the low back region, the sternal region, the anterior or the lateral chest wall, the anterior or the lateral abdominal wall, the humerus region, the elbow region including the olecranon, the forearm region, the hand, the thigh, the tibial region, the calf, the medial and lateral malleolus, the foot, and preferably dependent anatomical regions (see also FIGS. 3 and 4).

Different Types of Monitoring

Monitoring of capillary related interstitial fluid can include any temporal method, including periodic, intermittent, predetermined and continuous. In many instances, at least one ultrasound signal is from an ultrasound probe positioned on the surface of a tissue. The positioning guides the probe to a specific and routinely recognizable anatomical region and permits measurement of an interstitial layer, often between bone and skin. The probe can be positioned to allow for periodic, continuous or intermittent monitoring. The more reproducible the positioning the better the monitoring over time. Thus, the probe is preferably positioned at approximately the same anatomical site on the surface of the tissue. The transmitting and recording can occur at clinically relevant time intervals. In many settings where the subject is relatively immobile, such as a hospital or convalescent home, and continuous or intermittent monitoring is preferred, the time intervals are over at least about a 4 hour time period. Other acceptable time interval include monitoring over at least about a 6, 12, 24, 48, 72, or 96 hour time periods. Longer or shorter monitoring periods can also be applied. Usually, the clinical situation the subject has been diagnosed with requires chronic or continual capillary related interstitial fluid assessment.

The ultrasound probe used for interstitial fluid monitoring preferably is specifically adapted for interstitial fluid assessment. Examples of such specifically adapted probes are described herein for the first time. Preferably, for self-measurement the probe is part of an ultrasound system dedicated to monitoring interstitial fluid assessment. Such systems can be primarily designed to measure interstitial fluid levels, usually based on specific anatomical regions using an ultrasound probe. Often such systems will include a chip for computing interstitial layer thickness. Equivalently, the calculation of a proxy that approximately simulates interstitial fluid volume or capillary related interstitial fluid thickness based on ultrasound signals may be substituted for computing the ILT thickness. Other features that can be included in dedicated probes are more fully described herein. Although, imaging systems can be used to practice some embodiments of the invention, it will be preferred to use non-imaging systems that can determine interstitial layer thickness. Probes known in the art and developed in the future can also be used for practicing methods of the invention.

Figure 5A:
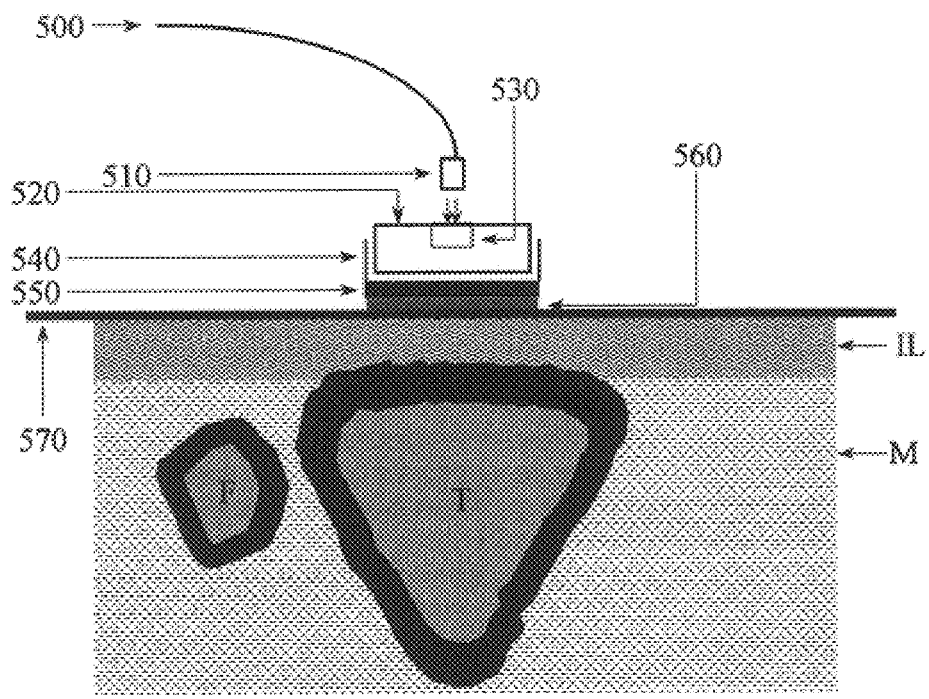
FIGS. 5A and B show embodiments of the invention comprising an ultrasound transducer secured to a subject or a tissue surface with an adhesive probe holder, which is preferably used for intermittent or continuous recording. The ultrasound transducer can be electrically coupled to an ultrasound computational unit (not shown) using a light weight wire 500. An electrical connector 510 connects the computational unit and the ultrasound transducer 520 using an electrical connecting socket or connector means 530. The ultrasound transducer 520 is optionally seated inside a positioning frame 540. The undersurface of the positioning frame consists of an acoustic coupler 550. The positioning frame is attached to the subject or tissue surface using an adhesive 560. The adhesive 560 can acoustically couple the ultrasound probe to the skin of the subject or the interrogated tissue surface 570. The adhesive 560 can also be interspersed with an acoustic coupling material, such as a gel (not shown). Tibia is "T". Fibula is "F". Muscle is "M" and interstitial layer is "IL".
Figure 5B:
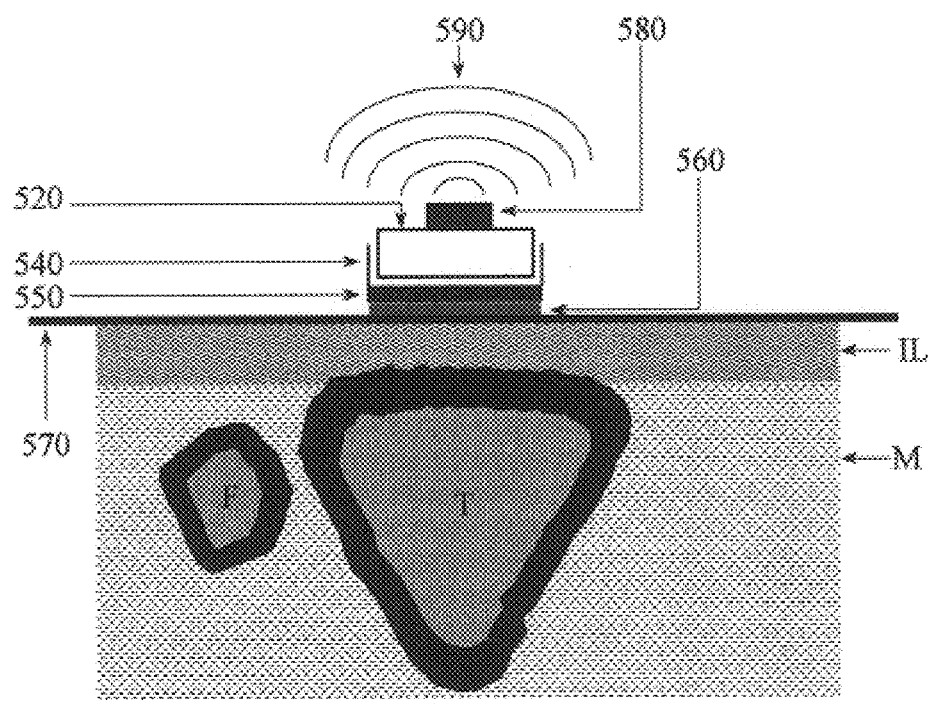
FIG. 5B shows that the ultrasound transducer 520 can also be coupled to an ultrasound computational unit (not shown) using an infrared coupler or a radio frequency coupler 580 or other connector means that transmits signals 590 to an ultrasound computational unit.

In one embodiment, the ultrasound probe can be secured to the subject with an adhesive as shown in FIGS. 5A and B. This is preferred for methods that use intermittent or continuous recording. The ultrasound transducer can be electrically coupled to an ultrasound computational unit (not shown) using a light weight wire 500. An electrical connector 510 connects the computational unit and the ultrasound transducer 520 using an electrical connecting socket or connector means 530. The ultrasound transducer 520 is optionally seated inside a positioning frame 540. The undersurface of the positioning frame consists of an acoustic coupler 550. The positioning frame is attached to the subject or tissue surface using an adhesive 560. Usually, for better acoustical coupling the skin of the subject is hairless or the hair is removed. Although, this is not necessary in most instances. Preferably, the adhesive 560 can acoustically couple the ultrasound probe to the skin of the subject or the interrogated tissue surface 570. Although, the adhesive can also be interspersed with an acoustic coupling material, such as a gel. An adhesive may also be applied to a securing band that is disposed on at least a portion of the probe that does not contact the skin. The adhesive contacts a region adjacent the probe to secure the probe's position. Preferably the adhesive contacts the skin on either side of the probe.

Figure 6:
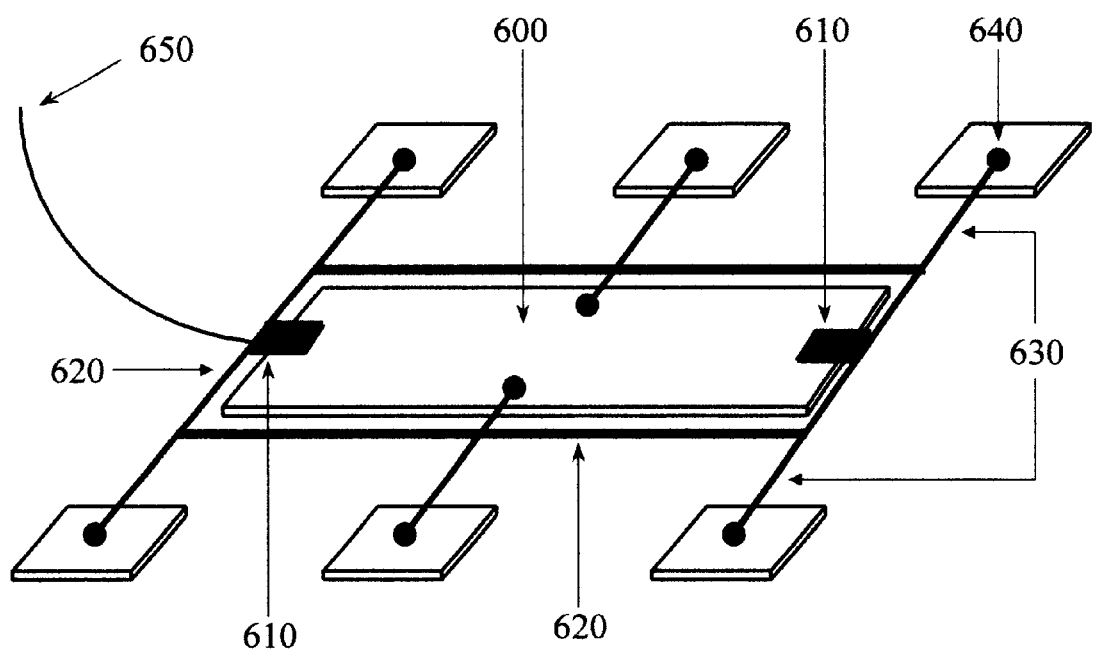
FIG. 6 shows one embodiment of the invention comprising an ultrasound transducer 600 attached to a separate positioning frame 620 with an attachment member 610. The extending members 630 of the positioning frame are attached to securing members 640 to secure the frame to the skin away from the interrogation site. The securing members are secured to the skin using an adhesive or other anatomical region attachment means (not shown). The ultrasound transducer is electrically coupled to an ultrasound computational unit (not shown) using a light weight wire 650. Alternatively, the ultrasound transducer can be coupled to an ultrasound computational unit using an infrared or radio frequency coupler (not shown).

FIG. 6 shows one embodiment of the invention comprising an ultrasound transducer 600 attached to a separate positioning frame 620 with an attachment member 610. The extending members 630 of the positioning frame are attached to securing members 640 to secure the frame to the skin away from the interrogation site. The securing members are secured to the skin using an adhesive or other anatomical region attachment means. The ultrasound transducer is electrically coupled to an ultrasound computational unit using a light weight wire 650. Alternatively, the ultrasound transducer can be coupled to an ultrasound computational unit using an infrared or radio frequency coupler.

Dedicated and secured probes can have many different cross sectional areas. As the size of the cross sectional area increases, a larger area is monitored, which in some applications is desirable because a greater surface area can produce better signal averaging. If the probe surface, however, is larger than the anatomical region to be interrogated the signal quality will diminish. Consequently, probe size can be tailored to fit a particular anatomical region. In some applications it will also be desirable to have a probe that specifically interrogates a smaller region in order to improve sensitivity. In some anatomical regions, such as the tibial region, a focused interrogation, in terms of surface area, can permit more sensitive measurements. Typically, the ultrasound probe has a surface area of no more than 7 cm$^2$, preferably 5 cm$^2$, and more preferably 2 cm$^2$.

Calculations and Standards

Calculations relating to capillary related interstitial fluid and layers can be used with the devices and methods of the present invention. Many of the calculations are related to signal processing, including calculating the ILT, signal averaging, calculating the shortest reflective distance, and threshhold setting. Generally, ILT is calculated as follows:

$$FRD - SRD \quad [\text{Eq. 3}],$$

wherein FRD (first reflective distance) is calculated as the time of travel from a probe to a first reflective layer (usually skin) and back to the probe multiplied by the speed of sound in a given tissue(s) and divided by two, and SRD (second reflective distance (such as an internal reflective distance, usually bone) is calculated as the time of travel from a probe to a second reflective layer (usually bone or fat) and back to the probe multiplied by the speed of sound in a given tissue(s) and divided by two.

A computational unit can be included in a system to calculate ILT using Eq. 3 or any other calculation that can be used in the methods described herein or known in the art or developed in the future for ultrasound. For instance, it may not be necessary in some applications to use Eq. 3 because the first reflective distance is filtered out by the system and only the second reflective distance is calculated. The second reflective distance will still often be, even in the absence of a first reflective distance correction, an indicator of ILT, in appendage regions. Skin thickness usually does not change as much as interstitial layer thickness, therefore ILT is often not greatly influenced by such correction. Skin thickness usually does not provide a large relative contribution to overall tissue thickness. Consequently, ILT is often relatively insensitive to the inclusion of skin thickness in ILT measurements.

Skin thickness can also be standardized and subtracted (see methods described herein) from the second reflective distance to determine ILT. This is preferred in applications where skin thickness becomes a significant contributor to tissue thickness (e.g., young individuals, tibial regions, and subject of normal or below normal weight). Preferably, the invention does not include a computational unit capable of processing signals for imaging. In the preferred embodiments of the invention, the system simply processes the signals without reconstructing an image from the signal. By using an A scan type ultrasound system, a dedicated system can be built relatively inexpensively. The invention also includes a computer program product that includes a computer readable storage media that includes a computer program to calculate or estimate ILT using Eq. 3.

Determination of a reflective layer will typically constitute either analysing signals for the most intense, narrow signals or by threshold setting. Signals received from the tissue by the detector are processed or stored by the system for subsequent processing. Selection of reflective layers can include determining which signal contains the highest amplitude or averaging a number of signals and determining the highest amplitude for the averaged signals. Once the highest amplitude has been selected, the travel time associated with the highest amplitude is used to determine the distance to the reflective layer. Either travel times or distances can be used in an electronic or computational filter to remove data with either travel times or distances that are considered a priori as artifacts. For instance data can be excluded with travel times considered to be too short to be associated with a first reflective layer associated with skin. Often inexperienced operators can inadvertently include an air gap between the probe and skin or not properly apply a coupling gel to the surface of the skin. Such operator errors can lead to anomalous data that includes abnormal short travel times or distances that can be excluded from the analysis by a computational unit. Optionally, the computational unit can electronically apprise the operator of the potential error by signaling the operator, such as with a bell, flashing light or other error message. The system can also include an override function to enable the operator to dismiss the error. Upon repetition of the measurement the operator may determine the signal is not in error and wish to override the preprogrammed error function of the system.

Signals received by the detector can be subjected to threshold processing. Typically, threshold processing excludes signals of a predetermined value or range of values. The signal processing can potentially exclude signal either above or below the predetermined threshold value. The predetermined threshold value for a signal can include: 1) predetermined values correlated with, or selected from, anatomical sites and structures (e.g., estimates of actual thicknesses), 2) predetermined values generated from interrogating the tissue under examination (e.g., generating average values for the tissue under examination), and 3) predetermined values generated from interrogating tissues to determine normative values for different tissues, subject populations, medical conditions, etc. (e.g., generating average values from particular anatomical sites or structures using multiple qualified subjects).

A system or detector can exclude signals at different levels of signal detection or processing. For instance, signals can be excluded by time gating, electronic filtering, digital filtering, analog filtering, and amplitude gating. Such filtering can be applied to both B-scan and A-scan devices. Preferably, such filtering is applied to A-scan devices in the form of a simple electronic circuit.

Time gating can be used to exclude or filter out signals received by the detector. For example, signals received by crystals can be excluded by switching off the circuit receiving electrical impulses from the crystals during a selected time window. Signals received during this time window are not subjected to further processing. The circuit receiving electrical impulses from the crystals need not be switched completely off. Instead such circuit can be instructed not to receive signals during the time window, such as by electrical gating of an amplifier receiving signals from the crystals. Alternatively, signals can be time gated by analysing the signals received by the crystals. Through analysis of the signals as a function of time, signals received during selected time windows can be simply excluded.

Electronic circuits or devices can be used to exclude or filter out signals received by the crystals to accomplish electronic filtering. A circuit can be connected to the crystals to exclude signals with unwanted transmission times or amplitudes. Signals received either too quickly or too slowly can be excluded using circuits with appropriate time responses, such as capacitive devices with different time constants. Signals received with either too small or too large of an amplitude can be excluded using circuits with appropriate amplitude responses. For example, avalanche type circuits can be used. When an electrical threshold is surpassed (e.g., gating current), the current activates an amplifier. The signal current rapidly increases from zero to a value substantially above background. Reverse amplifier circuits can be used to reduce or eliminate signals with amplitudes such as capacitive devices with different time constants. Alternatively, the signals can be digitized as known in the art and signals excluded based on digital exclusion criteria (either amplitude, timing, or frequency information) that can form part of either a chip (e.g., a programmed chip) or program.

Figure 7:
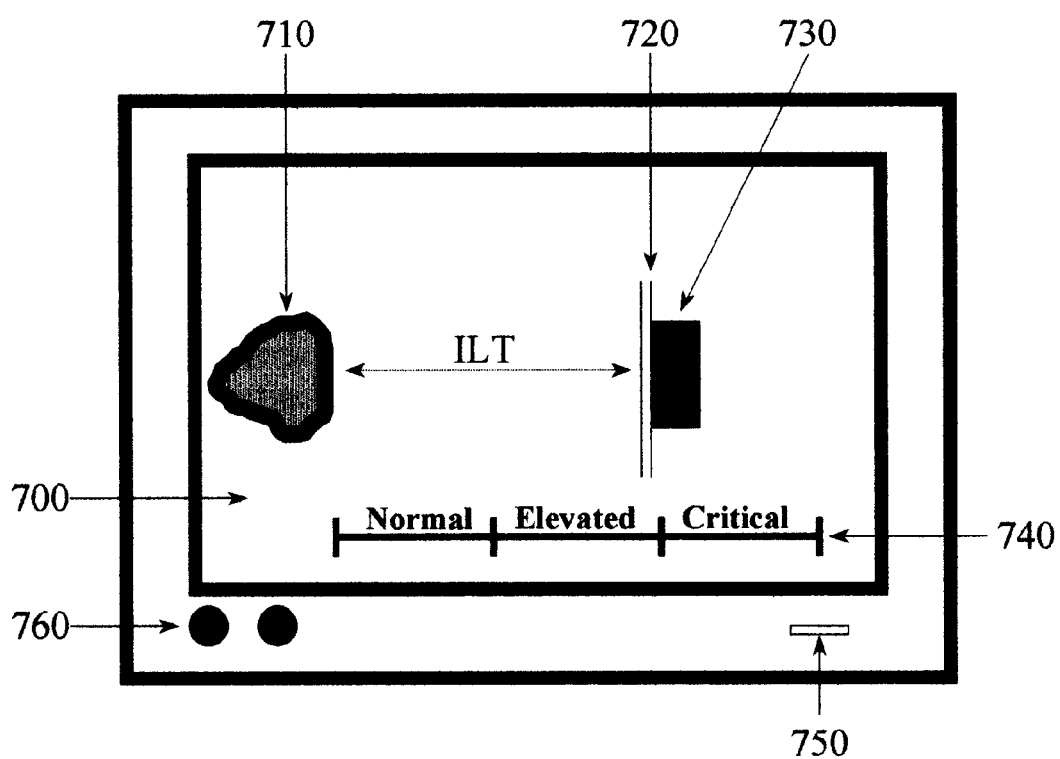
FIG. 7 shows one embodiment of the invention comprising a predetermined display arrangement 700 that includes symbols or illustrative graphics of preselected anatomical features of the interrogated tissue. Such graphics or symbols can be used to display calculated distances or estimated features, such as measured interstitial layer thickness "ILT". In this exemplary illustration, a graphic presentation of bone, e.g. the tibia 710 is displayed stationary, while a graphic presentation of the subject's skin 720 and of the ultrasound transducer 730 can move to the left or the right side. The displayed distance between the bone 710 and the skin 720 corresponds to measured ILT. The position of skin 720 and ultrasound transducer 730 can also provide a diagnostic scale 740 indicating whether the patient's fluid status is normal "normal", elevated "elevated", or critical "critical" for the patient's underlying condition. Such a diagnostic scale 740 can be useful in multiple medical conditions, e.g. impaired vascular, cardiac, renal, or hepatic function. The display unit can have a light 750 indicating, if the device is turned on, and contrast and brightness adjustments 760.

Signals, results of calculations, or signal processing can be displayed on a digital or analog display for the operator or the subject to observe. The display can also include a predetermined display arrangement that includes symbols or illustrative graphics of preselected anatomical features of the interrogated tissue. Results of calculations can then used in the graphic to display the calculated distances (or other suitable information) associated with the predetermined anatomical features. For example, FIG. 7 shows bone 710, ILT "ILT", skin 720 and probe 730 that were preselected and designed as a graphic for display on a screen. After the computational unit processes the data, processed information, such as calculated distances, can then be inserted into the displayed graphic. It will also be desirable to provide display features that show the change in absolute ILT (in mm or cm) over time (or the derivative of absolute ILT as a function of time) or the percent change in ILT over time. Such time based displays will be particular useful in chronic, continuous, and short term periodic monitoring. Such displays are another useful aspect of the invention. The displays generally include a screen that is electronically controlled by a computational unit and shows a calculation or representation of an ILT. Such displays do not include images generated by ultrasound recordings, such as a B-scan image.

One aspect of the invention includes a screen display comprising a predetermined set of anatomical features that appear on the screen. Usually, the predetermined set of anatomical features that appear on the screen reflect at least one processed signal. The processed signal could, for instance, be a distance measurement that is displayed on the screen and corresponds to at least one anatomical feature of the predetermined set of anatomical features. The predetermined set of anatomical features can include any features known for an interrogated tissue. Such features can appear as a simulated image on the screen of an anatomical region. The image can reflect distances between anatomical features. Usually, at least one distance corresponds to at least one processed signal. The image typically comprises common anatomical features, such as bone, skin, interstitial layer and muscle. This aspect of the invention is particularly useful for displaying signals from dedicated diagnostic device, such as ultrasound devices (particularly A-scan devices), NMR devices, computed tomography devices, nuclear medicine devices, bone densitometry devices, radiographic devices, and other current and future diagnostic devices. The screen can optionally include subject data, such as historic records from previous examinations. For example, the screen display can include at least one image that reflects at least one processed signal previously stored in a storage device.

Figure 8:
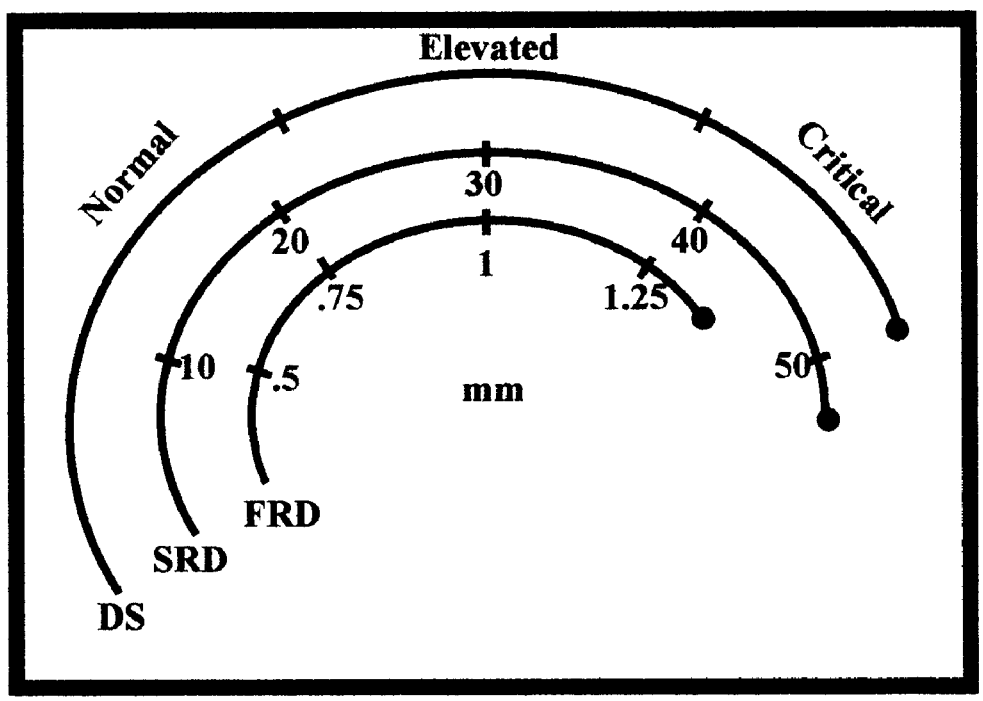
FIG. 8 shows one embodiment of the invention in which first reflective distance "FRD", usually the distance from the ultrasound probe to the inner surface of the skin, and second reflective distance "SRD", typically the distance from the ultrasound probe to the bone or to the inner border of the subcutaneous fat, can be displayed on an analog scale in millimeters "mm" and the operator can manually calculate interstitial layer thickness. The analog display can include a diagnostic scale "DS" which indicates if the patient's fluid status is normal "normal", elevated "elevated", or critical "critical" for the patient's underlying condition.

Not all aspects of the invention require calculations for determining ILT. Instead, either ILT can be read on an analog display or a proxy for ILT can be substituted. For instance, the first and second reflective distances can be calculated and displayed on an analog display along with a distance scale and the operator can manually calculate the ILT. For example, FIG. 8 shows a screen with an analog display and a distance scale for FRD "FIRD" and SRD "SIRD". The analog display may optionally include a diagnostic scale "DS" for clinical use. The diagnostic scale may be predetermined by the clinician, created by an expert system or by the methods described herein. Alternatively, the analog display may have only a diagnostic scale. The diagnostic scale could also be based on predetermined values for the ratio of the SRD to FRD or absolute values of the SRD or FRD. The diagnostic scale may also reflect vascular, cardiac, hepatic, or renal function. The diagnostic scale may be adjustable for the patient's underlying condition, e.g. the scale may be switchable from a cardiac to a renal mode. Physiological performance may be subdivided into categories such as normal, abnormal, and critical or modifications thereof.

The method or the system can further include comparing capillary related interstitial layer thickness with a standard value for capillary related interstitial layer thickness for a particular tissue. A computational unit can compare measured ILTs to ILT standards described herein. By comparing ILT values the clinician or operator can be apprised of the clinical situation. Warning or diagnostic signals can be programmed into the system to alert the clinician or operator of the possible medical implications of the ILT evaluation. Diagnostic thresholds can be used to alert operators of sub- or supra-medical thresholds related to medical conditions. Although, a particular subject may not ultimately require medical treatments if the measured ILT falls below or exceeds a sub- or supra-medical threshold, respectively, such sub- or supra-medical thresholds can provide indications or clinical warning signs that may provoke additional testing either with ultrasound or with other diagnostic tools.

The methods and devices of the invention for detecting ILT can be extremely sensitive. Typically, the present invention can measure changes in ILT as small as about 0.4 to 1.0 mm. Smaller and larger changes in ILT can also be measured. The ability to detect small changes in ILT is primarily influenced by probe frequency, tissue depth and the strength of the reflective layer interrogated, as described further herein. The higher the probe frequency, in general, will improve probe interrogation of shallow interrogation depths (e.g., about 1 to 20 mm). Generally, probes above 18 MHz are preferred (e.g., about 20 to 30 MHz) for shallow interrogation depths. For deeper interrogation depths (e.g., greater than about 20 mm) shorter frequency probes are desirable (e.g., about 5 to 15 MHz). Even shorter frequency probes, are desirable for interrogating particularly thick tissues (e.g., extremely thick appendages or large subjects). As the tissue thickness increases, a relatively small change in ILT (e.g., about 0.5 mm) will become a smaller percentage of total ILT. This can lead in some instance to decreases in the signal-to-noise ratio and make it more difficult to determine ILTs at deep interrogation depths. Consequently, it will be desirable to match probe frequency to the tissue depth or anticipated depth of interrogation. Generally, percentage changes in ILT can be measured at about 25 percent or higher, preferably about 10 percent or higher, more preferably about 5 percent or higher, and most preferably about 1 percent or higher. Consequently, with shorter clinically relevant time periods, it is desirable to provide high sensitivity aspects of the invention in order to detect small changes in ILT over time.

For example, the present invention can detect small changes in ILT as function of time. Generally, for physiological processes or challenges that rapidly affect ILT, changes in ILT can be detected in about 1 to 90 or less, preferably about 1 to 30 minutes or less, and more preferably about 5 to 30 minutes or less. At these time frames, the more sensitive aspects of the invention are preferred. Generally, for physiological processes or challenges that slowly affect ILT less sensitive aspects of the invention can be used.

Empirical Methods for Determining Standards

In one embodiment of the invention, ILT measured in a patient is compared to reference ILT's obtained from a control population (e.g. age-, sex-, race-, or weight-matched normal subjects). Reference ILT's can be generated by measuring interstitial layer thickness in healthy subjects with normal vascular, cardiac, hepatic, or renal function and no other underlying medical condition. Reference ILT's can be expressed as but are not limited to, mean and standard deviation or standard error. Reference ILT's can be obtained independently for pediatric patients and patients 15–20, 20–30, 30–40, 40–50, 50–60, 60–70, 70–80, and 80 and more years of age. Reference ILT's for these age groups can be obtained separately for men and women and for race (e.g. Asian, African, Caucasian, and Hispanic subjects). Additionally, reference ILT's can be obtained for different subject weights within each age, sex, and racial subgroup. For each subgroup defined in this fashion by age, sex, race, and weight, reference ILT's can be measured at various anatomic sites, such as the forehead, the temporal region, the occiput, the nuchal region, the cervical region, the thoracic region, the low back region, the sacral region, the buttocks region, the sternal region, the anterior or the lateral chest wall, the anterior or the lateral abdominal wall, the humerus region, the elbow region including the region of the olecranon, the forearm region, the hand, the thigh, the tibial region, the calf, the medial and lateral malleolus, and the foot (see also FIGS. 3 and 4).

Similarly, reference values for skin thickness, e.g. first reflective distance, can be obtained in healthy subjects with normal vascular, cardiac, hepatic, or renal function and no other underlying medical condition. Reference values for skin thickness can be obtained independently for pediatric patients and patients 15–20, 20–30, 30–40, 40–50, 50–60, 60–70, 70–80, and 80 and more years of age. Reference values for skin thickness for these age groups can be obtained separately for men and women and for race (e.g. Asian, African, Caucasian, and Hispanic subjects). Additionally, reference values for skin thickness can be obtained for different subject weights within each age, sex, and racial subgroup. For each subgroup defined in this fashion by age, sex, race, and weight, reference skin thickness can be measured at various anatomic sites such as the forehead, the temporal region, the occiput, the nuchal region, the cervical region, the thoracic region, the low back region, the sacral region, the buttocks region, the sternal region, the anterior or the lateral chest wall, the anterior or the lateral abdominal wall, the humerus region, the elbow region including the region of the olecranon, the forearm region, the hand, the thigh, the tibial region, the calf, the medial and lateral malleolus, and the foot (see also FIGS. 3 and 4).

When reference values of skin thickness have been determined for a given anatomic site, ILT may be calculated by subtracting the reference value of skin thickness for the patient's age, sex, race and weight group from the measured second reflective distance. Alternatively, reference data for skin thickness published in the literature may be subtracted from the second reflective distance. For example, skin thickness at the dorsal side of the mid-forearm has been reported to be approximately 0.95 mm at age 5 years of age, increasing to 1.2 mm at 45 years of age, and decreasing to approximately 0.7 mm at 80 years of age. Skin thickness at the ventral side of the forearm has been reported to be 0.8 mm at 5 years of age without significant variation between the first and the seventh decade of life (deRigal et al., J Invest. Dermatol. 1989). Other investigators reported a skin thickness of 1.3 mm±0.2 at the palm and the dorsum of the hand, 1.4 mm±0.3 at the forearm, 1.6 mm±0.3 at the calf, 1.9 mm±0.4 at the posterior sole, 2.0 mm±0.3 at the forehead, 2.3 mm±0.5 at the lower back (Fornage et al., Radiology 1993).

If skin thickness does not provide a large relative contribution to overall tissue thickness, no correction may be necessary. Alternatively, the device may measure the first reflective distance, e.g. skin thickness, in each individual patient directly and ILT may then be obtained by subtracting measured first reflective distance from measured second reflective distance.

In another embodiment of the invention, measured ILT can be compared to the control population (e.g. age, sex, race, or weight-matched normal subjects) reference ILT for a given patient. If the measured ILT falls outside a certain range defined based on the reference ILT, an alarm such as a bell, a flashing light, or a message will be generated by the device indicating that the patient has an ILT and, ultimately, an amount of interstitial fluid lower or higher than the healthy reference population. The device may be set to generate the alarm when the measured ILT is one, two, or three standard deviations above or below the reference ILT. In this fashion, the device can be used to diagnose capillary related edema. The magnitude of the discrepancy between measured ILT and reference ILT can also give an indication of the severity of interstitial fluid accumulation or depletion.

Normal ILT in healthy subjects will vary significantly depending on the anatomic site. In the pretibial region, normal ILT may range from 0.2 mm to 3 mm. At the dorsum of the foot, normal ILT may range from 0.2 mm to 2 mm. In the thigh, normal ILT may range from 1 mm to 2.5 cm. In the low back, sacral, and buttock region, normal ILT may range from 0.5 mm to 4 cm. In the abdominal region, normal ILT may range from 2 mm to 5 cm. In the sternal and chest wall region, normal ILT may range from 2 mm to 3 cm. In the humeral region, normal ILT may range from 0.5 mm to 1.5 cm. In the forearm region, normal ILT may range from 0.2 to 3 mm. In the forehead and temporal region, normal ILT may range from 0.2 mm to 2 mm. In the occipital region, normal ILT may range from 0.5 mm to 3 mm. In the nuchal region, normal ILT may range from 0.5 mm to 1.5 cm. Values in all of these regions may be significantly higher in obese patients.

ILT will change significantly depending on the patient's fluid status. In patients with a low interstitial fluid volume, e.g. from dehydration, blood loss, or high intracapillary colloid osmotic pressure, ILT's may be as low as about 25% of the control population reference value. In patients with capillary related edema, e.g. patients with heart failure, renal failure, hepatic failure, or venous insufficiency, ILT may increase 20 fold or even more. If the patient's clinical situation deteriorates, e.g. the patient develops heart failure or his condition worsens, ILT can increase by 35% or more within 15 minutes (see Example 2).

Changes in ILT may vary depending on the patient's age. Younger patients are more likely to compensate for a sudden physiological imbalance or challenge, e.g. intraoperative overhydration by rapid saline infusion. Thus, increases in ILT may be less significant in younger than in older subjects. However, the elastic properties of the skin and ILT may decrease with age thereby reducing rapid expansion of the ILT in older patients with sudden fluid challenge.

Similarly, expansion or decreases of the ILT may be masked in very obese patients since the change in ILT induced by the interstitial fluid shift may be small compared to the patient's already large ILT prior to the fluid shift.

Different medical conditions may demonstrate regional variations in the amount of capillary related edema and ILT. These regional variations may potentially be useful for differentiating different etiologies of capillary related edema. Capillary related edema secondary to varicosity of the deep calf veins and other veins may be more prominently seen at distal sites such as the foot and calf Edema induced by abnormal colloid-osmotic pressure as is seen in hepatic disease with associated hypalbuminemia may involve both proximal and distal sites in a more uniform fashion.

Different medical conditions may also show regional variations between dependent and non-dependent body regions. Capillary related edema in venous disorders may preferentially affect the dependent body portions, while capillary related edema in patients with abnormal capillary permeability from allergic reactions may affect both dependent as well as non-dependent body regions.

4.0 METHODS AND DEVICES FOR MEASURING CAPILLARY RELATED EDEMA

Edema is a medical condition that primarily relates to inappropriate or compromised regulation of fluid in cells or interstitial compartments. As a secondary consequence of a compromised or faltering physiological process, it is often associated with death in many disease states. Comprised cardiac, capillary, hepatic, or renal function can all lead to edematous states, particularly in the appendages.

Capillary related edema refers to an abnormal fluid imbalance arising from capillaries and leading to abnormal local fluid retention. This type of edema is associated with vast majority of edema related medical conditions. Capillary related edema results from an abnormal physiological function or physiological challenge to the venous system, arterial system, cardiovascular system, renal system, hepatic system, pulmonary system or other non-circulatory, internal organ systems normally involved in homeostasis of normal fluid retention in the capillaries. The present invention is particularly applicable to the systemic aspects of capillary related edema. Unlike edema, capillary related edema does not refer to lymphatic related edemas, which have a completely different etiology. For example, pretibial myxedema is a lesion in the dermis that leads to tissue swelling and is associated with the disruption of the lymph system.

One of the clinically important aspects of the invention are methods and devices for monitoring capillary related edema. One embodiment of the invention includes a method of detecting capillary related edema in a subject. An ultrasound probe is positioned on an anatomical region, such as an appendage region of a subject in need of capillary related edema detection. Positioning is typically on the surface of the subject's skin. At least one ultrasound pulse is applied to the region at a duration and frequency to permit detection of bodily tissues. At least one ultrasound signal is then recorded with an ultrasound probe from the region. This permits the detection of the presence or absence of a capillary related edema layer in the region from the ultrasound signal(s).

Anatomical Regions

Capillary related interstitial fluid can be measured in any tissue that contains at least one reflective surface and a sufficient amount of water or other acoustic medium to permit ultrasound signals to penetrate and return through the tissue(s) for detection. Preferred anatomical regions are characterized by a first reflective surface comprised of a skin-ILT interface and second reflective surface comprised of a bone-ILT interface. Table 2 shows a number of preferred potential application sites for ultrasound probes preferred for certain types of capillary related edema. While these sites are preferred, non-preferred sites can be readily used in most applications and empirical tests can be quickly performed to determine other diagnostically useful sites. Preferably, probes are adapted to permit self measurement in most of these regions or adapted for dedicated measurement in these regions. Probes dedicated to measurement of capillary edema in a particular region may function in other regions, although they have been configured to optimize signals from a particular region, as described herein. Table 2 is by no means exhaustive, it is only illustrative of the many potential preferred sites and reflective surfaces to monitor capillary related edema. Particularly preferred sites include the tibia region (even more preferably the proximal tibia), sites where a potential capillary related edema layer extends from the inner surface of the skin to either a fat or bone surface (especially in the tibia or humeral region), the forehead, the anterior or posterior forearm region, the dorsum of the hand, and the medial or lateral malleolus. Typically, the subjects will be humans, however, the present invention may be used with other animals, especially large mammals in veterinary settings.

TABLE 2

| First Reflective Surface | Second Reflective Surface | Probe Site | Type of Capillary Related Edema |
|---|---|---|---|
| Skin | Bone | Leg (preferably mid, anterior tibia) | Cardiac, venous, renal, and hepatic system; hypertension; physiological challenge |
| Skin | Bone | Arm (preferably distal radius or alna) | Cardiac, and arterial system: hypertension; |
| Skin or muscle | Bone | Presternal | Cardiac and arterial system |
| Skin | Traumatized tissue | Skin above internal trauma site | Trauma |
| Skin | Bone | Cranium (preferably temporal bone, forehead or nuchal region) | Physiological challenge |

The sites listed in Table 2 can also be used in combination. By using combinations of probe sites (i.e. multisite monitoring), systemic or regional fluid shifts can be assessed. Multisite monitoring also permits exquisitely sensitive monitoring of physiological processes related to capillary related edema, such as processes that either induce, prevent or reduce capillary related edema, as well as therapeutic treatments thereof Multisite monitoring is further described in detail herein, particularly in the section relating to monitoring physiological functions and in situ probes. These aspects of the invention do not necessarily, and preferably do not, include measuring the degree of skin echogenicity. Methods described herein can be used to improve the signal from tissues interrogated for a capillary related edema layer. For instance, the thickness of a capillary edema layer can be measured by determining the shortest reflective distance described herein.

Use in Medical Conditions and Treatments

In many instances it will be useful to interrogate tissues for a capillary related edema layer before, concurrent with, or after the diagnosis of a medical condition. Often subjects with diabetes, compromised renal function, compromised vascular function, or compromised cardiac function have or will have capillary related edema, especially in the appendages. Early traditional clinical signs of capillary related edema may be difficult to register. In contrast, the present invention provides an unparalleled ability to register slight increases in capillary related edema. Early diagnosis of the capillary related edema permits the clinician to follow the progress of capillary related edema and provide the appropriate clinical response, if warranted (e.g., prescription of diuretics).

A number of medical conditions described herein can produce capillary related edema. The present invention is particularly well suited for testing capillary related edema in medical conditions that increase capillary blood pressure, increase intracapillary oncotic pressure, or increase capillary permeability. Such medical conditions include but are not limited to compromised cardiac function (particularly right ventricular failure and valvular insufficiency), compromised renal function (particularly renal failure with decreased urine production, compromised ability to concentrate urine in the distal nephron or improper glomerular filtration, hepatic failure water load (particularly the rapid administration (e.g., IV) of isotonic or isosomotic fluids) and hypertension. Table 3 shows a number of potential medical conditions and medical treatments side effects that may cause, in part or in whole, capillary related edema. Table 3 also indicates the medical conditions in which the present invention is particularly clinical relevant and extremely clinically relevant. Table 3 is by no means exhaustive, as it is only illustrative of the many clinically relevant medical settings in which the present invention can be applied.

TABLE 3

Selected Medical Conditions and Medical Treatment Side Effects That may Cause Capillary Related Edema Diabetes (secondary complications, see renal and vascular related disorders)+
Discontinuation of antihypertensive agents, cardiovascular drugs, diuretics, or anticoagulants++
Disorders resulting in increased capillary permeability++
(e.g. burn, electrical injuries, poisoning, sepsis, and systemic toxins)
Drug-induced+
(e.g. estrogens)
Heart related causes++
Heart failure secondary to myocardial infarction, myocardial ischemia, arrhythmia, valvular dysfunction, hypoxia, cardiotoxic substances, recent initiation of a β-blocking agent, myocardial infections, or pericardial effusion
Hypertensive related causes (with secondary heart failure)++
Idiopathic
Liver disease
(e.g. liver cirrhosis, hepatic failure)
Physiologic challenges++
(e.g. alcohol, altitude-induced, orthostasis, pregnancy, psychological stress, salt load, trauma, water load)
Neurogenic edema+
(e.g. after stroke, epidural, subdural, and subarachnoid hemorrhage)
Trauma++
Oncotic pressure disorders++
(e.g. hypoproteinimic states, protein-losing enteropathy, nutritional deficiency states, congenital hypoalbuminemia, and chronic liver disease)
Pulmonary related causes
(e.g. pneumonia, pulmonary embolism)
Renal related disorders++
(e.g. renal failure, nephrotic syndrome, chronic pyelonephritis, glomerulonephritis, and discontinuation of diuretics)
Vascular related disorders++
(e.g. varicose veins, and obstruction of venous drainage)

+: particularly clinically relevant; ++: extremely clinical relevant
(some of the listed disorders may be applicable to two or more of the listed categories)

A number of drugs can also produce capillary related edema. The present invention is particularly well suited for testing capillary related edema before, concurrent with, or after drug administration. Table 4 shows a number of drugs that may cause, in part or in whole, capillary related edema as a side effect. Table 4 is by no means exhaustive, as it is only illustrative of the many drugs that may cause capillary edema.

TABLE 4

Selected Drugs That May Induce Capillary Related Edema

Antidiuretic hormone (ADH)
Antimicrobial agents
(see also under "hepatotoxic drugs" and "nephrotoxic drugs")
Chemotherapeutic drugs
(see also under "hepatotoxic drugs" and "nephrotoxic drugs")
Hepatotoxic drugs and drugs causing impairment of hepatic function
(e.g. aflatoxine, antiepileptic drugs [e.g. valproic acid], antimicrobial drugs [e.g. rifampicin, fluconazole], antiviral drugs [e.g. vidarabine])
Hormones
(e.g. estrogen and estrogen derivatives)
Immunosuppressive drugs
(see also under "hepatotoxic drugs" and "nephrotoxic drugs")
Myocardial depressant agents and cardiotoxic drugs
(e.g. verapamil, disopyramide, adriamycin, and daunomycin)
Nephrotoxic drugs and drugs causing impairment of renal function
(e.g. anticancer drugs [e.g. carboplatin, carmustine, cisplatin, TABLE 4-continued Selected Drugs That May Induce Capillary Related Edema cyclophosphamide, ifosfamide, lomustine, semustine, streptozocin, and thioguanine], antimicrobial agents [e.g. aminoglycosides, amphothericin B, cephalosporines such as cephalotin, cephalexin, cefamandole, pentamidine], antiviral agents [e.g. amantidine, foscarnet], contrast agents for radiologic and other imaging procedures, immunosuppressants [e.g. cyclosporine], non-steroidal antiinflammatory drugs)
Neuro- and psychopharmacologic drugs
Salt retaining agents As a further example, the present invention may be used for the early diagnosis of or for monitoring the progression of capillary related edema in conjunction with a medical treatment. For instance, after testing for capillary related edema it may be advantageous to administer a diuretic agent, a cardiac function agent or a diabetic agent to the subject. Testing for capillary related edema can then be repeated by positioning an ultrasound probe on an appendage region of a subject in need of capillary related edema detection after the administration of an agent, and recording ultrasound signals with the ultrasound probe from the appendage region. The therapeutic value of the treatment with respect to the capillary related edema can be then assessed. This aspect of the invention can be used with a number of the medical treatments described herein, particularly those treatments affecting capillary related edema in the appendages. Table 5 shows a number of potential medical treatments that may reduce, in part or in whole, capillary related edema. Table 5 is by no means exhaustive, as it is only illustrative of the many medical treatments that can apply to capillary related edema. Selected routes of administration for various agents include: intradermal injection, subcutaneous injection, intramuscular injection, intravenous injection, intraperitoneal injection, intracavitational injection (e.g., injection into a pre-existing physiologic or pathologic body cavity), oral, anal, inhalational, nasal spray, and dermal patch. One skilled in the relevant art can easily select the route most likely to be a therapeutically effective modality for a particular agent.

TABLE 5

Selected Medications That Call Be Used To Treat Capillary Related Edema or Its Underlying Cause Anticoagulants
(for treatment of deep venous thrombosis or pulmonary embolism) (e.g. dicumarol, cumarine derivatives, heparin calcium, heparin sodium, and warfarin sodium)
Antihypertensives
Alpha-adrenergic blockers
(e.g. bunazosin, phenoxybenzamine hydrochloride, phentolamine mesylate, prazosin hydrochloride, terazosin hydrochloride, tolazoline hydrochloride, and urapidil)
Angiotensin-converting enzyme inhibitors
(e.g. benazepril, captopril, enalaprilat, enalapril maleat, fornopril, lisinopril, monopril, perindropril, quinapril, and ramipril)
Beta-adrenergic blockers
(see under "cardiovascular agents")
Calcium channel blockers
(see under "cardiovascular agents")
Centrally acting antihypertensives
(e.g. alphamethyldopa, clonidine, guanfacine, rilmenidine, and guanobenz)
Monoamine oxidase inhibitors
(e.g. pargyline hydrochloride)
Miscellaneous
(e.g. clonidine hydrochloride, diazoxide, guanabenz acetate, guanadrel sulfate, guanethidine sulfate, guanfacine hydrochloride, hydralazine hydrochloride, mecamylamine hydrochloride, methyldopa, metyrosine,

TABLE 5-continued

Selected Medications That Call Be Used To Treat Capillary Related Edema or Its Underlying Cause minoxidil, nitroprusside sodium, and trimethaphan camsylate)
Rauwolfia alkaloids
(e.g. deserpidine, rauwolfia serpentina, rescinnamine, and reserpine)
Cardiovascular agents
(see also listing for antihypertensives)
Antiarrhythmics and miscellaneous
(e.g. adenosine, amiodarone hydrochloride, bretylium tosylate, disopyramide phosphate, encainide hydrochloride, flecainide acetate, indecainide hydrochloride, lidocaine, lidocaine hydrochloride, mexiletine hydrochloride, molsidomine, procainamide hydrochloride, propafenone hydrochloride, propanolol, quinidine gluconate, quinidine, polygalacturonate, quinidine sulfate, sotalol, and tocainide)
Anticholinergics
(e.g. atropine sulfate)
Beta-adrenergic blockers
(e.g. acebutolol, atenolol, betaxolol, bisoprolol, labetalol, metoprolol tartrate, nadolol, oxprenolol, pindolol, propanolol hydrochloride, sotalol, and timolol maleate)
Calcium channel blockers
(e.g. amlodipine, diltiazem hydrochloride, felodipine, isladipine, lacadipine, nicardipine, nifedipine, nitrendipine, and verapamil hydrochloride)
Cardiac glycosides
(e.g. deslanoside, digitalis glycoside, digitoxin, digoxin, and strophantin)
Hydantoin derivates
(e.g. phenytoin sodium)
Nitrates
(e.g. nitroglycerin, isosorbide, pentaerythritol tetranitrate, and erythrityl tetranitrate)
Phosphodiesterase inhibitors
(e.g. methylxanthines)
Thrombolytics
(e.g. streptokinase, urokinase, tissue plasminogen activator (tPA), and anisoylated plasminogen streptokinase activator complex (APSAC))
Vasodilators and vasoconstrictors
(see under "Antihypertensives" and "Vasoactive Substances")
Diuretics
Aldosteron antagonists and potassium sparing diuretics
(e.g. amiloride, canrenone, spironolactone, and triamterene)
Carbonic anhydrase inhibitors
(e.g. acetazolamide, acetazolamide sodium, dichlorphenamide, and methazolamide)
Loop diuretics
(e.g. bumetanide, ethacrynate sodium, ethacrynic acid, furosemide, and torsemide)
Miscellaneous
(e.g. alcohol and caffeine)
Natural medicinal products
(e.g. terminalia arjuna and moringo oleifera)
Osmotic agents
(e.g. mannitol, glycerin and hyperosmolar solution)
Plasma expanders
(e.g. dextran)
Thiazides
(e.g. bendroflumethiazide, benzthiazide, chlorothiazide, cyclothiazide, hydrochlorothiazide, hydroflumethiazide, indapamide, methyclothiazide, polythiazide, and trichlormethiazide)
Thiazide-like agents
(e.g. chlorthalidone, metolazone, and quinethazone)
Serum albumin
Vasoactive substances
(e.g. bamethan, bencyclane, bethahistine, cyclandelate, cinnarizine, citicoline, dihydroergocristine, dihydroergotoxine, dipyridamole, ebunamonine, flunarizine, ginko-biloba extracts, horse-chestnut seed extract, isoxsuprine, naftidrofuryl, nicergoline, nicotinic aid derivatives, nylidrin, oxerutins, i.e. hydroxyethyl derivatives of rutin, pentoxifylline, papaverine, piracetam, piribedil, raubasine, suloctidil, and vincamine)

Monitoring of capillary related edema is also particularly relevant in many critical care situations including patients with acquired immunodeficiency syndrome (AIDS), autoimmune disorders, burns, bacteremia, cancer leading to local or distant organ failure, cardiac arrest, coma, drowning or near-drowning, drug-induced complications, drug overdose, heart failure, hepatic failure, infections, inhalation of toxic substances, intestinal ischemia and infarction, myocardial ischemia or infarction, poisoning, prolonged non-ambulatory convalescence, pulmonary embolism, renal failure, respiratory arrest, trauma, transplant complications, sepsis, shock, and arterial or venous thrombosis. The use of multi-site monitoring and continuous monitoring, as described in further detail herein, will be particularly applicable in this clinical setting.

Devices For Testing for Capillary Related Edema

Many aspects of monitoring or testing for capillary related edema can be performed with currently available ultrasound equipment designed for imaging. Although this approach is certainly feasible and offers the clinician the opportunity to perform such diagnostic tests using a multi-use ultrasound system, such systems are not preferred for use with the present invention. Multi-use ultrasound systems, such as those used for pelvic, abdominal, thoracic, cranial, scrotal, thyroid and other small parts, fetal and vascular ultrasound, are expensive and not tailored either at the level of the probe or signal transmission or processing to test for capillary related edema.

Preferably a dedicated ultrasound system is used to test for capillary related edema. In a dedicated system the probe can be adapted for measuring capillary related edema. The probe frequency can be selected to optimize interrogation of a selected region and to increase the sensitivity of detection of a first and second reflective layer, as described herein. Probe size can also be optimized to sample a specific area, as described herein. Signal processing can be also be optimized for this particular application as described herein. A scan probe and signals can be used to reduce cost and size of the units. Since many such dedicated systems will be designed to primarily interrogate one particular type of capillary related edema probe site, which has a well known anatomy, imaging will not be necessary and signals can be displayed as described herein.

It will be particularly desirable to provide the ability for the subject to monitor their own capillary related edema status. Many subjects may be inflicted with a chronic medical condition or involved in a long medical treatment. In these types of settings, as well as others, the invention offers systems with an ultrasound probe that is hand-held ultrasound probe and capable of self measurement of capillary related edema. Preferably, the probe is autonomous and includes the components necessary to accomplish signal processing and display. Preferably, the subject can read the display while the subject is determining their capillary edema status, Alternatively, the system can have display that is not part of the probe so that the subject can read the display while the subject is determining their capillary edema status.

In one embodiment, the ultrasound system has an extended grip that permits the human to position the ultrasound probe on the tibia region and the ultrasound system permits the human to monitor the measurement of the capillary related edema layer. In this embodiment the probe may or may not have a display. Preferably, probe frequency, shape or size, or a combination thereof, is adapted for testing capillary related edema layer between the inner surface of the skin and anterior aspect of the tibia based on at least one ultrasound signal. The system can optionally measure skin thickness as well with plurality of ultrasound signals. Preferably, the extended grip is sufficiently long that the subject can test for a capillary related edema layer in the tibia region which is about halfway between the ankle joint and the knee joint. The system can optionally include a standard subcutaneous layer thickness for the tibia region for comparison or as a diagnostic gauge, as described herein.

Calculations and Standards

Calculation and standards can be performed as described herein for other embodiments of the invention.

5.0 METHODS AND DEVICES FOR MEASURING VASCULAR PERFORMANCE

The vascular system performs essential physiological processes, including maintaining tissue fluid balance, tissue perfusion, tissue oxygenation and nutrient and metabolite transport. Although many current techniques can be used to evaluate vascular performance, such as pulse oxymetry, conventional angiography after intravascular injection of iodinated contrast agents, B-scan ultrasound imaging of vascular structures, Doppler ultrasound, computed tomography after intravenous injection of iodinated contrast agents, and magnetic resonance angiography, these techniques, unfortunately, suffer from a number of shortcomings. Many currently available techniques are either invasive, require complicated or costly procedures, or fail to account for tissue perfusion, especially capillary perfusion of a particular tissue.

One aspect of the present invention circumvents many of the disadvantages of the current techniques for evaluating vascular performance. The present invention provides for a noninvasive assessment of vascular performance that is relatively inexpensive, easily performed by a clinician (not necessarily a physician trained in ultrasound techniques), and can integrate tissue effects into the assessment, especially capillary related tissue effects. The present invention can be applied to monitoring the venous as well as the arterial system for disorders or function. For example, the invention may be applied (a) to diagnose presence or absence of vascular disorders, (b) to detect a malfunction of aspects of vascular system, (c) to differentiate disorders or malfunction of the vascular system from other causes of capillary related edema, and (d) to monitor various types of medical treatments of vascular disorders or malfunction.

Typically, a test of vascular performance, includes two basic steps: reducing or increasing blood flow (or pressure) to a tissue in a subject in need of vascular performance assessment (step (a)), and monitoring a capillary related interstitial layer thickness of the tissue (step (b)). Monitoring ILT with an ultrasound probe can be before, after or concurrent with reducing or increasing blood flow in step (a). Without providing a limiting mechanism by which the invention operates, increasing or decreasing blood flow (or pressure) to the tissue will change the physical forces on the capillaries supplying the tissue thereby affecting fluid balance in the tissue, particularly the blood pressure and amount of blood flow. By reducing or increasing the blood pressure in the capillaries, the hydrostatic gradient across the capillary cells will change and typically drive fluid from the tissue and into the capillary or fluid out of the capillary and into the tissue. By reducing or increasing the blood flow (or pressure) in the capillaries, the amount of fluid and solute transport per unit of time through the tissue will change and typically increase accumulation of tissue metabolites or decrease accumulation of tissue metabolites.

Usually a test of vascular performance will include increasing the blood flow (or pressure) to the tissue after the reducing the blood flow in step (a) and monitoring in step (b) or decreasing the blood flow (or pressure) to the tissue after the increasing the blood flow in step (a) and monitoring in step (b). By monitoring before, after or concurrent with controlled, predeteremined maneuvers that change blood flow (or pressure) to the tissue, the change in ILT can provide a diagnostic evaluation of the level of vascular performance Typically, a first controllable maneuver reduces blood flow (or pressure) controllably reduces blood flow (or pressure) to the tissue for a clinically relevant period of time in step (a). A subsequent, second controllable maneuver to increase blood flow (or pressure) and permits an increase in blood flow (or pressure) to the tissue for a clinically relevant period of time in step (a). Monitoring typically occurs after each maneuver. Alternatively, the first controllable maneuver increases blood flow (or pressure) and permits a controllable increase in blood flow (or pressure) to the tissue for a clinically relevant period of time in step (a). A second controllable maneuver reduces blood flow (or pressure) to reduce blood flow (or pressure) to the tissue for a clinically relevant period of time in step. Again, monitoring occurs after each maneuver.

For example, the first maneuver increases blood flow by the administration (e.g., local) of a vasodilator (step (a)), monitoring ILT (step (b)), then decreasing blood flow by the administration (e.g., local) of a vasoconstrictor (step (c)), then monitoring ILT (step (d)). Steps b and d may be concurrent with steps (a) and (c).

A number of physiological challenges can be used to enhance testing of vascular performance. Typically such challenges are controllable, predetermined maneuvers that result in changes to blood pressure, blood flow or blood velocity. For instance, ILT can be measured in the pretibial region before and after the subject has been standing for 15 min or longer. Prior or after such a maneuver, the subject's leg can be raised above the level of the subject's chest, for instance at an angle of about 30° or greater to reduce blood pressure in the leg. The leg can be maintained in this position for 15 min, 30 min, or longer. Monitoring can optionally occur continuously during this maneuver. ILT is typically remeasured in the same location. If non-elevated, baseline ILT is markedly greater than the ILT with leg elevation, the result is suggestive of a venous disorder, such as incompetent venous valves. If ILT is unchanged or has only slightly decreased with leg elevation, especially at shorter time frame of elevation, the result suggests that a disorder other than incompetence of venous valves or venous insufficiency is responsible for the patient's capillary related edema, such as hepatic failure.

Another potential maneuver to change blood flow or pressure is application of a tourniquet to an extremity. ILT will be measured prior to application of the tourniquet as well after, for instance at about 15 minutes, 30 minutes, and 1 hour after application of the tourniquet. Time intervals can be changed depending on the clinical situation, such as the age of the subject or suspected medical condition (e.g., to prevent deleterious side effects). Tourniquet pressure may be adjusted so that the superficial veins, such as the greater saphenous vein, are occluded. Communicating veins and deep veins, however, typically remain open. With occlusion of superficial veins, both healthy subjects as well as subjects with malfunction of vascular performance will develop capillary related edema of the extremity measured as an increase in ILT. The amount of capillary related edema and resultant measured ILT, however, will be larger in subjects with incompetent valves of the communicating veins and the deep veins, since venous drainage is even further impaired by the presence of valvular incompetence.

Additional maneuvers with application of a tourniquet or other devices can be performed at multiple different sites and with the extremity positioned above the level of the right atrial heart chamber, at the level of the right atrial heart chamber, and below the level of the right atrial heart chamber. For instance, the increase in blood flow (or blood pressure) in step (c) or (a) occurs with either 1) the tibial region elevated at a level approximately above the heart of the subject, 2) the tibial region at approximately the same level as the heart of the subject or 3) the tibial region located at a level approximately below the heart of the subject. The elevation changes in an appendage region (e.g., tibial region) can be induced by tilting the examination table to induce changes in appendage blood pressure. A tourniquet can be applied optionally to reduce blood flow. Differential effects of blood flow versus blood pressure can be evaluated using such combination maneuvers and applied to determining the type of impairment of vascular performance. Blood flow alterations are generally related to capillary impairments and arteriole impairments. Blood pressure alterations are generally related to venous impairments, as well as arteriole impairments. Evaluations of particular subjects can be cross verified to place greater clinical certainty on the diagnosis.

Additionally, maneuvers can be performed or modified using physiological challenges such as a fluid challenge with isotonic saline or using drug-induced manipulations. Other maneuvers can also be applied such as local administration of a vasodilator, invasive tamponade, gravitational challenge, rapid changes in distal limb blood pressure, and shunting (artificial and natural).

Other maneuvers can be used to diagnose malfunction of vascular performance of the arterial tree. ILT can be measured in the pretibial region prior to administration (preferably local administration) of vasoactive substances that preferentially affect the arterial system, such as hydralazine or tolazoline. ILT can then be remeasured at various time intervals after drug administration, e.g. 30 minutes, 1 hour and 2 hours later. A significant decreases in ILT after drug administration, i.e. a decrease in capillary related edema owing to improved peripheral perfusion, is indicative of a disorder of the arterial tree such as atherosclerosis. Bilateral difference can also indicate whether different branches of the tree are more or less impaired. If ILT remains unchanged, other conditions such as venous insufficiency are likely to account for the capillary related edema.

The presented maneuvers are only exemplary. One skilled in the art can easily apply many other maneuvers that can be used to diagnose the presence and severity of malfunction of vascular performance. ILT measured in patients can be compared to normal reference values for each provocative maneuver in the various anatomic regions obtained in age, sex, race, and weight-matched controls and can also be compared to the contralateral side.

In another embodiment of the invention, ultrasound measurements of ILT and capillary related edema can be used to predict the possibility of venous thrombosis. Traditionally, venous thrombosis is diagnosed using conventional venography after intravenous injection of iodinated contrast media, Doppler ultrasound interrogation of the veins, or magnetic resonance angiography. Conventional venography is invasive and as such is hampered by multiple, even fatal, side effects such as contrast reaction. Conventional venography, Doppler ultrasound, and MR angiography require advanced technical skills for image acquisition as well as subsequent interpretation. Typically, these techniques can only be performed by trained physicians. Venous thrombosis, in particular deep venous thrombosis, is associated with high morbidity and mortality. Frequent complications include pulmonary embolism and cardiorespiratory arrest. Venous thrombosis reduces or interrupts local blood flow resulting in venous stasis with increased hydrostatic gradient across capillary cells. It often occurs in patients after surgery, stroke, catheter treatments or trauma. The increased hydrostatic gradient across capillary cells will drive fluid from the capillary into the tissue with resultant capillary related edema.

Capillary related edema secondary to venous thrombosis can be diagnosed using ultrasound measurements of ILT. The presence of venous thrombosis can be suggested, if ILT is elevated and particularly elevated beyond a certain threshold value. Threshold values can be defined based on the contralateral, healthy extremity. Threshold values can also be defined on the basis of reference values for healthy age, sex, weight, and race matched control subjects in a given anatomic location. The percent change in ILT per unit time can also provide diagnostically useful information about presence or absence of venous thrombosis as well as chronicity of thrombosis which is a diagnostic dilemma for the other techniques. Ultrasound measurements of ILT have several unique advantages over Doppler ultrasound interrogation of the venous structures and conventional venography and magnetic resonance angiography. Specifically, unlike the other techniques, ultrasound measurements of ILT do not require high technical skills for diagnosing the presence of venous thrombosis. The technique is simple and can be performed by an untrained physician, a nurse, or the patient.

In one embodiment, patients at risk for venous thrombosis, e.g. patients with previous venous thrombosis or patients with coagulopathies, may perform the test by themselves using a dedicated hand-held device. The device can store results of ILT measurements and compare them to previous measurements. If the measured ILT has increased significantly when compared to previous measurements, an alarm such as a bell, a flashing light, or a message will be generated by the device and the patient will be asked to repeat the measurement. If the repeat measurement confirms the increase in ILT, the device can generate a message informing the patient to consult his physician who may then confirm the result with another diagnostic test and/or initiate medical or surgical treatment.

Ultrasound measurement of ILT may also be used to differentiate disorders or malfunction of vascular performance from other diseases such as cardiac, renal or hepatic disorders. Capillary related edema induced by malfunction of the vascular system may be more prominent at distal sites, such as the foot and calf. While capillary related edema induced by compromised hepatic function, for instance, may induce a more uniform increase at proximal and distal sites. Similarly, capillary related edema induced by malfunction of the vascular system may preferentially affect dependent body regions (regions subjected to fluid accumulation due to gravity), while capillary related edema induced by compromised hepatic function may induce a more homogeneous increase in ILT in dependent and non-dependent body portions (regions not subjected to fluid accumulation due to gravity). Furthermore, unlike capillary related edema induced by compromised hepatic function, capillary related edema induced by malfunction of the vascular system may be anatomically limited to the region with impaired vascular performance. Often additional diagnostic tests of vascular performance, as well as hepatic, cardiac and renal function, can be used in parallel with the methods described herein to cross correlate findings for improved differential diagnosis and enhances diagnosis based on integrative assessments of patient physiological function. Multi-site monitoring can also assist in pinpointing the abnormality.

In another embodiment of the invention, longitudinal ultrasound measurements of ILT, optionally in conjunction with maneuvers to change blood flow or pressure, can be used to monitor and quantify a response to a treatment of vascular performance. In subjects with a malfunction of vascular performance, ILT may be measured with ultrasound prior to initiation of a new treatment regimen, e.g. topical application of venoactive substances. ILT will then be remeasured at several intervals after initiation of treatment, e.g. 2 weeks, 4 weeks and 2 months later. If ILT has decreased significantly when compared to the baseline value, the result indicates that treatment is effective and should be continued. If ILT is not significantly changed, the result is indicative of treatment failure and treatment should be changed. In this fashion, longitudinal ultrasound measurement of ILT and assessment of capillary related edema can be used (a) to improve subject management and improve the patient's quality of life, and (b) to decrease health care costs by identifying ineffective treatment modalities and discontinuing them early. Medical treatments will typically include cardiovascular agents. Such measurements will be particularly important with subjects diagnosed with hypertension or diabetes.

Another particularly interesting aspect of testing vascular performance relates to the effect of weightlessness and gravity on the physiology of mammals, particularly humans. Continuous monitoring of air and space traveling subjects is a desirable feature of the invention. For air travel, particularly fighter pilots that are subjected to intense G-forces, continuous monitoring of ILT can be applied. Optionally, fluid shifts can be part of a feedback system that would increase externally applied pressure to tissues using a flight suit with a mechanical pressure means. For space travel ultrasound monitoring of ILT can indicate critical times to take precautionary measures to minimize fluid shifts or changes in vascular performance.

Depending on the clinically relevant time period for these applications, ultrasound measurements of ILT may be performed at a single time point, at time intervals of at least about 15 minutes, at time intervals of several days, or at time intervals of several weeks. Additionally, diagnostic information may be enhanced by measuring ILT prior to and after maneuvers or physiological challenges. Presence of a vascular disorder or malfunction of vascular performance can be diagnosed using ultrasound measurement of ILT at a single time point. If ILT in a given anatomic location, such as the pretibial region, is elevated above the reference value (e.g. that of age, sex, race, or weight-matched controls), presence of a malfunction of vascular performance is suggested. This is a particularly strong diagnosis if the subject has no clinical or laboratory findings or diagnosis indicating an underlying cardiac, renal, hepatic or other non-vascular disorder.

Tests of vascular performance can be conducted using either A scan or B scan devices. For dedicated systems for tests of vascular performance A scan is preferred. Typically, such devices can detect a 15% or less change in interstitial layer thickness. Preferred embodiments for detecting ILT for this application can be ascertained by examining other embodiments of the invention described herein. Preferably, the ultrasound probe is adapted to measure interstitial layer thickness. Preferably, the monitoring can detect about a 1% or more change in leg diameter arising from changes in interstitial layer thickness.

Another aspect of the present invention is the assessment of vascular performance in disorders with pathologically increased capillary permeability. Pathologically increased capillary permeability can be observed in a large number of disorders such as bacteremia, burns, electric injury, exposure to systemic toxins, poisoning, or sepsis. Increased capillary permeability is another cause of capillary related edema.

Ultrasound measurements of ILT provide information on (a) the presence of capillary related edema in patients with pathologically increased capillary permeability, (b) the severity of capillary related edema, (c) response to treatment of pathologically increased capillary permeability or response to treatment of the underlying condition, and (d) changes in capillary permeability due to physiologic or pharmacologic interventions.

Presence of capillary related edema can be diagnosed in patients with pathologically increased capillary permeability, if ILT at a given anatomic site such as the pretibial region is elevated above a reference value (e.g. that of age, sex, race, or weight-matched controls). The severity of the pathologic increase in capillary permeability can be assessed using ultrasound measurements of ILT. Slightly elevated values of ILT when compared to an age, sex, race, and weight-matched healthy reference population indicate a mild increase in capillary permeability. High ILT values at a given anatomic site are indicative of a severe increase in capillary permeability. A severe increase in capillary permeability can lead to intravascular volume depletion and hypovolemia with resultant shock and possible cardiorespiratory arrest. The risk of severe intravascular volume depletion and hypovolemia in patients with pathologically increased capillary permeability can be assessed by comparing ultasound measured ILT with reference values of healthy control subjects and by analyzing changes in ILT of the individual patient longitudinally over time.

Patients who are being treated medically for disorders resulting in pathologically increased capillary permeability can be monitored using ultrasound measurements of ILT. ILT is measured with ultrasound prior to initiation of therapy. ILT is then remeasured at several intervals after initiation of treatment. A decrease in ILT during medical treatment indicates a decrease in abnormal capillary permeability either secondary to successful treatment of the underlying condition or of abnormal capillary permeability. If ILT does not change signficantly during treatment, treatment of the underlying condition or of increased capillary permeability is ineffective and another therapeutic approach should be chosen.

Multiple new drugs, hormones, tissue and blood factors, and other substances are currently being developed that can alter capillary permeability. These include but are not limited to tumor necrosis factor, vascular endothelial growth factor, and substance P. Additionally, other treatments such as hyperthermia and radiation therapy are available that can modulate capillary permeability. Ultrasound measurements of ILT provide a diagnostic gauge to evaluate changes in capillary permeability in subjects treated in such fashion. If ILT increases, the increase is an indication of increased capillary permeability. Conversely, decreases in ILT indicate decreased capillary permeability, possibly due to modulation of the capillary endothelial wall. The amount of change in ILT provides a quantitative measure for the amount of change in capillary permeability induced by the treatment. Such information is clinically extremely useful in evaluating new therapies that can decrease or, if clinically desirable, increase capillary permeability.

In another embodiment of the invention, increased capillary permeability can be measured directly by injecting intravenously ultrasound contrast agents, e.g. particles carrying microbubbles, of sizes large enough not to cross normal capillary endothelial membranes but small enough to cross capillary endothelial membranes with pathologically increased permeability. Once such an agent has crossed the endothelial membrane, it will alter local tissue echogenicity.

These changes in echogenicity reflect the degree of capillary permeability and can be used to evaluate or quantitate the amount of capillary leakiness. Such measurements alone or in combination with ultrasound measurements of ILT, possibly before and after reducing or increasing blood flow or pressure, can provide assist in diagnosing between capillary related edema due to oncotic affects versus capillary permeability effects. Such clinical insights into the pathophysiological mechanisms of various diseases and disorders with pathologically increased capillary permeability or capillary related edema can be used to guide therapy.

6.0 METHODS AND DEVICES FOR EVALUATING CARDIAC PERFORMANCE

Heart failure can often lead to decreased cardiac output or increased systolic and/or diastolic pressures that induce systemic effects. Among these systemic effects is edema, especially capillary related edema. Capillary related edema due to heart failure can lead to deleterious systemic effects, such as tissue ischemia, capillary breakdown, and, in extreme instances, necrosis of tissue subjected to prolonged or sudden ischemia.

Current methods of evaluating cardiac performance focus on direct measurements of cardiac function. Methods include auscultation, EKG, myocardial scintigraphy, exercise stress test (e.g., EKG measurements in the absence or presence of exercise), other forms of stress test (e.g. EKG or myocardial scintigraphy after injection of dipyridamole, adenosine, or other cardiac drugs) catheter related techniques (e.g. right heart catheterization such as Swan-Gantz catheter methods, wedge pressures, and cardiac output and flow studies, left heart catheterization, and measurements of ejection fraction) and imaging techniques (e.g., MRI, CT, and ultrasound). While such techniques enjoy a large measure of success in many subjects, these techniques focus in on the heart, rather than on the heart as an integrated component of the circulatory system or as a key component in the physiological process of regulating fluid balance. Currently, no techniques are available for evaluating cardiac performance as a component of systemic fluid balance.

The inventors, for the first time, present a method of evaluating cardiac performance associated with, or as a function of, capillary edema or interstitial fluid balance. Because heart function is intimately associated with, and modified by, systemic effects, it can be advantageous to test for, or monitor, capillary related edema. The present invention offers a number of advantages that can reduce health care costs, improve patient quality of life and provide for more reproducible and facile tests of cardiac function. Testing for capillary related edema or monitoring ILT can provide early signs of cardiac failure. Testing for capillary related edema or monitoring ILT can also be combined with current techniques of cardiac function to provide a powerful diagnostic tool that evaluates the heart both as an isolated component and as an integrated component of maintaining fluid balance. Described herein for the first time are a number of techniques that alter cardiac function and monitor its affect on fluid balance, both short and long-term effects of dynamic cardiac performance can be evaluate&

Heart failure refers to the pathophysiologic state in which an abnormality of cardiac function is responsible for the failure of the heart to pump blood at a rate commensurate with the requirements of the metabolizing tissues and/or in which the heart can do so only from an abnormally high filling pressure. Without providing a limiting mechanism by which the invention operates, the inability to pump a sufficient amount of blood per unit time or a compromised cardiac output can lead to capillary related edema. Because tissues may receive insufficient blood flow in the early stages of heart failure, capillary related edema can occur due to a variety of effects including ischemic tissue damage, increased afterload, capillary breakdown due to an increase in tissue metabolites, or tissue acidosis. By testing for capillary related edema or monitoring ILT, early signs of heart failure can be detected prior to or during compensatory adjustment of heart function, which can ultimately lead to irreversible and often deleterious effects on heart muscle. Once the heart attempts to compensate for insufficient blood flow to the systemic tissue by pumping more blood less efficiently, the ventricular performance begins to decline and capillary related edema can actually intensify.

Multiple myocardial and non-myocardial disorders and conditions can lead to heart failure. These include, but are not limited to, myocardial infarction, myocardial ischemia, myocardial infections, arrhythmias, valvular dysfunction, hypoxia, cardiotoxic substances, pericardial effusion, hypertension, recent initiation of a β-blocking agent, and discontinuation of antihypertensive agents, cardiovascular drugs, diuretics, or anticoagulants. Such heart disorders can lead to abnormally high filling pressures that can result in systemic increases in capillary pressure.

Right heart failure causes an increase in venous pressure and venous distension in the superior and inferior vena cava and the peripheral venous system with resultant venous stasis and elevated intracapillary pressures. Elevated capillary pressure increases the hydrostatic gradient for fluid movement out of the capillaries and the elevated pressure increases the capillary permeability to large molecular weight molecules. Either condition or both can lead to capillary related edema.

Left heart failure can cause decreased renal perfusion resulting in decreased glomerular filtration and urinary excretion, as well as fluid retention. Patients in whom the left ventricle is mechanically overloaded or weakened develop dyspnea and orthopnea as a result of pulmonary vascular congestion and, ultimately, pulmonary edema. When left heart failure is more chronic and has existed for months and years, patients will often develop ankle edema, congestive hepatomegaly, or systemic venous distension, i.e. signs and symptoms of right heart failure, even though the abnormal hemodynamic burden was initally placed on the left ventricle. This is in part the result of secondary pulmonary hypertension and resultant right-sided heart failure but also because of the persistent retention of salt and water.

Ultrasound measurements of ILT can be used to (a) diagnose presence of capillary related edema in patients with heart failure, (b) assess the severity of capillary related edema in patients with left and right ventricular failure, and (c) monitor response to treatment of heart failure, e.g. with positive inotropic or chronotropic drugs or diuretics.

The presence and severity of capillary related edema can be assessed in patients and can lead to the early diagnosis of progressive heart failure. For instance, if ILT at a given anatomic site such as the anterior tibial region is elevated above the reference value of a healthy reference population (e.g., an age, sex, race, or weight-matched healthy reference population) heart failure is implicated. Typically, the patient will then be subjected to additional tests of cardiac function either separately or in conjunction with ILT measurements. Slightly elevated values of ILT can be compared to historic records of the same patient or when compared to a healthy reference population (e.g., an age, sex, race, and weight-matched healthy reference population) may indicate mild heart failure. High values of ILT values at a given anatomic site are indicative of more advanced and severe heart failure.

Changes in cardiac function can be assessed by longitudinal or continuous monitoring of ILT at different anatomic sites. Often, the patient will be suspected of having a medical condition that compromises heart function or is need of heart function testing.

In another embodiment of the invention, ultrasound measurements of changes in ILT over time can be used to diagnose progression of heart failure from a compensated to a decompensated state. Such information is clinically useful in many situations, e.g. hospitalized patients after myocardial infarction with heart failure or patients with chronic heart failure. For example, if ILT increases above a certain threshold value, this change can be indicative of decompensation of cardiac function which can indicate a serious threat to the patient's life. Threshold values can be defined by comparing measured ILT at a given time point with the patient's baseline ILT, e.g. ILT measured at the time of hospital admission or at the time of a previous outpatient visit. Threshold values can also be defined by comparing measured ILT at a given time point with the patient's baseline ILT and/or normal reference values of ILT (e.g. ILT values in an age, sex, race, or weight-matched healthy reference population). ILT can be measured continuously or in an intermittent fashion, e.g. every 30 minutes or at intervals greater than 1, 2, 5, and 24 hours. Threshold values in evaluating changes in ILT can also be based on the calculation of the slope of the curve of ILT plotted against time or of the slope of the curve of change in ILT plotted against time. The slope of the ILT-time-curve or the ΔILT-time-curve can yield useful diagnostic information on progression of heart failure from a compensated to a decompensated state. One skilled in the art will readily recognize substitute methods and equations for assessing changes in ILT.

By monitoring such changes in ILT, systemic effects of cardiac performance can be assessed continuosly or during clinically relevant time periods. Unlike other cardiac monitoring techniques, such as EKG methods, ILT changes provide an assessment of the ability of cardiac performance to adequately maintain systemic tissue perfusion. For instance, continues EKG monitoring may provide information concerning damaged heart tissue, or comprised electrical conduction, however, the clinician can only infer the systemic effects of such compromised heart function. In the present invention, the monitoring of compromised heart function provides additional information on the heart's ability to supply tissues with sufficient amounts of blood to prevent or minimize tissue perfusion effects, such as metabolite build up, insufficient oxygenation or insufficient nutrient delivery.

In addition, because ILT can be exquisitely sensitive in monitoring rapid or small changes, changes in cardiac function may be detected systemically by changes in ILT before changes in EKG or other techniques demonstrate a clinically important change. For example, a small change in EKG pattern might be readily detectable, but go unnoticed. The effect of such a change on the patient's homeostasis may often not be detected clinically. Such a change, however, may lead to systemic effects that will complicate the patient's homeostasis or be indicative of progressive effects systemically. Such a small change in heart function may negatively synergize with other bodily functions (e.g. respiratory, renal or hepatic functions) that manifest in an increase in ILT but not a direct measurement of cardiac function. ILT changes may occur prior to a clinically definable intervention point based solely on a measurement of cardiac function (e.g., EKG). Consequently, the present invention can detect changes in cardiac function that are useful in defining a clinical intervention point, particularly a clinical intervention point defined in advance of changes in cardiac function detected using measurements of cardiac function alone.

The invention also provides for self-assessment of capillary related edema in patients with chronic heart failure using hand-held or automated monitoring ultrasound devices. If ILT increases above a predefined threshold value or at an accelerated rate exceeding a predefined range of clinically acceptable values of change in ILT over time, the device may alert the patient and/or the physician with an alarm such as a bell, a flashing light, or a message indicating that the patient is at risk for decompensation of heart failure.

In another embodiment, the invention provides for risk assessment of pulmonary edema in patients with left heart failure. As outlined above, patients with left heart failure will often develop capillary related edema. The severity of capillary related edema is directly related to the severity of heart failure. For example, if ILT increases above a certain threshold value, this change can indicate an increased risk for pulmonary edema or, if high enough, can be indicative of the development of pulmonary edema.

The slope of the curve of ILT plotted against time or change in ILT plotted against time can also provide useful information for assessing the risk of pulmonary edema. If the slope of the ILT-time-curve or the ΔILT-time-curve exceeds a predefined value, the patient is at increased risk for pulmonary edema. This information is extremely useful in situations where it is difficult to monitor the patient's cardiac function closely, e.g. during surgery, or in situations where frequent or continuous monitoring is required.

Another embodiment of the invention includes a method for non-invasively estimating dynamic cardiac performance in a human, comprising: (a) monitoring capillary related interstitial fluid content with an ultrasound probe positioned on the skin of a human in need of such monitoring and in a region suitable for monitoring changes in capillary related interstitial fluid content during a clinically relevant time period and (b) measuring capillary related interstitial fluid content prior to and after pharmacologic interventions, exercise, and other current and future types of stress induction designed to evaluate cardiac performance. If ILT is measured in conjunction with cardiac stress testing, changes in ILT can be compared to reference values obtained from a healthy reference population (e.g., an age, sex, race, and weight-matched healthy reference population). Impairment of cardiac function is diagnosed if changes in ILT exceed a predefined reference range. Testing of dynamic cardiac performance using ultrasound measurements of ILT prior to and after stress induction can also be used to evaluate the patient's risk for progressing from a compensated to a decompensated state of heart failure.

Calculations and Standards

Calculations and Standards can include those described herein, known in the art or developed in the future. Standards can be used to qualitatively or quantitatively compare capillary related interstitial fluid content to a predetermined standard value for capillary related interstitial fluid content, wherein the comparison provides a useful diagnostic measure of cardiac performance.

7.0 METHODS AND DEVICES FOR MEASURING RENAL DISORDERS AND FUNCTION

Compromised renal function can be observed with multiple disorders, such as urinary obstruction, vasculitides, diabetes, glomerulonephritis, interstitial nephritis, chronic pyelonephritis, ischemic kidney damage, or, in transplant patients, transplant malfunction, e.g. from transplant rejection. Compromised renal function will lead to electrolyte disturbances and fluid retention resulting in capillary related edema. The present invention can be applied to monitoring the renal system for disorders or to evaluating renal function. For example, the invention may be applied (a) to diagnosing presence of capillary related edema in patients with compromised renal function, (b) to assess the severity of capillary related edema, and (c) to monitor a subject's response to the treatment of compromised renal function or capillary related edema, e.g. diuretic therapy.

Presence of capillary related edema can be diagnosed in patients with compromised renal function, if ILT at a given anatomic site such as the anterior tibial region is elevated above the reference value (e.g. the values in age, sex, race, or weight-matched controls). Ultrasound measurements of ILT provide also information on the severity of the compromise of renal function. Slightly elevated values of ILT when compared to a healthy reference population indicate mild compromise of renal function. High values of ILT values at a given anatomic site are indicative of severe compromise of renal function. The risk of acute renal failure and anuria can be assessed by comparing ultrasound measured ILT with reference values of healthy control subjects (or historic values from the same patient) and by analyzing changes in ILT of the individual patient longitudinally over time. To enhance distinguishing between renal failure and compromised cardiac of vascular performance, ILT can be measured in the face of different physiological challenges as described herein for different organ systemsRenal function can be further assessed by measuring ILT prior to and after physiologic challenges, such as saline administration and/or administration of drugs such as angiotensin converting enzyme inhibitors or antidiuretic hormone. Reference values for changes in ILT following such physiologic challenges and/or drug administration obtained in healthy control subjects (e.g., age, sex, race, and weight-matched healthy control subjects) can be compared to the change in values measured in a patient. If the change in ILT measured in the patient differs significantly from the change in the reference population, it is a diagnostic indicator of compromised renal function. The difference in change in the patient and change in the reference population is a diagnostic gauge of the severity of impairment of renal function. Furthermore, the rate of change of ILT post-administration of IV saline or isoosmotic solution can give a further indication of renal function. If ILT changes rapidly, especially in nondependent sites, due to such maneuvers impaired renal function is suggested.

Patients who undergo medical treatment of compromised renal function can be monitored using aspects of the present invention. ILT can be measured prior to initiation of therapy, e.g. diuretic therapy. ILT can then be remeasured at several intervals after initiation of treatment, e.g. 2 weeks, 4 weeks and 2 months later. A decrease in ILT during medical treatment indicates improvement in renal function and/or successful diuretic treatment. If ILT does not change significantly during treatment, therapy is ineffective and another therapeutic approach should be considered.

Noninvasive ultrasound measurements of ILT are particularly advantageous when frequent monitoring of the status of kidney function is necessary as is often the case in patients with compromised renal function. In this setting, ultrasound measurements of ILT may help avoid frequent blood draws for laboratory analysis of renal function, since treatment can be tightly monitored by following ILT. Furthermore, ultrasound assessment of ILT in conjunction with laboratory tests and urine output can provide a more complete and physiologic assessment of renal function than was previously possible.

Continuous or intermittent ultrasound monitoring of ILT is particularly useful in dialysis patients. Frequently, excess plasma fluid is removed during dialysis, in particular hemodialysis. However, if too much fluid is removed or fluid is removed too rapidly, patients can develop hypovolemia with the potential for shock and cardiorespiratory arrest. ILT can be monitored at intervals of approximately 15 minutes for the duration of dialysis and an observation period of 1–2 hours after dialysis. If ILT decreases below a certain threshold value defined based on the baseline value of the patient's ILT measured immediately prior to dialysis or if ILT decreases at an accelerated rate greater than a predefined maximum value of change in ILT per unit time, the device may alert the patient and/or the physician with an alarm such as a bell, a flashing light, or a message indicating that the patient is at risk for hypovolemia.

Similarly, if infusion or transfusion therapy or other types of treatment with intravenous fluid administration is performed in renal patients as well as patients with other disorders, ultrasound measurements of ILT can be obtained to monitor the patient's fluid balance closely. In this setting, ILT will be measured prior to initiation of intravenous treatment and at intervals of approximately 15–30 minutes after initiation of therapy. If ILT increases above a certain threshold value defined based on the baseline value of the patient's ILT measured immediately prior to treatment or if ILT increases at an accelerated rate exceeding a predefined maximum range of change in ILT per unit time, fluid administration has to be slowed down or discontinued or the patient has to be treated with a diuretic drug in order to avoid complications of overhydration such as pulmonary edema. Continuous or intermittent measurements of ILT during intravenous fluid administration can also be used to estimate the risk of pulmonary edema.

In another embodiment of the invention, patients with chronic compromise of renal function, e.g. patients with diabetes mellitus or dialysis patients, can monitor ILT at home on a daily basis using a dedicated hand-held ultrasound device. The device can store results of ILT measurements and compare them over a period of several months. If the measured ILT has increased significantly when compared to previous measurements, an alarm such as a bell, a flashing light, or a message will be generated by the device and the patient will be asked to repeat the measurement. If the repeat measurement confirms the increase in ILT, the device can generate a message informing the patient to consult his physician who may then intensify medical treatment.

Ultrasound monitoring of ILT can also be used to monitor renal transplant function both in the early postoperative period as well as days, weeks, months, and years after successful transplantation. ILT measurements can be used to identify transplant complications such as acute or chronic rejection and other forms of transplant compromise.

8.0 METHODS AND DEVICES FOR MEASURING HEPATIC DISORDERS AND FUNCTION

Compromised hepatic function is a common cause of capillary related edema. The liver is an important site of biomolecule metabolism and synthesis, such as protein synthesis of albumin. Plasma albumin is the most abundant circulating protein. Albumin contributes significantly to the plasma colloid osmotic pressure. One of the clinically most important derangements in protein synthesis is the development of hypoalbuminemia and hypoproteinemia. This results largely from reduced hepatic synthetic activity due to decreased number of hepatocytes as well as decreased function of hepatocytes. Although synthetic activity may also be reduced as a result of a decrease in dietary supply of amino acids, compromised hepatic function and hepatic failure is the most important cause for hypoalbuminemia and hypoproteinemia.

The present invention is ideally suited for measuring capillary related edema resulting from compromised hepatic function. As hepatic function deteriorates, hypoalbuminemia and hypoproteinemia will increase resulting in a decrease in plasma colloid osmotic pressure and an increase in capillary related edema and ILT. Ultrasound measurements of ILT can be used (a) to diagnose the presence of capillary related edema in patients with compromised hepatic function, (b) to differentiate capillary related edema resulting from compromised hepatic function from other causes of edema, and (c) to monitor response to treatment of capillary related edema in patients with compromised hepatic failure.

Capillary related edema induced by compromised hepatic function may induce a relatively uniform increase in ILT at proximal and distal sites, while capillary related edema induced by malfunction of vascular performance may preferentially affect distal sites. Similarly, capillary related edema induced by compromised hepatic function may induce a relatively uniform increase in ILT in both dependent (regions subjected to fluid accumulation due to gravity) and nondependent (regions not subjected to fluid accumulation due to gravity) body regions, while capillary related edema induced by malfunction of vascular performance may preferentially affect dependent body regions or may be limited to anatomic regions with impaired vascular performance. Such information can be used to differentiate capillary induced edema resulting from compromised hepatic function from that resulting from impaired vascular performance.

Information on regional distribution of edema can be particularly useful in patients who suffer from both impaired vascular performance, e.g. venous insufficiency, and compromised hepatic function. In these patients, ultrasound measurements of ILT may be particularly advantageous since differences in regional distribution of edema may help identify the cause of the edema and treatment may be directed towards the primary cause of capillary related edema. One skilled in the art can readily recognize other methods and techniques how information on regional distribution and accumulation of capillary related edema can be exploited to obtain additional diagnostic information in patients with hepatic and other disorders.

Patients who undergo medical treatment of compromised hepatic function can be monitored using ultrasound measurements of ILT. A decrease in ILT during medical treatment indicates improvement in hepatic function and improved synthesis of hepatic proteins with resultant increase in plasma colloid osmotic pressure. In this setting, ultrasound measurements of ILT provide an effective and cost-efficient means of assessing improvement in hepatic function thereby obviating the need for expensive repeat laboratory analysis of serum albumin.

Similarly, ultrasound measurements of ILT can be advantageous in patients who have undergone liver transplantation. During the early phase after transplantation, ILT should continuously decrease as capillary related edema decreases and resolves with reconstitution of normal or near normal hepatic function. Transplant complications resulting in impaired hepatic function, such as chronic transplant rejection, may in turn be detected by an increase in ILT.

9.0 METHODS AND DEVICES FOR MULTISITE MONITORING

The invention provides for the first time methods and devices for multisite monitoring of different anatomical regions either concurrently or at predetermined time intervals. Monitoring anatomical changes during clinically relevant time periods or continuous monitoring provide an important diagnostic tool for detecting short or rapid changes in tissue structure, particularly interstitial layer thickness. In contrast to previous work, the invention is able to measure rapid changes in ILT and monitor ILT from different anatomical regions simultaneously or within short time frames to compare ILT from different regions.

In one aspect, the invention provides for a method of multisite monitoring of ILT. The method comprises transmitting an ultrasound pulse from a first ultrasound probe to a first anatomical region and transmitting an ultrasound pulse from a second ultrasound probe to a second anatomical region. The method includes recording ultrasound signals from a first ultrasound probe to a first anatomical region and recording ultrasound signals from a second ultrasound probe to a second anatomical region. The method also includes monitoring interstitial layer thickness from the first and second anatomical regions. The order of the transmitting, recording and monitoring from different regions can be sequential, intermixed, continuous or a combination thereof or any other sequence that permits monitoring. Typically, the method is practiced by monitoring from the first anatomical region concurrently with monitoring from the second anatomical region.

Transmitting steps can be sequentially performed. For example transmitting from one probe is within about 10 seconds of transmitting from another probe. Transmitting is usually automatically controlled by a computational unit in a ultrasound system or chip. The method steps often are repeated over time to monitor changes in tissue structure. Typically, the steps of transmitting and recording are repeated about every 30 to 600 seconds. Monitoring can be concurrent or at preselected time periods.

The first and second ultrasound probes can be micro-transducers, as described herein. Any other suitable probe known in the art or developed in the future or described herein can also be used. Often the method will include the use of three, four or more probes. The use of multiple probes enables comparing interstitial layer thickness from the first and second anatomical regions or more regions. Concurrent comparisons provide valuable information on fluid shifts in the body. By monitoring such shifts, the clinician can address the situation with the appropriate action. The method also includes determining the rate of change over time of an interstitial layer thickness from two or more anatomical regions. Such methods are particularly sensitive and give diagnostic indications of rapid fluid shifts.

The multi-site monitoring can taken place over a variety of time frames as described herein for various indications and other methods. Typically, the time frame is hours to days. Often the micro-transducers of the invention are secured to the skin for continuous monitoring during at least about a 1 to 24 hour period. Many anatomical regions can be used such the regions described herein. Preferably, the anatomical region is selected from the group consisting of the forehead region, anterior tibia region, foot region, distal radius region, elbow region, presternal region and temporal bone region. Micro-transducers or other probes can be secured to the skin over such regions for continuous monitoring during a clinically relevant time period.

The sites listed in Table 1 and shown in FIGS. 3 and 4 can also be used in combination. By using combinations of probe sites (i.e. multisite monitoring), fluid movement throughout the body can be monitored. This permits monitoring fluid shifts from fluid compartments of the body. Multisite monitoring also permits exquisitely sensitive monitoring of physiological processes related to capillary related edema, such as processes that either induce, prevent or reduce capillary related edema, as well as therapeutic treatments thereof. The invention includes multisite monitoring of interstitial fluid during space flight. The invention includes multisite interstitial fluid monitoring for 1) blood in either blood vessels or blood released in a potential fluid space of the body (e.g., the subarachnoid, subdural, epidural, or pleural space) by a traumatic, abrupt or accidental lesion (including an aneurysm) of a blood vessel, 2) ascites in the intraperitoneal cavity, 3) fluid in the pleural space (e.g., pleural effusion), 4) fluid in the fetus and 5) fluid in the pericardium, usually blood or pericardial effusion. Different sites on the body can be used as a clinical measure of changes in various physiological states. By comparing values from different sites, assessment of fluid shifts between different fluid compartments can be evaluated.

Another aspect of the invention includes a multi-probe set that may be used for multi-site monitoring methods described herein. The multi-probe set comprises a first ultrasound probe comprising a first output port, the first ultrasound probe adapted for continuous or in situ monitoring at a first anatomical region and a second ultrasound probe comprising a second output port, the second ultrasound probe adapted for continuous or in situ monitoring at a second anatomical region. The set can include an ultrasound system to concurrently process first signals from the first ultrasound probe and second signals from the second ultrasound probe. Systems with more probes can also be used. Each probe in the set can be adapted for a particular anatomical region or indication. For example, the anatomical region can be selected from the group consisting of the forehead region, anterior tibia region, foot region, distal radius region, elbow region, presternal region and temporal bone region. Preferably, the ultrasound probe is a micro-transducer adapted for monitoring interstitial layer thickness. Additional probes can be added to the system or supplied as a kit with multi-probes that includes directions for use and appropriate packaging. The multi-probe set, for example, can include a third ultrasound probe comprising a third output port, said third ultrasound probe adapted for continuous or in situ monitoring at a third anatomical region. The multi-site methods, as well as multi-site probe sets, may be used with other methods known in the ultrasound art, such as Doppler based measurements, speed of sound measurements, imaging measurements (including ultrasound imaging for surgical procedures (e.g., trocar assisted surgery)), echogenicity measurements and ultrasound measurements using contrast reagents.

10.0 ULTRASOUND PROBES FOR IN SITU MEASUREMENTS

The invention provides for the first time micro-transducers for ultrasound measurements and imaging. Typically, the micro-transducers are adapted for either monitoring capillary related ILT or capillary related edema, usually on the skin in a predetermined anatomical region. As described herein, the micro-transducers are typically small about 10 to 20 mm$^2$ or less in surface area, not hand-held but rather attachable to the skin surface, and light weight. Preferably, micro-transducers are isolated and not connected to an ultrasound system or display by a conductive wire, as described herein. In use, the micro-transducers are usually secured to the skin of a subject for continuous monitoring of the interrogated region.

The size and shape of the micro-transducer can be sculpted to maximize the ability of the micro-transducer to detect the desired signals in a particular anatomical region. In the case of monitoring capillary related ILT, the size of the micro-transducer is generally considerably smaller than the anatomical region to be interrogated. As the size of the cross sectional area of the micro-transducer increases, a larger area is monitored, which in some applications is desirable because a greater surface area can produce better signal averaging. If the micro-transducer surface, however, is larger than the anatomical region to be interrogated the signal quality will diminish. A smaller cross sectional area also increases the selectivity of interrogation to a specific area. Consequently, micro-transducer size is generally tailored to fit a particular anatomical region. In some applications it will also be desirable to have a micro-transducer that specifically interrogates a smaller region in order to improve sensitivity. In some anatomical regions, such as the tibial region, a focused interrogation, in terms of surface area, can permit more sensitive measurements. Typically, the ultrasound micro-transducer has a surface area of no more than about 3 cm$^2$, preferably about 3 cm$^2$, and more preferably about 2 cm$^2$.

The micro-transducer may also be adapted to snugly fit a particular anatomical region. While a flat, planar and relatively stiff micro-transducer is desirable in many applications and easy to manufacture, other shapes and flexibility properties find application with the present invention. Micro-transducers may be disposed with a curved surface to either aid in capturing a better ultrasound recording or aid in securing the micro-transducer to the skin or both. For instance, in the anterior tibial region, a micro-transducer can be slightly curved to aid in fixing the micro-transducer to the skin of the leg or to aid in providing a better geometric arrangement for transmitting or receiving signals. The crystals of the micro-transducer may only be disposed over a portion of the micro-transducer surface. Micro-transducers may be disposed with a flexible housing or surface to permit the micro-transducers to be slightly "bent." The flexible nature of the micro-transducers preferably allows the housing or surface to be bent and the induced bend to be maintained, especially in embodiments where the micro-transducers may be contoured to a particular skin surface. In other embodiments, a flexible micro-transducer housing that returns to its original shape are preferred for applications where the surface needs not to be contoured but the micro-transducer might be subjected to accidental mechanical deformation by either the subject or the operator. Plastics known in the plastic art can be used for either application. Shortest reflective distance techniques can also be applied to accommodate varying angles that may be induced by non-planar micro-transducer surfaces.

The micro-transducer interrogation frequency can be selected to match the interrogated tissue. As the interrogation frequency of the micro-transducer decreases, generally, the ability to resolve reflective surfaces at deeper depths improves. At fairly deep interrogation depths (e.g., greater than about 20 to 30 mm) shorter frequency micro-transducers are desirable (e.g., about 5 to 15 MHz). Even shorter frequency micro-transducer, are desirable for interrogating particularly thick tissues (e.g., extremely thick appendages or large subjects), such as 0.5 to 3 MHz micro-transducers.

As the tissue thickness increases, a relatively small change in ILT (e.g., about 0.5 mm) will become a smaller percentage of total ILT. This can lead in some instance to decreases in the signal-to-noise ratio and make it more difficult to determine ILTs at deep interrogation depths. In such instances, as well as others, it will be desirable to provide a tunable micro-transducer that can transmit multiple micro-transducer frequencies. The micro-transducer can then either be adjusted by the operator to use the best frequency for the interrogation depth selected or the micro-transducer or the ultrasound system to which it is electrically coupled can automatically adjust the micro-transducer to the best frequency. For instance the micro-transducer can be designed with four ultrasound sources with different basic frequencies and the micro-transducer or the ultrasound system to which it is connected can provide a micro-circuit to switch to the appropriate ultrasound source based on the type or quality of signals being received. Preferred frequencies include about 1, 3 and 5 MHz.

A higher micro-transducer frequency, in general, will improve micro-transducer interrogation of shallow interrogation depths (e.g., about 1 to 30 mm). Generally, micro-transducers above 18 MHz are preferred (e.g., about 20 to 30 MHz) for shallow interrogation depths. Most of the micro-transducers with these frequencies are for monitoring capillary related ILT in anatomical regions where bone is very close to the skin, such as in small, and often thin, subjects (particularly younger subjects) and in the head or the cranium. Even in the tibial regions, however, where bone can be relatively close to the skin, especially in thin legged subjects, other interrogation frequencies will be desirable. Consequently, it will be desirable to match micro-transducer frequency to the tissue depth or anticipated depth of interrogation to improve the sensitivity of monitoring or testing.

Generally, micro-transducers can be constructed that are extremely sensitive. Micro-transducers can typically detect percentage changes in capillary related ILT on the order of about 10 percent or higher, preferably about 5 percent or higher, and more preferably about 1 percent or higher. Consequently, with shorter clinically relevant time periods it is desirable to provide high sensitivity micro-transducers in order to detect small changes in ILT over time. Such micro-transducers are particularly applicable to multi-site monitoring, continuous monitoring, and critical care monitoring.

Typically, a micro-transducer can measure changes in a capillary related ILT as small as about 0.2 to 1.0 mm. Smaller and larger changes in ILT can also be measured. Preferably, a universal micro transducer can measure changes in capillary related ILT across a broad range of thicknesses of about 0.5 to 50 mm, more preferably about 0.2 to 80 mm and most preferably about 0.2 to 120 mm. Preferably, an anatomical region specific micro transducer can measure changes in capillary related ILT across a selective range of thicknesses at a specific interrogation depth range. Such micro-transducers can measure changes in thickness of about 0.2 to 30 mm at an interrogation depth of about 1 to 50 mm, about 0.4 to 50 mm at an interrogation depth of about 2 to 75 mm and about 1 to 50 mm at an interrogation depth of about 2 to 100 mm.

One aspect of the invention includes a compact micro-transducer for in situ ultrasound measurements, comprising: at least one ultrasound crystal in acoustic communication with an acoustic coupling material, an ultrasound crystal holder adapted for securing the acoustic coupling material to a surface of an object or subject for in situ ultrasound measurements, and an electrical coupling electrically connecting the at least one ultrasound crystal and to an ultrasound output or recording system. The electrical coupling is disposed to allow the micro-transducer to be secured for in situ ultrasound measurements. Typically, the micro-transducer uses a plurality of crystals. A small number of crystals is often desirable to reduce weight and mass if circuitary is included in the micro-transducer. Preferably, a computer chip is included in the micro-transducer to facilitate signal transmission, reception or processing, or a combination thereof. The electrical connections, housing and micro-transducer materials can also be selected to reduce weight. Micro-transducer weights generally range between 5 and 150 grams, although larger and smaller micro-transducers can be used as well. Preferably, the micro-transducer is light to reduce pressure on the skin for continues monitoring. Micro-transducer weights are preferably about 50 grams or less and more preferably about 25 grams or less. The micro-transducer can also be adapted for continues monitoring applications in the skin. The time of continuous monitoring will vary depending on the clinically relevant time period. In some embodiments the acoustic coupling material and the ultrasound crystal holder are flexible.

Micro-transducers can be secured to skin using any means compatible with ultrasound transmission and detection. Typically, the micro-transducer can be lightly and securely taped to the skin using standard adhesive tape or adhesives that can provide for both secure attachment to the skin, as well as acoustic coupling as shown in FIGS. 5A and B. Although securely fastened to the skin, the pressure of the micro-transducer should be minimized to avoid artifacts. In the initial minutes of monitoring signals may vary due to short term skin effects or pressure effects. Such effects can be minimized or avoided by using biocompatible or hypoallergenic materials and minimum skin pressure. In some embodiments, the micro-transducer can include a separate positioning frame, generally only abut 10 to 20 percent larger than the micro-transducer, that holds the micro-transducer. As shown in FIG. 6, the frame 620 can have extending members 640 that can be secured to the skin and away from the interrogation site in order to reduce artifacts associated with probe placement. The structure of the frame can resemble a spider, where the body of the frame 620 secures the micro-transducer 600 and the legs of the positioning frame 630 secure the frame to the skin application site. Such spider embodiments of the positioning frame are particularly useful for securing the micro-transducer to an appendage region either by taping the legs or adjusting the legs to interlock. The positioning may be disposable and optionally include a sterile film disposed in the frame so as to provide a sterile micro-transducer surface. Acoustic coupling materials can be applied to either side of the film to enhance acoustic communication. The positioning frame can also include other fastening systems known in the art, such as velcro.

Alternatively the micro-transducer can be secured with adhesive coating. The adhesive coating can be applied to the skin of the subject or as part of the micro-transducer. Preferably, when acoustic coupling materials are applied to the skin, such as a gel, an adhesive can be included in the acoustic coupling materials to secure the micro-transducer.

In another embodiment the ultrasound crystal holder is adapted to attach to a securing member that secures an appendage of the human and secures the ultrasound crystal holder. This embodiment can immobilize the appendage and/or the micro-transducer. The acoustical coupling material can be secured in acoustical contact with the surface of the skin. An acoustic coupling gel can be optionally applied between the surface of the skin and the acoustical coupling material.

A micro-transducer can transmit signals that it receives to an ultrasound system for display or processing. Typically, a micro-transducer is electrically coupled to a system. Preferably, a light weight wire for transmitting electrical signals to an ultrasound computational unit is used. A micro-transducer can also be coupled with an infrared coupler to an ultrasound computational unit. More preferably, a micro-transducer is coupled using a radio frequency coupler that transmits signals to an ultrasound computational unit. Radio frequency and infrared coupling offers a number of advantages including reducing the weight of the micro-transducer by not requiring wires, permitting greater movement capabilities for either the subject or operator, and remote sensing.

Another aspect of the invention includes a micro-transducer comprising an acoustic surface acoustically coupled to an ultrasound source, wherein the acoustic surface and the ultrasound source are disposed in a frame adapted for directly or indirectly securing the micro-transducer to a skin. Typically, the micro-transducer is adapted for monitoring interstitial thickness. Preferably, the micro-transducer has surface area of about 3 $cm^2$ or less. Preferably, the micro-transducer is about 1 cm or less in thickness. To eliminate the inconvenience and weight of wiring to the micro-transducer the micro-transducer can transmit signals to an ultrasound system using infrared or radio frequency signals. The micro-transducer can be disposable. The micro-transducer can be sterile and further comprises a covering to protect the unit from contamination. The micro-transducer can also be connected to an ultrasound system with a coupling means for transmitting signals as known in the art or developed in the future.

Micro-transducers of the invention do not include ultrasound probes adapted for Doppler measurements in vessels and other ultrasound probes adapted for positioning on the surface of a body cavity.

EXAMPLES

General Materials and Methods:

The following materials and methods are exemplary of the materials and methods that can be used to achieve the results described herein. One skilled in the art will readily recognize substitute materials and methods.

In vitro and in vivo ultrasound measurements were performed using an Ultramark 9 HDI ultrasound system (Advanced Technologies Laboratories ("ATL"), 22100 Bothell Everett Hwy, Bothell, Wash. 98041-3003). All examinations were performed using a 5 MHz linear array transducer manufactured by ATL. An acoustic coupling gel was applied to the transducer surface and the object to be examined in order to reduce the impedance mismatch between the transducer surface and the object surface, usually skin. Data were acquired in B-scan mode. Two-dimensional gray-scale images of the various tissue/edema layers were obtained. Images were displayed on a computer monitor attached to the scanner hardware and capable of displaying the full gray scale range. Distance measurements were performed by saving a representative image displaying the various tissue layers, e.g. skin, subcutaneous fat and bone, on the display monitor. A trained physician identified the various tissue interfaces visually and placed cursors manually at the probe/skin, soft-tissue/bone, and other interfaces. Software provided with the ultrasound scanner was then used to calculate the distance between the calipers. All measurements were expressed in mm.

To maintain the anatomic location of the selected sites, a dye was used to mark the sites on the skin of the human subjects. Similarly, in the in vitro experiments, a dye was used to mark the measurement site on the external tissue surface.

Example 1

Ultrasonographic Measurement of Tissue Thickness in an In Vitro Model of Capillary Related Edema In order to evaluate the accuracy of ultrasonographic measurements for detecting edema and measuring interstitial fluid, experiments were performed with a sample of porcine muscle tissue creating a model of capillary related edema. Ultrasound measurements were correlated to results of anatomic examination. Ultrasonographic measurements were performed in a large piece of muscle tissue obtained from the gluteal region of a pig. The tissue was cut into thin sections using a rotating electric blade.

Two fluid-filled polymer film bags that were approximately 7 mm-thick when fully filled were prepared for insertion between the cut, separated muscle tissue layers. The surfaces of the polymer film bags and tissue were covered with a thin film of acoustic coupling gel. One or two bags were then placed in a sandwich-like fashion between the superior and the inferior muscle tissue layers thereby simulating an interposed fluid layer(s). A region of interest was defined at the external surface of the superior muscle tissue layer centered over the area where the bags had been placed and the region was marked with a dye. The ultrasound transducer was placed flush with the tissue surface in this region. An ultrasonographic image covering the total thickness of the tissue, defined as the distance from the outer surface of the superior muscle tissue layer to the outer surface of the inferior muscle tissue layer, was obtained. Both total tissue thickness as well as the thickness of the interposed fluid layer were measured on the image. Additionally, total tissue thickness with an empty polymer film bag inserted that was not filled with fluid and the thickness of the empty bag were measured with ultrasound. Total thickness and thickness of the interposed fluid layer were also determined anatomically with use of a ruler. The results of these experiments are set forth in Tables 6 and 7.

Table 6 compares the total tissue thickness measured by 1) anatomic measurement and 2) ultrasound measurements.

TABLE 6

| Interposed Layers | Anatomic Measurement of Total Tissue Thickness (in mm) | Ultrasound Measurement of Total Tissue Thickness (in mm) |
|---|---|---|
| Empty | 17 | 16.7 |
| 1 layer | 24 | 23.6 |
| 2 layers | 32 | 31.2 |

Table 7 compares the thickness of the interposed fluid layer measured by 1) anatomic measurement and, 2) ultrasound measurements.

TABLE 7

| Interposed Layers | Anatomic Measurement of Interposed Fluid Layer (in mm) | Ultrasound Measurement of Interposed Fluid Layer (in mm) |
|---|---|---|
| Empty | 0.8 | 0.7 |
| 1 layer | 7.0 | 7.0 |
| 2 layers | 14.0 | 14.3 |

Ultrasound and anatomic measurements were compared and the absolute and relative error of ultrasound measurements of total tissue thickness and of the thickness of the interposed fluid layer were calculated. The absolute error is defined as:

$$AE = US - AN,  \quad [\text{Eq. 4}],$$

where AE is the absolute error of the ultrasound measurement in mm, US is the ultrasonographic measurement of tissue thickness in mm, and AN is the tissue thickness determined by anatomic measurement in mm.

The relative error is defined as:

$$RE = \{(US - AN)/AN\} \times 100 \quad [\text{Eq. 5}]$$

Table 8 shows the absolute values of the absolute and relative errors of ultrasound measurements of total tissue thickness for different interposed fluid layers when compared to anatomic measurement.

TABLE 8

| Interposed Layers | Absolute Error (in mm) | Relative Error (in %) |
|---|---|---|
| Empty | 0.3 | 1.8 |
| 1 layer | 0.4 | 1.7 |
| 2 layers | 0.8 | 2.5 |

Table 9 shows the absolute values of the absolute and relative errors of ultrasound measurements of the thickness of the interposed fluid layers when compared to anatomic measurement.

TABLE 9

| Interposed Layers | Absolute Error (in mm) | Relative Error (in %) |
|---|---|---|
| Empty | 0.1 | 12.5 |
| 1 layer | 0.0 | 0.0 |
| 2 layers | 0.3 | 2.1 |

Table 10 shows the mean absolute and mean relative errors of ultrasound measurements averaged over all measurements of 1) total tissue thickness and 2) thickness of the interposed fluid layer.

TABLE 10

| Ultrasound Measurements | Mean Absolute Error (in mm) | Mean Relative Error (in %) |
|---|---|---|
| Total Tissue Thickness | 0.5 | 2.0 |
| Thickness of Interposed Fluid Layer | 0.1 | 4.9 |

The data generated in this in vitro model of pretibial edema demonstrate that ultrasound is a highly accurate technique for measuring thickness of a tissue with interposed fluid layers and for measuring the thickness and severity of the edema layer. Based on the results presented in Tables 6–10, the mean absolute error for measuring total tissue thickness and measuring the thickness of the interposed fluid layers ranged between 0.2 and 0.5 mm. Relative errors ranged between 2 and 4.9%. These results indicate that ultrasound techniques can monitor edema accurately and non-invasively in vitro, as well as in vivo.

Example 2

Ultrasonographic Measurement of Thickness of Capillary Related Edema in a Model of Venous Insufficiency and Right Ventricular Cardiac Failure This example documents, among other things, that ultrasound can be used in vivo to:

1) document rapid interstitial fluid shifts,
2) detect presence or progression of capillary related edema, e.g., capillary related edema secondary to impairment of cardiac or vascular function and
3) monitor presence or modulation of capillary related edema as a result of therapeutic intervention.

Two healthy male volunteers aged 36 and 34 years were studied. Distances between the knee joint space and the medial malleolus of the right calf were measured in each individual. The following landmarks were defined and marked in the right calf along the anterior aspect of the tibia:

1.) anterior aspect of the proximal third of the tibia,
2.) anterior aspect of the mid-tibia,
3.) anterior aspect of the distal third of the tibia, and
4.) medial aspect of the medial malleolus.

Measurement sites were marked on the skin with a pen. The circumference of the extremity was measured at these sites using a tape measure in both volunteers. Ultrasound measurements were then obtained at these sites. In the medial malleolus, the most protuberant portion was selected for scanning. A baseline measurement of tissue thickness was obtained at all four sites in both individuals prior to intervention. Individuals were in an upright and standing position before and during the experiments. Tissue thickness was defined as the distance from the probe/skin interface to the soft-tissue/bone interface. The soft-tissue/bone interface was prominently displayed on the B-scan images as a bright, echogenic reflector.

After a baseline was established, a tourniquet was applied to the distal thigh as a controllable maneuver to reduce blood flow. The tourniquet was sufficiently tight to retard venous drainage. Arterial pulses in the region of the posterior tibial and dorsalis pedis artery were, however, intact and preserved. Ultrasound measurements of tissue thickness were repeated at each site 15 min, 30 min, and 1 hour after application of the tourniquet. The tourniquet was removed after 1 hour and measurements were repeated at each site 30 min and 1 hour after release of the tourniquet.

In addition to the ultrasound measurements of capillary related edema, a trained physician examined both volunteers clinically for visual or palpatory evidence of edema at each time interval, i.e. prior to application of the tourniquet, 15 min, 30 min, and 1 hour after application of the tourniquet, as well as 30 min and 1 hour after removal of the tourniquet. Edema was clinically evaluated at the mid-tibial site by visual inspection and manual palpation. Using standard clinical techniques (see Bates et al., J. B. Lippincott, 1995), edema was subdivided into 5 grades:

0.) absent,
1.) slight,
2.) mild,
3.) moderate, and
4.) severe.

One skilled in the art can readily recognize that the techniques described herein can be applied to measuring changes in interstitial fluid in any other body region as well as in other living organisms in vivo.

Table 11 shows the ultrasound measurement of the thickness of the pretibial tissue/capillary related edema layer in the region of the proximal third of the tibia for different time intervals after application of the tourniquet.

TABLE 11

| Duration of Impaired Venous Drainage (in hr) | Ultrasound Measurements of Thickness of Pretibial Tissue/Capillary Related Edema Layer in the Proximal Third of the Tibia (in mm) | |
|---|---|---|
| | Subject 1 | Subject 2 |
| 0* | 3.0 | 3.4 |
| 0.25 | 3.1 | 4.8 |
| 0.5 | 4.4 | 5.1 |
| 1 | 5.5 | 5.5 |

*: measured immediately prior to application of tourniquet.

Table 12 shows the ultrasound measurement of the thickness of the pretibial tissue/capillary related edema layer in the region of the mid-tibia for different time intervals after application of the tourniquet.

TABLE 12

| Duration of Impaired Venous Drainage (in hr) | Ultrasound Measurements of Thickness of Pretibial Tissue/Capillary Related Edema Layer in the Mid-Tibia (in mm) | |
|---|---|---|
| | Subject 1 | Subject 2 |
| 0* | 2.3 | 2.3 |
| 0.25 | 2.3 | 4.0 |
| 0.5 | 2.9 | 3.8 |
| 1 | 4.0 | 4.5 |

*: measured immediately prior to application of tourniquet.

Table 13 shows the ultrasound measurement of the thickness of the pretibial tissue/capillary related edema layer in the region of the distal third of the tibia for different time intervals after application of the tourniquet.

TABLE 13

| Duration of Impaired Venous Drainage (in hr) | Ultrasound Measurements of Thickness of Pretibial Tissue/Capillary Related Edema Layer in the Distal Third of the Tibia (in mm) | |
|---|---|---|
| | Subject 1 | Subject 2 |
| 0* | 2.5 | 3.3 |
| 0.25 | 2.5 | 4.5 |
| 0.5 | 3.8 | 4.0 |
| 1 | 3.5 | 3.8 |

*: measured immediately prior to application of tourniquet.

Table 14 shows the ultrasound measurement of the thickness of the pretibial tissue/capillary related edema layer in the region of the medial malleolus of the tibia for different time intervals after application of the tourniquet.

TABLE 14

| Duration of Impaired Venous Drainage (in hr) | Ultrasound Measurements of Thickness of Tissue/Capillary Related Edema Layer in the Region of the Medial Malleolus (in mm) | |
|---|---|---|
| | Subject 1 | Subject 2 |
| 0* | 1.6 | 2.3 |
| 0.25 | 1.8 | 2.7 |
| 0.5 | 1.7 | 2.7 |
| 1 | 2.7 | 3.5 |

*: measured immediately prior to application of tourniquet.

Table 15 shows the results obtained with clinical assessment of pretibial edema in the region of the mid-tibia for different time intervals after application of the tourniquet.

TABLE 15

| Duration of Impaired Venous Drainage (in hr) | Clinical Assessment of Pretibial Edema | |
|---|---|---|
| | Subject 1 | Subject 2 |
| 0* | 0 | 0 |
| 0.25 | 0 | 0 |
| 0.5 | 0 | 0 |
| 1 | 1 | 1 |

*: measured immediately prior to application of tourniquet.

Tables 16–19 present the data obtained after release of the tourniquet.

Table 16 shows the ultrasound measurement of the thickness of the pretibial tissue/capillary related edema layer in the region of the proximal third of the tibia for different time intervals after removal of the tourniquet.

TABLE 16

| Duration of Restoration of Venous Drainage (in hr) | Ultrasound Measurements of Thickness of Pretibial Tissue/Capillary Related Edema Layer in the Proximal Third of the Tibia (in mm) | |
|---|---|---|
| | Subject 1 | Subject 2 |
| 0* | 5.5 | 5.5 |
| 0.5 | 4.2 | 4.9 |
| 1 | 3.6 | 3.9 |

*: measured immediately prior to removal of tourniquet.

Table 17 shows the ultrasound measurement of the thickness of the pretibial tissue/capillary related edema layer in the region of the mid-tibia for different time intervals after removal of the tourniquet.

TABLE 17

| Duration of Restoration of Venous Drainage (in hr) | Ultrasound Measurements of Thickness of Pretibial Tissue/Capillary Related Edema Layer in the Mid-Tibia (in mm) | |
|---|---|---|
| | Subject 1 | Subject 2 |
| 0* | 4.0 | 4.5 |
| 0.5 | 3.5 | 3.3 |
| 1 | 2.9 | 2.4 |

*: measured immediately prior to removal of tourniquet.

Table 18 shows the ultrasound measurement of the thickness of the pretibial tissue/capillary related edema layer in the region of the distal third of the tibia for different time intervals after removal of the tourniquet.

TABLE 18

| Duration of Restoration of Venous Drainage (in hr) | Ultrasound Measurements of Thickness of Pretibial Tissue/Capillary Related Edema Layer in the Distal Third of the Tibia (in mm) | |
|---|---|---|
| | Subject 1 | Subject 2 |
| 0* | 3.5 | 3.8 |
| 0.5 | 3.4 | 3.5 |
| 1 | 3.4 | 3.1 |

*: measured immediately prior to removal of tourniquet.

Table 19 shows the ultrasound measurement of the thickness of the pretibial tissue/capillary related edema layer in the region of the medial malleolus of the tibia for different time intervals after removal of the tourniquet

TABLE 19

| Duration of Restoration of Venous Drainage (in hr) | Ultrasound Measurements of Thickness of Tissue/Capillary Related Edema Layer in the Region of the Medial Malleolus (in mm) | |
|---|---|---|
| | Subject 1 | Subject 2 |
| 0* | 2.7 | 3.5 |
| 0.5 | 1.4 | 2.3 |
| 1 | 1.6 | 2.0 |

*: measured immediately prior to removal of tourniquet.

Table 20 shows the results obtained with clinical assessment of pretibial edema in the region of the mid-tibia for different time intervals after removal of the tourniquet.

TABLE 20

| Duration of Restoration of Venous Drainage (in hr) | Clinical Assessment of Pretibial Edema | |
|---|---|---|
| | Subject 1 | Subject 2 |
| 0* | 1 | 1 |
| 0.5 | 1 | 1 |
| 1 | 1 | 1 |

*: measured immediately prior to removal of tourniquet.

Based on the data presented in Tables 11–14 and 16–19 percent change in thickness of the pretibial tissue/capillary related edema layer was calculated for the four different sites for measurements obtained after application and after removal of the tourniquet. Percent increase after application of the tourniquet was calculated as:

$$\% \text{ increase} = \{(US_{ts} - US_{preTourniquet})/US_{preTourniquet}\} \times 100 \quad [\text{Eq. 6}].$$

Percent decrease after removal of the tourniquet was calculated as:

$$\% \text{ decrease} = \{(US_{ts} - US_{Tourniquet})/US_{Tourniquet}\} \times 100 \quad [\text{Eq. 7}],$$

where is $US_{ts}$ is the ultrasonographic measurement of the thickness of the pretibial tissue/capillary related edema layer for a given time point "t" and a given measurement site. $US_{PreTourniquet}$ is the thickness of the pretibial tissue/edema layer prior to application of the tourniquet for the experiments in which the tourniquet had been applied. $US_{Tourniquet}$ is the thickness of the pretibial tissue/capillary related edema layer prior to removal of the tourniquet for the experiments in which the tourniquet had been removed.

The percent change in thickness of the pretibial tissue/capillary related edema layer after application of the tourniquet, e.g. to simulate onset of diseased state, and after removal of the tourniquet, e.g. to simulate medical intervention and treatment of diseased state, is shown in Tables 21 and 22 and is averaged for both volunteers.

Table 21 shows the mean percent increase in thickness of the pretibial tissue/edema layer from baseline ($US_{PreTourniquet}$) compared to the different time intervals after application of the tourniquet measured by ultrasound at all four sites.

TABLE 21

Mean Percent Increase in Thickness
of Pretibial Tissue/Capillary Related
Edema Layer after Application of Tourniquet*

| Duration of Impaired Venous Drainage (in hr) | Proximal Third of Tibia (in %) | Mid-Tibia (in %) | Distal Third of Tibia (in %) | Medial Malleolus (in %) |
|---|---|---|---|---|
| 0.25 | 022.3 | 37.0 | 18.2 | 14.9 |
| 0.5 | 48.3 | 45.7 | 36.6 | 11.8 |
| 1 | 72.5 | 84.8 | 27.6 | 60.5 |

*data averaged for both volunteers.

Table 22 shows the mean percent decrease in thickness of the pretibial tissue/capillary related edema layer from baseline ($US_{Tourniquet}$) compared to the different time intervals after removal of the tourniquet measured by ultrasound at all four sites.

TABLE 22

Mean Percent Decrease in Thickness of
Pretibial Tissue/Capillary Related
Edema Layer after Removal of Tourniquet*

| Duration of Restoration of Venous Drainage (in hr) | Proximal Third of Tibia (in %) | Mid-Tibia (in %) | Distal Third of Tibia (in %) | Medial Malleolus (in %) |
|---|---|---|---|---|
| 0.5 | 17.3 | 19.6 | 5.4 | 41.2 |
| 1 | 31.8 | 37.1 | 10.7 | 41.8 |

*data averaged for both volunteers.

To assess the sensitivity of the technique in relation to the size of the leg, anatomical regions were measured. The circumference of the calf was measured in both volunteers at each measurement site using a tape measure. Based on measurements of the circumference, the radius R of the calf was calculated for each site as:

$$R = C/2\pi \quad [\text{Eq. 8}],$$

where C is the circumference of the calf at a given measurement site.

Table 23 shows circumference and radius of the calf in both volunteers for all four measurement sites.

TABLE 23

| | Calf Circumference (in mm) | | Radius (in mm) | |
|---|---|---|---|---|
| Anatomic Site | Subject 1 | Subject 2 | Subject 1 | Subject 2 |
| Prox. Third of Tibia | 366 | 380 | 58.2 | 60.5 |
| Mid-Tibia | 334 | 345 | 53.1 | 54.9 |
| Distal Third of Tibia | 228 | 260 | 36.3 | 41.4 |
| Medial Malleolus | 250 | 260 | 39.8 | 41.4 |

Based on the data presented in Tables 21–23, percent change in thickness of the pretibial tissue/capillary related edema layer relative to the radius or the circumference of the calf at the different measurement sites was calculated for measurements obtained after application and after removal of the tourniquet. Percent increase after application of the tourniquet relative to the radius was calculated for each individual as:

% Increase$_{Edema/Radius}$={|($US_{ts}$−$US_{PreTourniquet}$)|/$R$}×100      [Eq. 9].

Percent increase after application of the tourniquet relative to the circumference was calculated for each individual as:

% Increase$_{Edema/Circumference}$={|($US_{ts}$−$US_{PreTourniquet}$)|$C$}×100      [Eq. 10].

Similarly, percent decrease after removal of the tourniquet relative to the radius was calculated for each individual as:

% Decrease$_{Edema/Radius}$={|($US_{ts}$−$US_{Tourniquet}$)|/$R$}×100      [Eq. 11]

Percent decrease after removal of the tourniquet relative to the circumference was calculated for each individual as:

% Decrease$_{Edema/Circumference}$={|($US_{ts}$−$US_{Tourniquet}$)|$C$}×100      [Eq. 12]

Table 24 shows the mean percent increase in thickness of the pretibial tissue/capillary related edema layer relative to the calf radius averaged over both volunteers at the different time intervals after application of the tourniquet. The method described herein is quite sensitive, as it can detect changes in calf radius less than about 1.0 to 1.5% of the calf radius. Larger changes of about 5 or 10 percent or greater can also be measured as described herein.

TABLE 24

Mean Percent Increase in Thickness of Pretibial Tissue (Capillary Related Edema Layer after Application of Tourniquet Relative to Calf Radius*

| Duration of Impaired Venous Drainage (in hr) | Proximal Third of Tibia (in %) | Mid-Tibia (in %) | Distal Third of Tibia (in %) | Medial Malleolus (in %) |
|---|---|---|---|---|
| 0.25 | 1.2 | 1.6 | 1.5 | 0.7 |
| 0.5 | 2.6 | 1.9 | 2.6 | 0.6 |
| 1 | 3.9 | 3.6 | 2.0 | 2.8 |

*data averaged for both volunteers.

Table 25 shows the mean percent increase in thickness of the pretibial tissue/capillary related edema layer relative to the calf circumference averaged over both volunteers at the different time intervals after application of the tourniquet. The method described herein is quite sensitive, as it can detect changes in calf circumference less than about 0.2 to 0.5% of the calf circumference. Larger changes of about 5 or 10 percent or greater can also be measured as described herein.

TABLE 25

Mean Percent Increase in Thickness of Pretibial Tissue/ Capillary Related Edema Layer after Application of Tourniquet Relative to Calf Circumference*

| Duration of Impaired Venous Drainage (in hr) | Proximal Third of Tibia (in %) | Mid-Tibia (in %) | Distal Third of Tibia (in %) | Medial Malleolus (in %) |
|---|---|---|---|---|
| 0.25 | 0.2 | 0.3 | 0.2 | 0.1 |
| 0.5 | 0.4 | 0.3 | 0.4 | 0.1 |
| 1 | 0.6 | 0.6 | 0.3 | 0.5 |

*data averaged for both volunteers.

Table 26 shows the mean percent decrease in thickness of the pretibial tissue/capillary related edema layer relative to the calf radius averaged over both volunteers at the different time intervals after removal of the tourniquet.

TABLE 26

Mean Percent Decrease in Thickness of Pretibial Tissue/Capillary Related Layer after Removal of Tourniquet Relative to Calf Radius*

| Duration of Restoration of Venous Drainage (in hr) | Proximal Third of Tibia (in %) | Mid-Tibia (in %) | Distal Third of Tibia (in %) | Medial Malleolus (in %) |
|---|---|---|---|---|
| 0.5 | 1.6 | 1.6 | 0.5 | 3.1 |
| 1 | 3.0 | 3.0 | 1.0 | 3.2 |

*data averaged for both volunteers.

Table 27 shows the mean percent decrease in thickness of the pretibial tissue/capillary related edema layer relative to the calf circumference averaged over both volunteers at the different time intervals after removal of the tourniquet.

TABLE 27

Mean Percent Decrease in Thickness of Pretibial Tissue/Capillary Related Edema Layer after Removal of Tourniquet Relative to Calf Circumference*

| Duration of Restoration of Venous Drainage (in hr) | Proximal Third of Tibia (in %) | Mid-Tibia (in %) | Distal Third of Tibia (in %) | Medial Malleolus (in %) |
|---|---|---|---|---|
| 0.5 | 0.3 | 0.3 | 0.2 | 0.5 |
| 1 | 0.5 | 0.5 | 0.2 | 0.5 |

*data averaged for both volunteers.

The results presented in Tables 11–15 and Table 21 demonstrate that ultrasound is a sensitive technique to detect interstitial fluid shifts and quantitate the amount of interstitial fluid. Ultrasound also appears to be extremely useful for early or rapid detection of changes in capillary related interstitial fluid. Significant increases in interstitial fluid can be detected as early as 15 minutes after alteration of venous drainage. The mean percent increase in thickness of pretibial capillary related edema 15 minutes after impairment of venous drainage was 22.3% at the proximal tibia and 37.0% at the mid-tibia (Table 21). After 1 hour of impaired venous drainage, the tissue thickness in the mid-tibia measured by ultrasound had almost doubled. Clinical examination, i.e. combined visual inspection and manual palpation, did not detect any changes during the 15 minutes and 30 minutes observation periods. Only a slight change (grade I) could be detected at the 1 hour interval (Table 15). These results demonstrate that ultrasound is substantially more sensitive than clinical examination in detecting interstitial fluid shifts, which can be seen with venous insufficiency and cardiac disease, as well as other disease states and therapeutic interventions.

When the tourniquet was removed (Tables 16–20 & 22), the model can clinically correspond to therapeutic intervention, e.g. administration of cardiac or other drugs. Significant changes could be observed as early as 30 minutes after removal of the tourniquet. Thirty minutes after removal of the tourniquet, the mean decrease in pretibial interstitial fluid layer thickness amounted to 17.3% in the proximal third of the tibia and 19.6% in the mid-tibia (Table 22). Clinical examination, however, showed no change even 1 hour after removal of the tourniquet confirming that clinical examination is unreliable in assessing the presence and the amount of edema (Table 20). These results show that, unlike clinical examination, ultrasound, can be used for early or continuous monitoring and quantification of the efficacy of therapeutic interventions in medical conditions that lead to interstitial edema.

The data presented in Tables 24–27 indicate that ultrasound is extremely sensitive in detecting subtle shifts in interstitial fluid. The changes in thickness of the soft-tissue/edema layer that were detected with ultrasound ranged between 0.5 and 3.9% when compared to the radius of the calf and between 0.1 and 0.6% when compared to the circumference of the calf.

Example 3

Ultrasonographic Measurement of Thickness of Pretibial Edema in a Model of Capillary Related Edema Secondary to Abnormal Colloid Osmotic Pressure and/or Renal Failure This example documents that ultrasound can be used in vivo to detect subtle changes in interstitial fluid. The example shows that changes in pretibial interstitial fluid layer thickness relate directly to the volume of interstitial fluid. Two healthy volunteers aged 36 and 34 years were examined with ultrasound. The distance between the medial knee joint space and the medial malleolus of the left calf was measured in each individual. Using these measurements, the mid-region of the anterior tibia was identified for ultrasound measurements. The measurement site was marked on the skin with a pen. A baseline measurement of tissue thickness was obtained with ultrasound at the marked site in both individuals prior to intervention. Tissue thickness was defined as the distance from the probe/skin to the soft-tissue/bone interface. The soft-tissue/bone interface was prominently displayed on the B-scan images as a bright, echogenic reflector.

The measurement site was then cleaned with iodine solution for disinfection. A 10 cc syringe was filled with 1% Xylocaine solution (Astra Pharmaceuticals, Westborough, Mass. 01581). A sterile 25 Gauge needle was attached to the syringe and small volumes of Xylocaine were injected into the pretibial soft-tissues. The total injected volume was recorded. After each injection, an ultrasonographic measurement of pretibial interstitial fluid layer thickness was obtained. Injected volumes were 0.5 cc, 1.5 cc, and 2.5 cc.

Table 28 shows the ultrasound measurement of the thickness of the pretibial edema layer in the region of the mid-tibia after local injection of 1% Xylocaine solution for different injection volumes.

TABLE 28

| Amount of Fluid injected (in cc) | Ultrasound Measurements of Thickness of Pretibial Edema Layer (in mm) | |
|---|---|---|
| | Subject 1 | Subject 2 |
| 0* | 2.6 | 2.4 |
| 0.5 | 7.2 | 4.8 |
| 1.5 | 9.0 | 6.8 |
| 2.5 | 9.5 | 7.6 |

*: measured prior to injection.

Once 2.5 cc of 1% Xylocaine solution had been injected, injection was stopped and serial ultrasound measurements of pretibial fluid/edema layer thickness were obtained immediately after injection, and 30 min, 1 hour, 1.5 hours, and 2 hours after injection.

Table 29 shows the ultrasound measurement of the thickness of the pretibial edema layer in the region of the mid-tibia for different time intervals after injection of 2.5 cc 1% Xylocaine solution.

TABLE 29

| Time Interval since Injection of 2.5 cc (in hr) | Ultrasound Measurements of Thickness of Pretibial Edema Layer (in mm) | |
|---|---|---|
| | Subject 1 | Subject 2 |
| 0* | 9.5 | 7.6 |
| 0.5 | 5.5 | 5.0 |
| 1 | 5.0 | 5.7 |
| 1.5 | 4.4 | 4.5 |
| 2.0 | — | 4.3 |

*: measured immediately after completion of injection;
-: not obtained.

Table 30 shows the percent decrease in thickness of the pretibial edema layer measured by ultrasound in the region of the mid-tibia for different time intervals after injection of 2.5 cc 1% Xylocaine solution.

TABLE 30

| Time Interval since Injection (in hr) | Percent Decrease in Thickness of Pretibial Edema Layer* | |
|---|---|---|
| | Subject 1 (in %) | Subject 2 (in %) |
| 0.5 | 42.1 | 34.2 |
| 1 | 47.4 | 25.0 |
| 1.5 | 53.7 | 40.8 |
| 2.0 | — | 43.4 |

*: data compared to baseline thickness measured immediately after completion of injection;
-: not obtained.

The data presented in Table 28 indicate that ultrasound is a very sensitive technique in detecting very small changes in interstitial fluid volume. Injection of as little as 0.5 cc resulted in an ultrasonographic change in the thickness of the pretibial soft-tissue/edema layer of 100% and greater. These results demonstrate that ultrasound has very high sensitivity in measuring subtle interstitial fluid shifts. Moreover, as seen in Table 28, ultrasonographic measurement of pretibial interstitial fluid layer thickness correlated well with the volume of injected fluid. This demonstrates that ultrasonographic measurement of the thickness of the interstitial fluid layer in the pre-tibial area as well as potentially other anatomic regions represents a new diagnostic parameter that relates directly to the interstitial fluid volume. The data presented in Tables 29 and 30 show that ultrasound cannot only be used to detect edema, but also to monitor interstitial fluid longitudinally over time and to assess resolution of edema, for example secondary to medical treatment.

PUBLICATIONS

U.S. PATENT DOCUMENTS

| | | |
|---|---|---|
| 4,658,827 | Dec. 21, 1987 | He, P., et al. |
| 4,446,737 | May 8, 1984 | Hottier, F. |
| 4,920,966 | May 1, 1990 | Hon, E. R. |
| 4,224,829 | Sep. 30, 1980 | Kawabuchi, M., et al. |
| 08/731,821 | Filed Oct. 21, 1996 | Lang, P., et al. |
| 4,242,911 | Jan. 6, 1981 | Martin, H. E. |
| 4,688,428 | Aug. 25, 1987 | Nicolas, J.-M. |

-continued
PUBLICATIONS

| | | |
|---|---|---|
| 4,702,258 | Oct. 27, 1987 | Nicolas, J.-M., et al. |
| 4,043,181 | Aug. 23, 1977 | Nigam, A. K. |
| 4,830,015 | May 16, 1989 | Okazaki, K. |
| 5,271,403 | Dec. 21, 1993 | Paulos, J. J. |
| 4,833,323 | May 23, 1989 | Scholze, C. |
| 5,303,708 | Apr. 19, 1994 | Stouffer, J. R. |
| 5,316,003 | May 31, 1994 | Stouffer, J. R. |
| 5,617,864 | Apr. 8, 1997 | Stouffer, J. R., et al. |

FOREIGN PATENT DOCUMENTS

| | | |
|---|---|---|
| PCT WO 93/12419 | June 24, 1993 | Lake, R. J., et al. |

OTHER PUBLICATIONS

Physician's 1991 drug handbook, pp. 1099–1103, 1991.
Agner, T., et al., Contact Dermatitis, vol. 20, pp. 352–359, 1989.
Agner, T., et al., Clin Exp Dermtol, vol. 15, pp. 29–33, 1990.
Agner, T., et al., J Invest Dermatol, vol. 95 (5), pp. 543–547, 1990.
Alexander, H., et al., J Invest Dermatol, vol. 72 (1), pp. 17–19, 1979.
Barnes, M., et al., Phlebology, vol. 7, pp. 31–35, 1992.
Bates, B., et al., in: "A guide to physical examination and history taking, 6th edition", Bates, B., et al., eds., pp. 427–447, 1995.
Bhagat, P. K., et al., Ultrasound Med Biol, vol. 6, pp. 369–375, 1980.
Braunwald, E., in "Harrison's Principles of Internal Medicine", Isselbacher, K. J., Braunwald, E., et al., eds., pp 183–187, 1994.
Brazier, S., et al., Contact Dermatitis, vol. 15, pp. 199–201, 1986.
Bushberg, J. T., et al. "The essential physics of medical imaging", 1994.
Campbell, I. T., et al., Am J Clin Nutr, vol. 62, pp. 533–539, 1995.
Carpenter, D. A., et al., Radiology, vol. 195 (2), pp. 563–567, 1995.
Cohen, J. S., et al., Arthritis & Rheumatism, vol. 27, pp. C65, 1984.
Ciocon, J. O., et al., Angiology, vol. 46, pp. 19–25, 1995.
deRigal, J., et al., J Invest Dermatol, vol. 93 (5), pp. 621–625, 1989.
Dykes, P. J., et al., J Invest Dermatol, vol. 69, pp. 275, 1977.
Escoffier, C., et al., Bioeng Skin, vol. 2, pp. 87–94, 1986.
Fornage, B., et al., J Clin Ultrasound, vol. 14, pp. 619–622, 1986.
Fornage, B., et al., Radiology, vol. 189, pp. 69–76, 1993.
Fornage, B. D., Radiologia Medica, vol. 85 (5 Suppl. 1), pp. 149–155, 1993.
Fornage, B. D., Clinics in Diagnostic Ultrasound, vol. 30, pp. 85–98, 1995.
Gniadecka, M., et al., Br J Dermatol, vol. 131, pp. 849–855, 1994.
Gniadecka, M., et al., J Invest Dermatol, vol. 102 (3), pp. 362–364, 1994.
Gniadecka, M., Acta Derm Venereol, vol. 75, pp. 120–124, 1995.
Gniadecka, M., Skin Res Technology, vol. 1, pp. 55–60, 1995.
Gniadecka, M., J Am Acad Dermatol, vol. 35, pp. 37–41, 1996.
Gottlieb, S. H., in: "Principles of ambulatory medicine", Barker, L. R., et al., eds., pp. 736–754, 1991.
Goss, S. A., et al., J Acoust Soc Am, vol. 64 (2), pp. 423–457, 1978.
Hermann, R. C., et al., Skin Pharmacol, vol. 1, pp. 128–136, 1988.

-continued
PUBLICATIONS

Killewich, L. A., et al., Archives of Surgery, vol. 120 (4), pp 424–426, 1985
Krijnen, R. M. A., et al., Dermatology, vol. 194, pp. 121–126, 1997.
Ludwig, M., et al., Schweizerische Rundschau fuer Medizin Praxis, vol. 78 (37), pp. 987–992, 1989.
Milner, S. M., et al., Dermatologic Surgery, vol. 23 (1), pp. 43–35, 1997.
Munson, P. L. "Principles of pharmacology. Basic concepts and clinical applications", 1995.
Querleux, B., et al., Dermatologica, vol. 177, pp. 332–337, 1988.
Reali, U., et al., Plast Reconstr Surg, vol. 93, pp. 1050–1055, 1994.
Richard, S., et al., J Invest Dermatol, vol. 100 (5), pp. 705–709, 1993.
Salmi, A., et al., Plastic and Reconstr Surg, vol. 97, pp. 1443–1450, 1995.
Seidenari, S., et al., Contact Dermatitis, vol. 24, pp. 216–222, 1991.
Seidenari, S., et al., Contact Dermatitis, vol. 25, pp. 329, 1991.
Seidinari, S., et al., Contact Dermatitis, vol. 26, pp. 171–176, 1992.
Seidenari, S., et al., Acta Derm Venereol, vol. Suppl. 175, pp. 3–7, 1992.
Seidenari, S., et al., Acta Derm Venereol, vol. Suppl. 175, pp. 9–13, 1992.
Seidenari, S., et al., Contact Dermatitis, vol. 27, pp. 331–332, 1992.
Serup, J., et al., Contact Dermatitis, vol. 10, pp. 88–93, 1984.
Serup, J., Acta Derm Venereol, vol. 64, pp. 214–219, 1984.
Serup, J., et al., Contact Dermatitis, vol. 17, pp. 80–84, 1987.
Sondergaard, J., et al., Acta Dermatovenerol, vol. 65, suppl. 120, pp. 76–82, 1985.
Tan, C. Y., et al., Br J. Dermatol, vol. 106, pp. 657–667, 1982.
Tan, C. Y., et al., J Invest Dermatol, vol. 76, pp. 126–128, 1981.
Tan, C. Y., et al., in: "Bioengineering and the skin", Marks, R., et al., eds., pp. 215–225, 1981.
Williams, P., et al. "Gray's anatomy, 36th British Edition", 1980.

All documents and publications, including patents and patent application documents, are herein incorporated by reference to the same extent as if each publication were individually incorporated by reference.

We claim:

1. A method of detecting rapid changes in capillary related interstitial fluid volume in a human, comprising:
   a) positioning a first ultrasound probe on a skin surface of a first anatomical region of said human in need of capillary related interstitial fluid volume detection during a clinically relevant fine period,
   b) interrogating said first anatomical region with ultrasound pulses from said first ultrasound probe, and
   c) detecting a first capillary related interstitial fluid volume between an inner surface of skin and either a bone or fat surface in said first anatomical region with ultrasound signals from said ultrasound pulses, wherein said first capillary related interstitial fluid volume is an indicator of capillary related interstitial fluid volume of said first anatomical region or is an indicator of systemic capillary related interstitial fluid volume.

2. The method of claim 1, further comprising the step of comparing said first capillary related interstitial fluid volume to a predetermined value for capillary related interstitial fluid layer volume.

3. The method of claim 2, wherein said anatomical region is selected from the group consisting of a tibial region, a humerus region, a chest region, an abdominal region, and a cranial region.

4. The method of claim 3, wherein said measuring is a quantitative measurement of capillary related interstitial fluid volume comprising determining a capillary related interstitial layer thickness or a capillary related interstitial layer volume.

5. The method of claim 4, wherein said measuring detects about a 1 millimeter or greater change in interstitial layer thickness.

6. The method of claim 5, wherein said measuring occurs during at least two predetermined monitoring times or measuring occurs continuously during said clinically relevant time period.

7. The method of claim 6, wherein said measuring occurs over more than a 20 minute time frame.

8. The method of claim 7, wherein said probe remains in approximately the same position during said measuring and said measurements occur no less than 1 per minute at regularly spaced intervals.

9. The method of claim 8, further comprising placing a plurality of probes at different anatomical regions and performing steps (a) through (c) for each anatomical region.

10. The method of claim 9, wherein said plurality of probes comprises a left tibial region probe, and a right tibial region probe, wherein said steps (a) through (c) are performed concurrently with said plurality of probes.

11. The method of claim 10, wherein said plurality of probes further comprises a humerus probe, cranial probe, chest probe, and an abdominal probe, and wherein said steps (a) through (c) are performed concurrently with said plurality of probes.

* * * * *